United States Patent
Suzuki et al.

(10) Patent No.: US 9,329,134 B2
(45) Date of Patent: May 3, 2016

(54) REFLECTION TYPE OPTICAL SENSOR AND IMAGE GENERATION APPARATUS

(71) Applicants: Hidemasa Suzuki, Yamato (JP); Koji Masuda, Yokohama (JP); Susumu Momma, Ebina (JP)

(72) Inventors: Hidemasa Suzuki, Yamato (JP); Koji Masuda, Yokohama (JP); Susumu Momma, Ebina (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/635,411

(22) Filed: Mar. 2, 2015

(65) Prior Publication Data
US 2015/0168310 A1    Jun. 18, 2015

Related U.S. Application Data

(63) Continuation of application No. 14/023,032, filed on Sep. 10, 2013, now Pat. No. 9,116,130.

(30) Foreign Application Priority Data

Sep. 11, 2012  (JP) ................................. 2012-199379
Sep. 18, 2012  (JP) ................................. 2012-204291

(51) Int. Cl.
    *G01N 21/892*    (2006.01)
    *G01N 21/89*     (2006.01)
    *G01N 21/55*     (2014.01)

(52) U.S. Cl.
    CPC .............. *G01N 21/892* (2013.01); *G01N 21/55* (2013.01); *G01N 21/8903* (2013.01); *G01N 2201/0638* (2013.01)

(58) Field of Classification Search
    None
    See application file for complete search history.

(56) References Cited

U.S. PATENT DOCUMENTS

| | | | |
|---|---|---|---|
| 5,142,416 A | 8/1992 | Nakamura et al. | |
| 5,875,051 A | 2/1999 | Suzuki et al. | |
| 5,964,339 A | 10/1999 | Matsuura et al. | |
| 5,986,791 A | 11/1999 | Suzuki et al. | |

(Continued)

FOREIGN PATENT DOCUMENTS

| JP | 1-159341 | 6/1989 |
|---|---|---|
| JP | 2-306513 A | 12/1990 |

(Continued)

OTHER PUBLICATIONS

Office Action issued Mar. 10, 2015 in Japanese Patent Application No. 2012-204291.

*Primary Examiner* — Clayton E Laballe
*Assistant Examiner* — Jas Sanghera
(74) *Attorney, Agent, or Firm* — Oblon, McClelland, Maier & Neustadt, L.L.P.

(57) ABSTRACT

A reflection type optical sensor that detect a surface condition of a moving body and that is used for an image generation apparatus which forms images on a recording media includes a light-emitting device which has a plurality of light emitter systems including at least two light-emitting members and a light-emitting optical system having a plurality of light-emitting lenses corresponding to a plurality of the light emitter systems and guiding light emitted from the light emitter systems to the moving body and a light-receiving device which has a light receiver system including at least two light-receiving members and a light-receiving optical system having light-receiving lenses corresponding to the at least two light-receiving members and guiding light reflected by the moving body to the light receiver system. The image generation apparatus has further a surface condition judging device in addition to the reflection type optical sensor.

19 Claims, 69 Drawing Sheets

(56) References Cited

U.S. PATENT DOCUMENTS

| | | |
|---|---|---|
| 6,069,724 A | 5/2000 | Hayashi et al. |
| 6,075,638 A | 6/2000 | Masuda |
| 6,081,386 A | 6/2000 | Hayashi et al. |
| 6,141,133 A | 10/2000 | Suzuki et al. |
| 6,222,662 B1 | 4/2001 | Suzuki et al. |
| 6,259,546 B1 | 7/2001 | Masuda |
| 6,384,949 B1 | 5/2002 | Suzuki |
| 6,496,214 B1 | 12/2002 | Masuda et al. |
| 6,642,505 B1 | 11/2003 | Nakano et al. |
| 7,784,694 B2 | 8/2010 | Foo |
| 2002/0101642 A1 | 8/2002 | Masuda |
| 2003/0007067 A1 | 1/2003 | Masuda et al. |
| 2004/0141218 A1 | 7/2004 | Suzuki |
| 2006/0016970 A1* | 1/2006 | Nagasaka et al. ........ 250/231.13 |
| 2006/0256183 A1 | 11/2006 | Masuda |
| 2007/0146473 A1 | 6/2007 | Masuda |
| 2008/0084594 A1 | 4/2008 | Masuda |
| 2009/0009838 A1 | 1/2009 | Masuda |
| 2009/0015896 A1 | 1/2009 | Masuda |
| 2009/0153930 A1 | 6/2009 | Masuda |
| 2009/0238590 A1 | 9/2009 | Masuda |
| 2010/0008686 A1 | 1/2010 | Masuda et al. |
| 2010/0266302 A1 | 10/2010 | Suzuki et al. |
| 2010/0310284 A1 | 12/2010 | Funato et al. |
| 2011/0043810 A1 | 2/2011 | Suzuki et al. |
| 2011/0044713 A1 | 2/2011 | Masuda et al. |
| 2012/0268750 A1 | 10/2012 | Masuda |
| 2013/0243446 A1 | 9/2013 | Masuda |
| 2013/0243458 A1 | 9/2013 | Suzuki et al. |
| 2013/0308966 A1 | 11/2013 | Masuda et al. |

FOREIGN PATENT DOCUMENTS

| | | | | |
|---|---|---|---|---|
| JP | 5-113739 | | 5/1993 | |
| JP | 6-3998 | | 1/1994 | |
| JP | 6-27549 | | 2/1994 | |
| JP | 8-262204 A | | 10/1996 | |
| JP | 2006-251165 | | 9/2006 | |
| JP | 2007-34068 | | 2/2007 | |
| JP | 2007-278711 | | 10/2007 | |
| JP | 2010-39460 A | | 2/2010 | |
| JP | 2011-64822 | | 3/2011 | |
| JP | 2011-064822 A | * | 3/2011 | ............. G03G 15/00 |
| JP | 2011-180527 | | 9/2011 | |

* cited by examiner

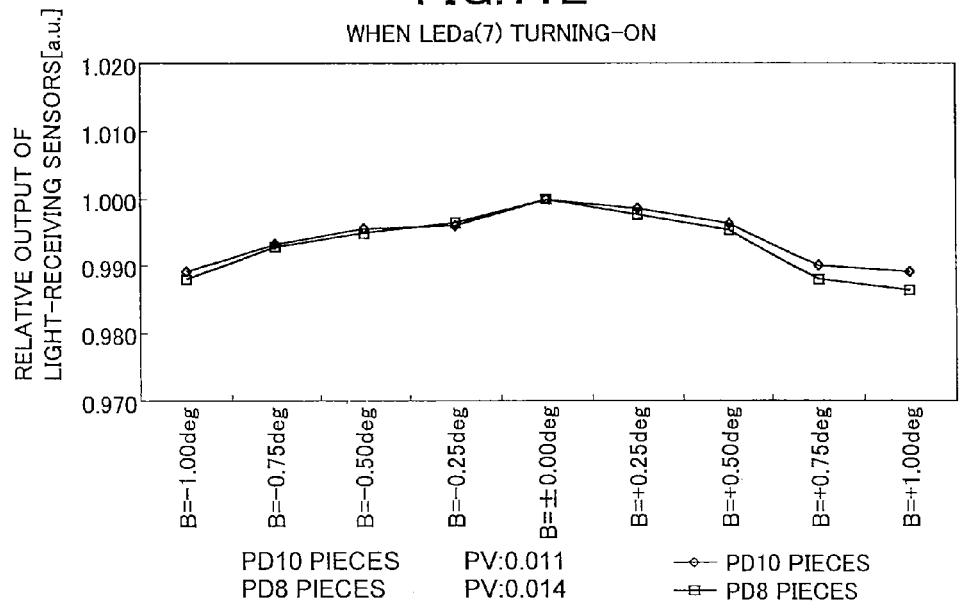
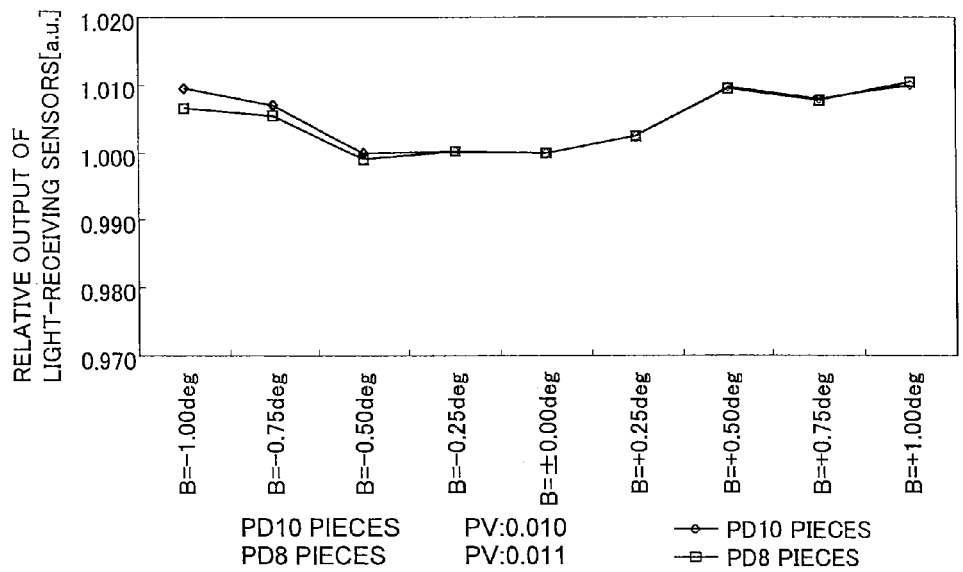

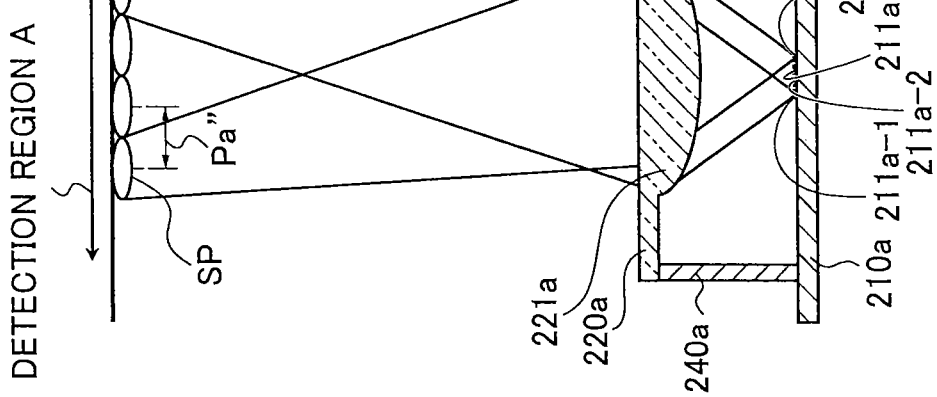
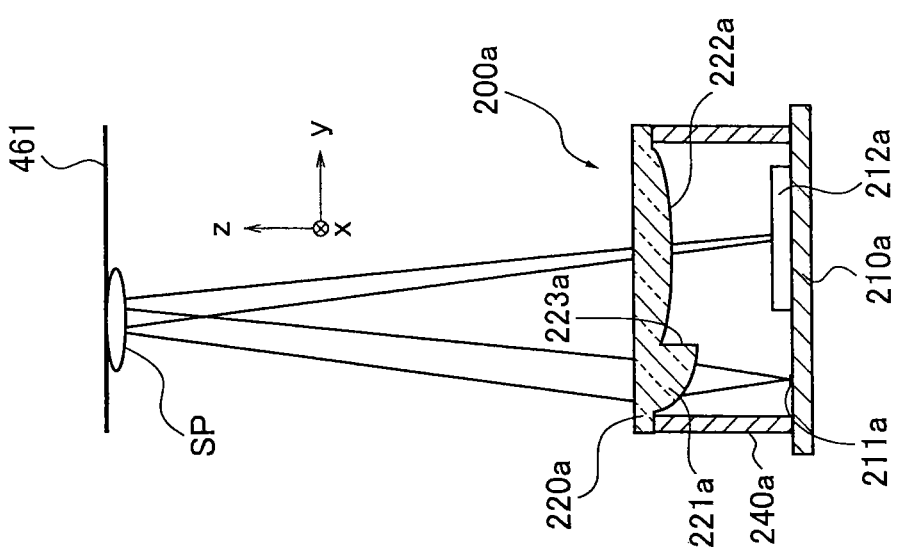

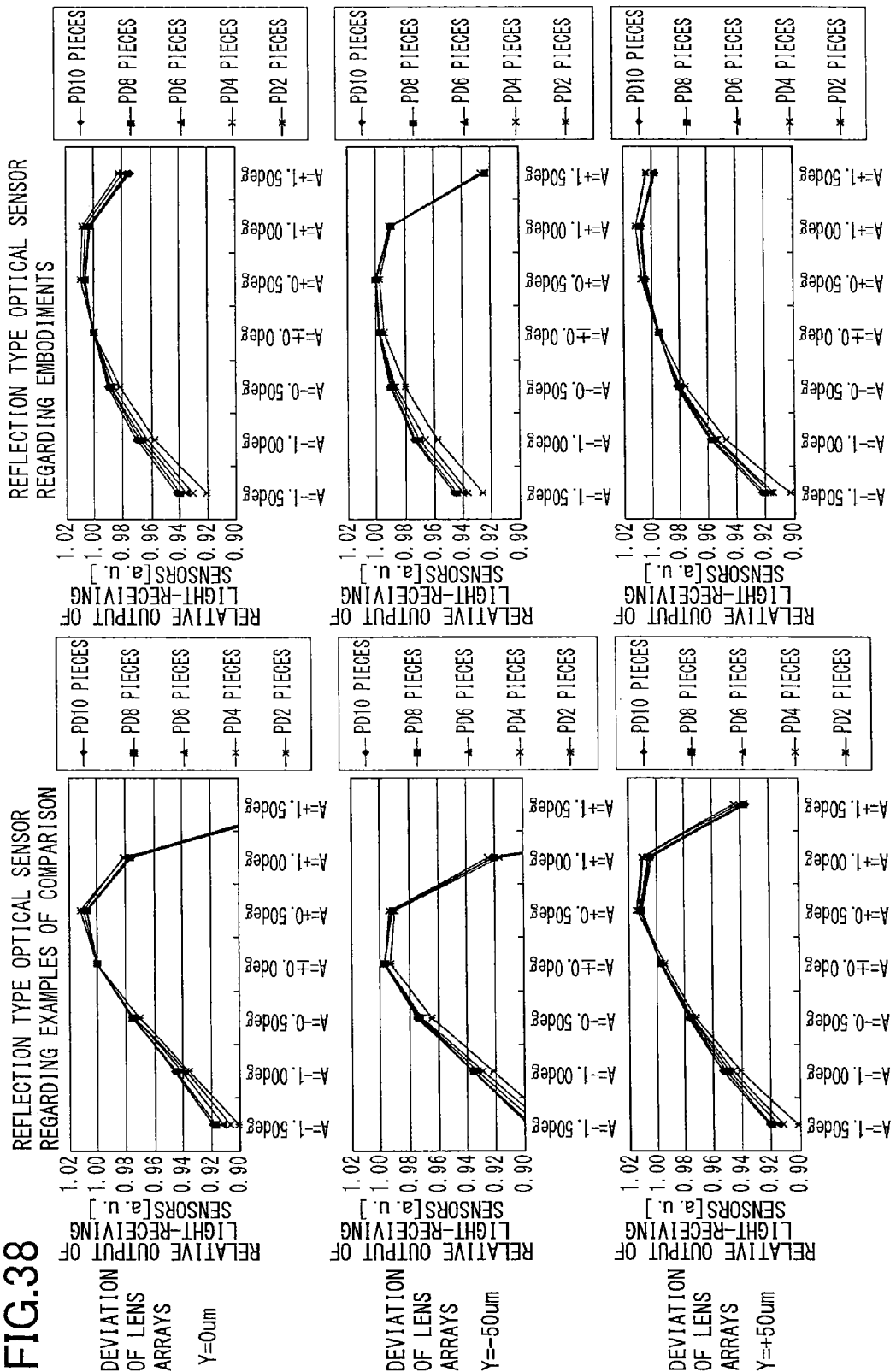

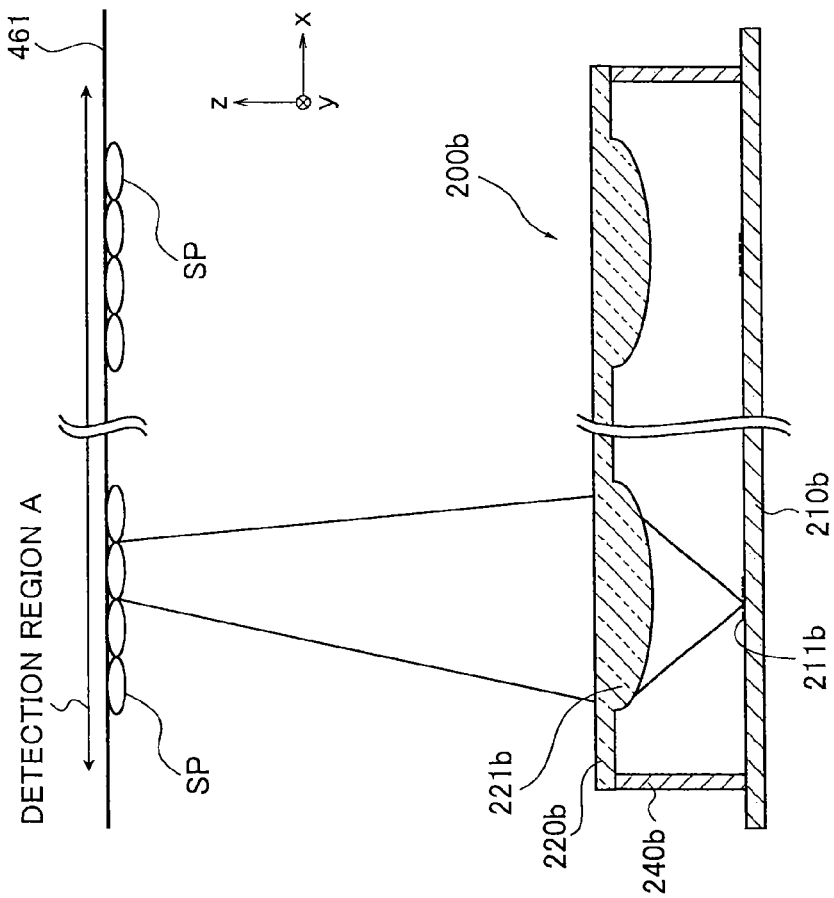
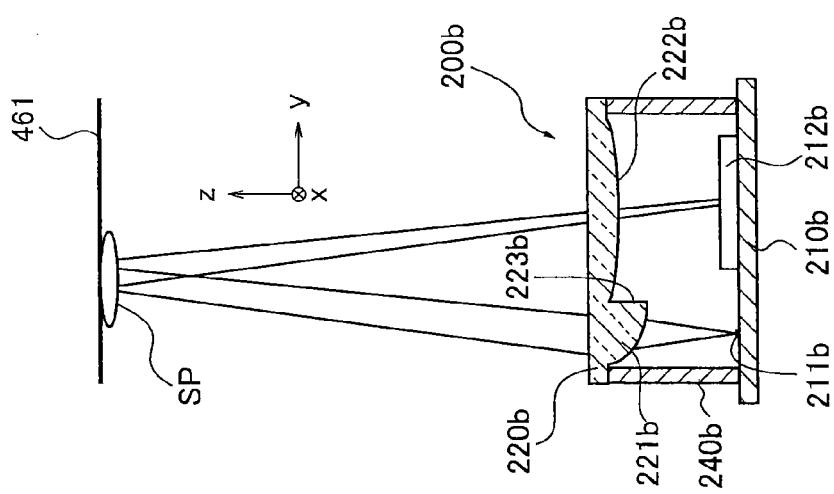

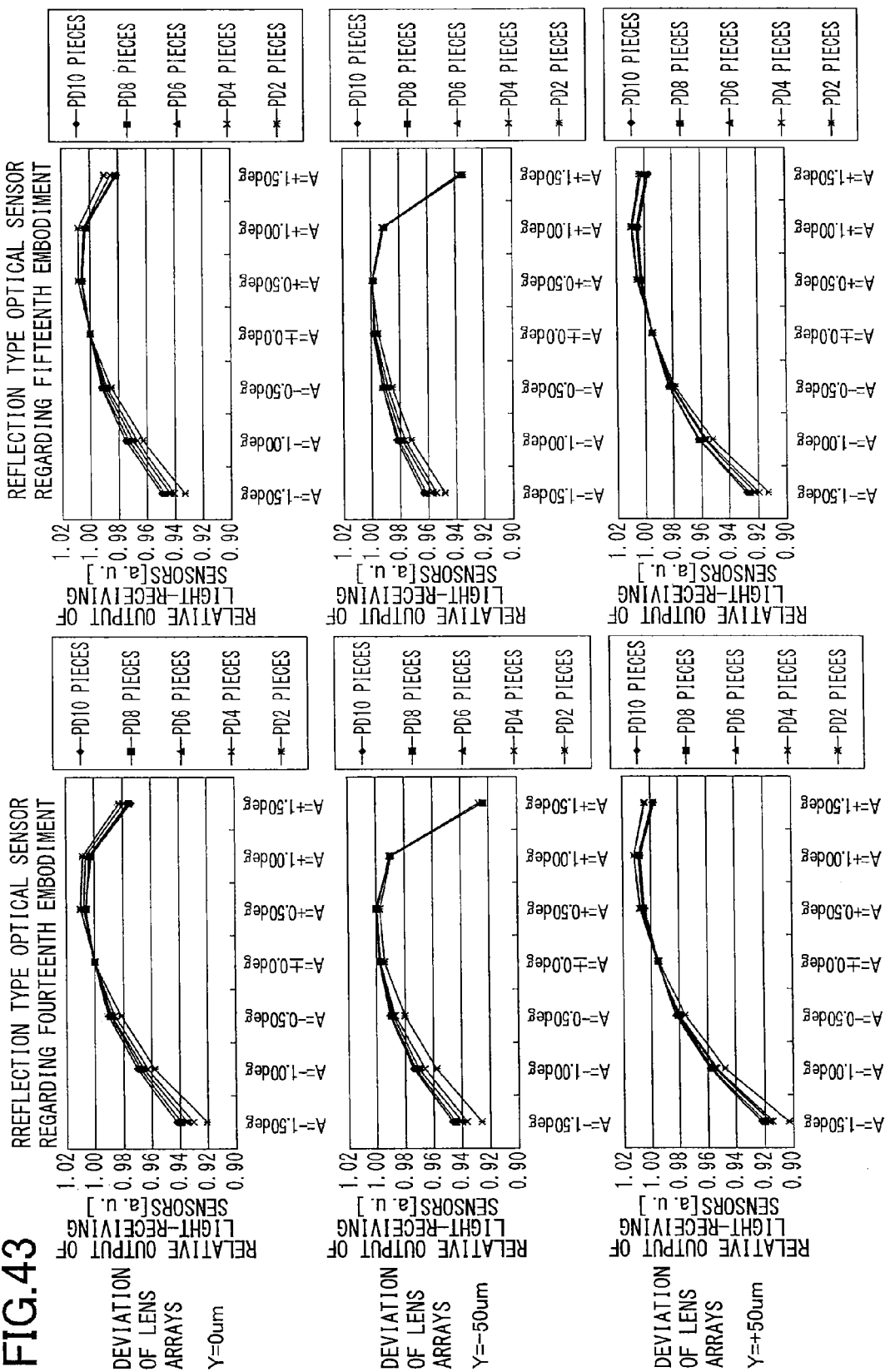

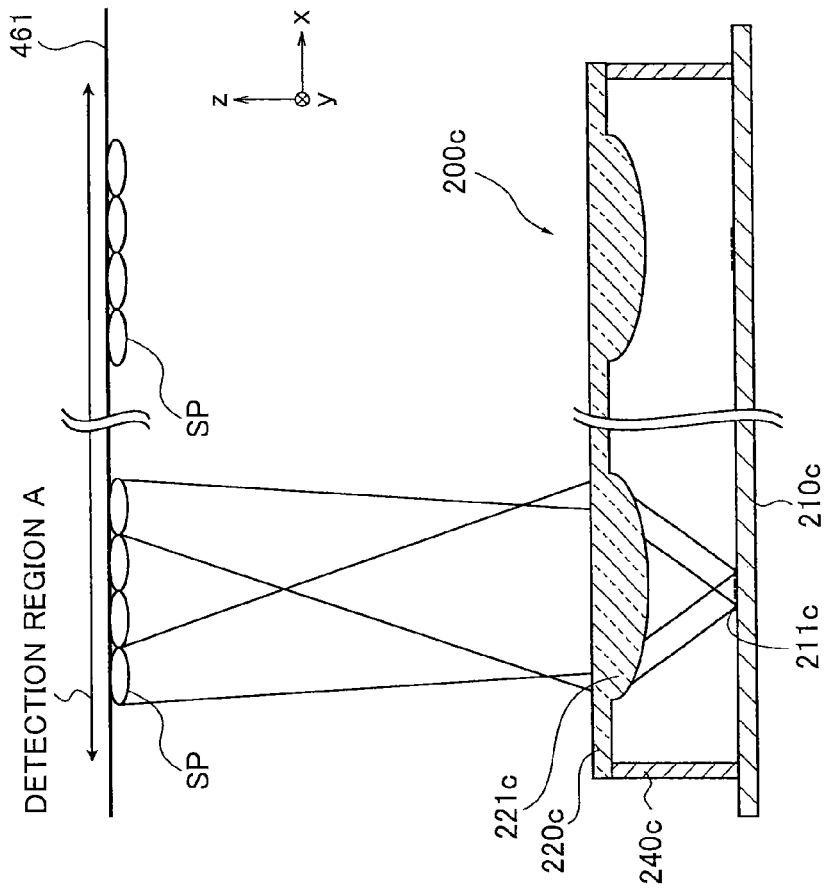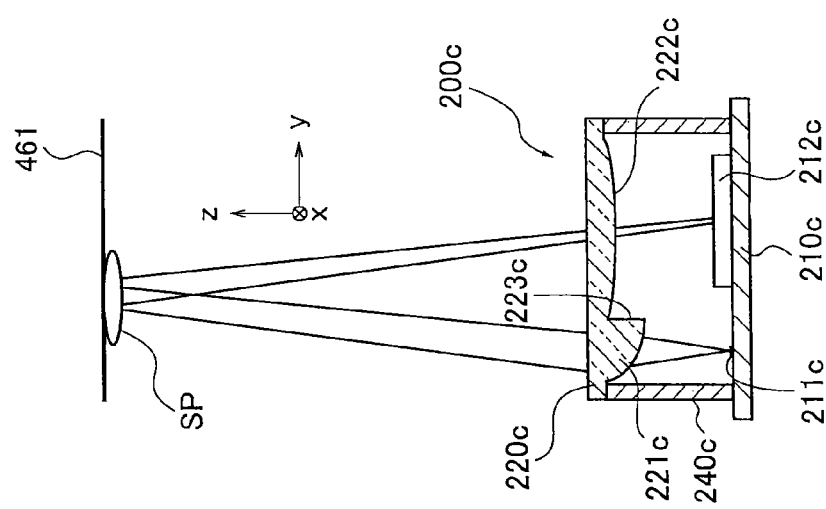

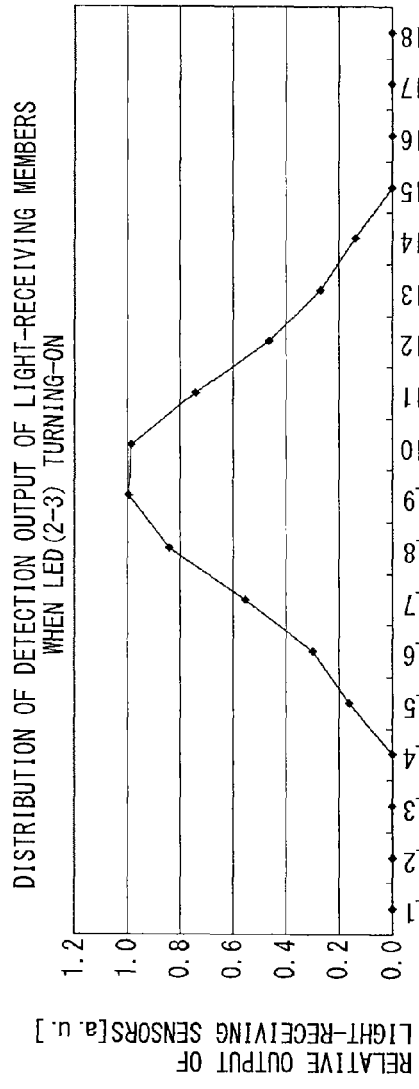
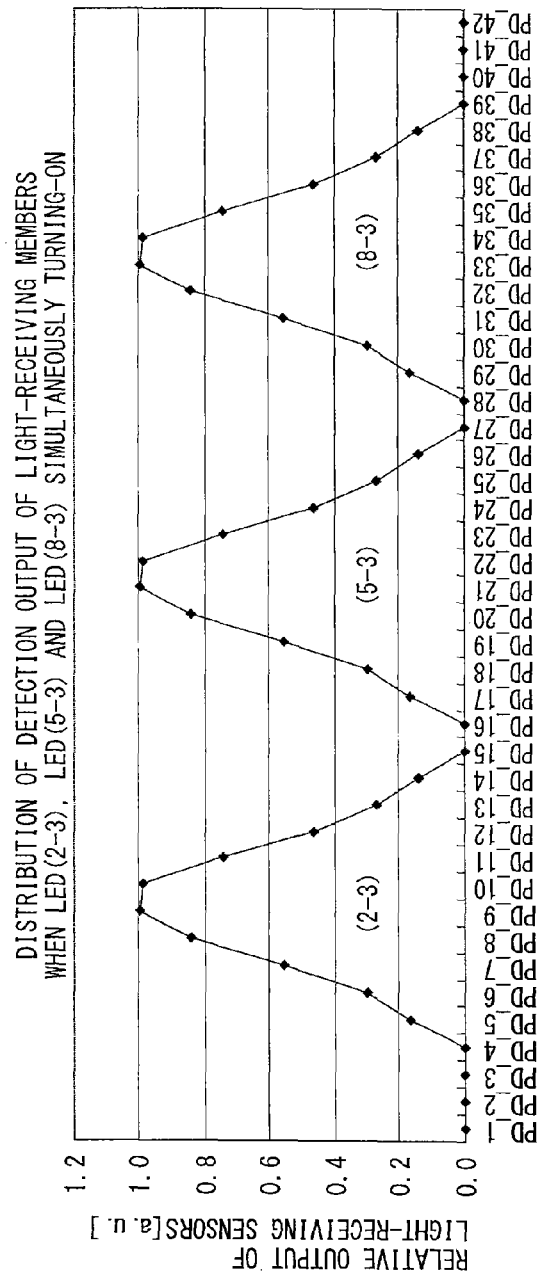
FIG.51A
FIG.51B

REFLECTION TYPE OPTICAL SENSOR AND IMAGE GENERATION APPARATUS

CROSS-REFERENCE TO RELATED APPLICATIONS

The present application is a continuation of U.S. Ser. No. 14/023,032, filed Sep. 10, 2013, which is based on and claims priority from each of Japanese Patent Application Number 2012-199379, filed on Sep. 11, 2012 and Japanese Patent Application Number 2012-204291, filed on Sep. 18, 2012, the disclosure of which is hereby incorporated by reference herein in its entirety.

BACKGROUND OF THE INVENTION

1. Field of the Invention

The present invention relates to an image generation apparatus regarding copy machines, laser beam printers, facsimile terminals and plotter machines.

2. Description of the Related Art

Image generation apparatuses that make color images have been widely used for or applied to color copy machines, printers and facsimile terminals, plotter machines etc. and moreover applied to multi-function printers (MFP), such as those shown in references 1-3. Such image generation apparatus develops images by forming a latent image on the surface of an image carrier holder and transfer developing agent such as toner to the latent image. Next to such development process, the image generation is completed by transferring the developed images onto recording medium such as a piece of paper and fixing the images in a process such that the transferred images are fixed using a fixing member such as fixing belt etc.

In repeating such image fixing process, abrasion and/or scratch are often made on the surface of the fixing member. As a concrete example, carrying out to repeat the fixing process for the A4 size paper laid in the longitudinal direction (that is to pass the paper in the longitudinal direction along the machine) using an image generation apparatus that enables to use copy paper of both A4 and A3 sizes, longitudinal streak scratches are made at the positions, on the surface of the fixing belt, which are the longitudinal peripheries of A4 conventional paper. Such streak scratches are made due to paper debris (such as that of binder or additive) which is divorced from the paper by cutting machine process. The paper debris is attached to both longitudinal peripheries of the paper and abrades the surface of the fixing belt. When a fixing process is carried out using A4 and/or A3 size paper laid in transverse direction (that is to pass the paper in the transverse direction along the machine), a grazing streak comes out to the surface of the images. The appearance of this grazing streak looses the quality of the developed image.

The conventional technologies that may relate to the present invention are found in Japanese Publication of Patent Applications Nos. H5-113739, 2007-34068 and 2006-251165 (called reference 1, reference 2 and reference 3, respectively, hereinafter), all of which are incorporated by reference.

The inventions described in the references 1 to 3 disclose countermeasures that are to prevent such degradation of the image quality. For example, an optical sensor, that detects the reflected light on the surface of a fuser roller to which light is emitted from a light source, is attached to the image generation apparatus described in the reference 1. According to the intensity of the reflected light detected by the optical sensor, the reflectivity of the surface of the fuser roller is calculated. The image generation apparatus generates an alarm when the reflectivity is lower than a predetermined value since the lowering is caused by scratches on the surface of the fuser roller, offset or degradation of a surface condition thereof. People judge the time of exchanging of the fuser roller.

SUMMARY OF THE INVENTION

A first purpose of the present invention is to solve such a problem that, as provided in the reference 1, it has not been possible to decide the existence of the actual scratch or to detect the position or the width thereof since the condition of the surface of the fixing belt is roughly judged by merely calculating the reflectivity thereof and comparing with a predetermined value.

Further to the above purpose, a second purpose of the present invention is to solve the following problem. That is from the following causal relation. An endless fixing belt that is popularly used for the fixing member has problems such that degradation of optical performance or reliability of operation since the optical sensor cannot detect the reflected light that reflected on the fixing belt due to the deviations in the distance from the optical source to the light-illuminated position thereof or the angle of the light-illuminated portion against the optical source due to ruffling, floppy or curling thereof likely happens. Due to such deviations, the optical sensor cannot exactly detect the reflected light from the fixing belt since the light is diffused on the surface of the belt and therefore the optical detection system results into losing reliability. Due to such unreliable capability of optical detection, there is a problem such that an alarm is generated in despite the time to exchange the fixing member has not come yet.

According to the reference 2, an invention of image generation apparatuses such that whole of surface of the fixing members is abraded to prevent such a concentration that the scratches are generated on a particular portion of the resultant image is provided. However, the invention does not disclose the method to detect the generation of scratches or the status of the scratches. According to the reference 3, an invention of image generation apparatuses such that more developer is supplied to the portion where scratches are found than the portion where no scratches are found for the developing process and the scratches can be obscured. As the result, frequent exchange or replacement of parts is not necessary so that it is possible to cut the maintenance costs. However, new technology for the image generation apparatuses is recently required so that precise detection of the scratches and/or the status of the scratched in a quick fashion and maintaining high quality images.

In order to accomplish the first and the second purposes of the present invention, an image generation apparatus that includes the following light-emitting optical system is disclosed. That is a reflection type optical sensor detecting a surface condition of a moving body and being used for an image generation apparatus which forms images on recording media, comprising a light-emitting device which has a plurality of light emitter systems including at least two light-emitting members and a light-emitting optical system having a plurality of light-emitting lenses corresponding to a plurality of the light emitter systems and guiding the light emitted from the light emitter systems to the moving body and a light-receiving device which has a light receiver system including at least two light-receiving members and a light-receiving optical system having light-receiving lenses corresponding to the at least two light-receiving members and guiding light reflected by the moving body to the light receiver system. In other words, the reflection type optical sensor that senses the condition of a moving body, used for an image generation apparatus that forms images on recording media, includes;
1) a light-emitting device having a plurality of light emitter systems that include at least two light-emitting members and a light-emitting optical system that has a plurality of lenses each corresponding to each of the plurality of light emitter systems and guides the light emitted from the emission systems to a moving body, and
2) a light-receiving device having a light receiver system that includes at least two light-receiving members and a light-receiving optical system that has light-receiving lenses corresponding to each of the at least two light-receiving members and guides the reflected light at the moving body to the light receiving system.

BRIEF DESCRIPTION OF THE DRAWINGS

FIG. 11E is a diagram that shows an output variation of the light-receiving member regarding the second embodiment when the light is emitted in a skew angle B of 0 to +/−1.0 degree with 0.25 degrees step using a reflection type optical sensor (LEDa(7)) regarding the second embodiment applied to a fixing belt (a moving body) as a test object.

FIG. 11F is a diagram that shows the output variation of the light-receiving member regarding the third embodiment when the light is emitted in a skew angle B of 0 to +/−1.0 degree with 0.25 degrees step using a reflection type optical sensor (LEDb(7)) regarding the third embodiment applied to a fixing belt (a moving body) as a test object.

FIG. 15B is a diagram that shows distribution of detection output of a plurality of light-receiving members (those from PD_1 to PD_18) when light-emitting members LED(2-3), LED(5-3) and LED(8-3) are simultaneously turned on.

FIG. 23A is a schematic cross-sectional view of the reflection type optical sensor regarding the fourteenth embodiment scanned in the primarily scanning direction for the purpose of explaining a structure thereof.

FIG. 23B is a schematic cross-sectional view of the reflection type optical sensor regarding the fourteenth embodiment scanned in the secondarily scanning direction for the purpose of explaining a structure thereof.

FIG. 38 is a diagram that shows the results of output variation of a PD included in a reflection type optical sensor given in an example for comparison and the fourteenth embodiment.

FIG. 39A is a schematic to explain a structure of the reflection type optical sensor regarding the fifteenth embodiment, specifically a schematic of the cross-sectional view of the reflection type optical sensor regarding fifteenth embodiment scanned in the direction of the primarily scanning direction.

FIG. 39B is a schematic to explain a structure of the reflection type optical sensor regarding the fifteenth embodiment, specifically a schematic cross-sectional view of the reflection type optical sensor regarding fifteenth embodiment scanned in the direction of the secondarily scanning direction.

FIG. 43 is a diagram that shows the results of output variation of a PD included in the reflection type optical sensor regarding the fourteenth and fifteenth embodiments.

FIG. 44A is a schematic to explain a structure of the reflection type optical sensor regarding the sixteenth embodiment, specifically a schematic cross-sectional view of the reflection type optical sensor in the primarily scanning direction.

FIG. 44B is a schematic to explain a structure of the reflection type optical sensor regarding the sixteenth embodiment, specifically a schematic cross-sectional view of the reflection type optical sensor in the secondarily scanning direction.

FIG. 51A is a diagram that shows the result of output variation of a PD included in a reflection type optical sensor regarding the fourteenth with respect to output distribution of a PD when one LED is powered on.

FIG. 51B is a diagram that shows the result of output variation of a PD included in a reflection type optical sensor with respect to output distribution of a PD when three LEDs are simultaneously powered on.

DETAILED DESCRIPTION OF THE PREFERRED EMBODIMENTS

Detailed embodiments to realize the first purpose of the present invention is explained hereinafter in details with reference to the accompanying drawings.

Figure 1:
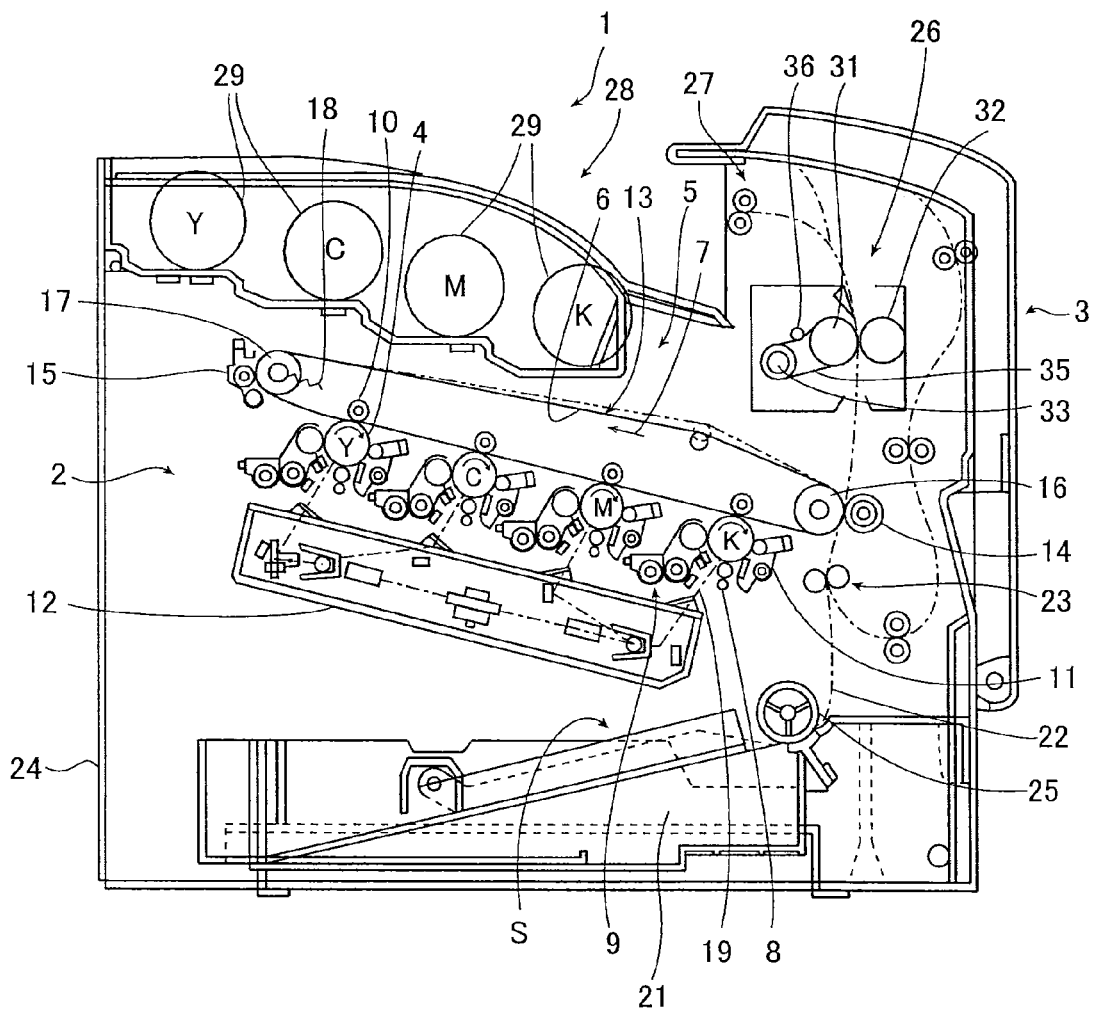
FIG. 1 is a schematic cross-sectional view of a color printer which is an embodiment of an image generation apparatus according to the present invention.

FIG. 1 is a schematic cross-sectional view of a color printer as an embodiment of an image generation apparatus. The image generation apparatus is not limited to color printers but also include copy machines, facsimile terminals, printing machines and complex machines that combine these functions.

In FIG. 1, the image generation apparatus includes an image forming member 2 and a paper feed/eject member 3.

In this apparatus, the image formation member 2 is built in a structure that each visible image formed on a photo receptor drum 4 is superimposed and transferred to an intermediate image transfer member 6 on an image transfer device 5 in a first transferring process and batch-transferred to a recording medium S (such as recording paper, recording materials, recording members etc.) in a secondary transferring process.

The above photo receptor drums 4 are image carrier holders that enable to form images each corresponding to a dispersed color such as a yellow color (Y), a cyan color (C), a magenta color (M) or a black color (K) and that have a tandem structure with four units conformal to such colors. For a convenience to depict a schematic, a part indication number is only given to the photo receptor drum 4 of a yellow color (Y), but those of a cyan color (C), magenta color (M) and a black color (B) are the same as.

The above intermediate image transfer member 6 is an endless belt (referred to as "an image transferring belt", hereinafter) that is opposing to the photo receptor drum 4 and is moveable in the conveying direction 7 shown with an arrow.

The image forming member 2 explained above has several devices in order to image forming processes in accordance to each photo receptor drum 4 corresponding to each color. In order to explain the processes of image forming, the photo receptor drum (K) 4 of the black color, for example, an electrostatic-charging device 8, a developing device 9, a primary transferring roller 10 (referring to a primary transferring roller of a yellow color (Y)) and a cleaning device 11 are placed in such an order. For the purpose of image forming onto the photo receptor drum 4 after electrostatic-charging thereto by using an electrostatic-charging device 8, an optical scanning device 12 (that is a light exposing device) is used as explained later.

Superimpose image transferring to an image transferring belt 6 as explained above is carried out from the upper stream to the downstream in the convey direction 7 with shifting a timing of each image transferring so that each visible image formed on each photo receptor drum 4 of each color as yellow, cyan, magenta and black, is transferred to the same position on the image transferring belt 6 in the process of the image transferring belt moves to the conveying direction. The superimpose image transferring is carried out by applying a voltage to each of primary image transferring rollers 10 which are arranged to oppose to each photo receptor drum 4 across the image transferring belt 6.

Each photo receptor drum 4 explained above is placed from the upper stream to the downstream in the conveying direction 7 as the order of the above explanation. Each of photo receptor drums 4 conform each image station that forms images for each of the colors as yellow, cyan, magenta and black, as well.

The image forming member 2 of the image generation apparatus 1 as explained above further has the four image stations explained above, a secondary image transferring roller 14, a cleaning device 15, an image transferring belt unit 13 opposing upwardly to the each photo receptor drum 4 that constructs each of the imaging station and the optical scanning device 12 as described above which is an optical image forming device opposing downwardly to these four image stations.

The image transferring belt unit 13 includes the image transferring belt 6 explained above and the primary image transferring roller 10. The image transferring belt unit 13 includes a driving roller 16 to which the image transferring belt 6 is coupled and rotated therewith, other than the image transferring belt 6 and the primary image transferring roller 10.

Among these image transferring rollers, a driven roller 17 includes a tension assist device 18 that adds tensile force to the image transferring belt 6 such as a spring that biases to push the driven roller 17 in a direction away from the driving roller 16.

The secondary image transferring roller 14 is an image transferring member that is rotating driven to the image transferring belt 6 and is placed opposing to the image transferring belt 6.

The cleaning device 15 as explained above is to clean the image transferring belt 6 and placed opposing to the image transferring belt 6.

The above image transfer device 5 comprises the image transferring belt unit 13, the primary image transferring roller 10, the secondary image transferring roller 14 and the cleaning device 15.

The above optical scanning device 12 includes semiconductor laser diodes, coupling lenses, f-theta lenses, toroidal lenses, mirrors and rotational polygon mirrors to form electrostatic latent images on the photo receptor drums 4 in such a manner that image forming lights 19 each corresponding to each of colors is emitted to each corresponding photo receptor drums 4.

The cleaning device 15, not depicted in FIG. 1 for the simplicity, installed to above image transfer device 5 includes a cleaning brush and a cleaning blade which are set to oppose the image transferring belt 6 and contact thereto, cleaning the image transferring belt 6 by scanning and removing foreign materials such as residual toner etc. on the surface of the image transferring belt 6. The cleaning device 15 also includes an eject device, not depicted in FIG. 1 for a simplicity, to carry the residual toner removed from the image transferring belt 6 out thereof for exhausting.

The above paper feed/eject member included in the image generation apparatus 1 has a sheet container 21 that stores recording media S (whose position is only shown in the figure) such as blanks vertically piled therein, a pair of resist rollers 23 that bring up the recording medium conveyed along a blank conveying pathway 22 from the sheet container 21 toward an image station locating between a photo receptor drum 4 and an image transferring belt 6 at the timing to meet that of toner image forming by means of above image station and a sensor (not shown in FIG. 1) that detects the arrival of the front edge (or front periphery) of the recording medium S at the pair of the resist roller 23.

The sheet container 21 explained above is embodied by a paper feeding cassette that is set under the main body of the image generation apparatus 1. The feeding cassette has a convey roller 25 working as a feeding roller that contacts the upper surface of the top of the recording media S piled therein. The convey roller 25 conveys the top sheet of the recording media S to the above pair of resist roller 23 by being driven to rotate in counter clockwise in FIG. 1.

Moreover, the paper feed/eject member 3 has a fixing device 26 working as a fixing unit to fix toner on the recording media S to which a toner image is transferred, a paper ejecting roller 27 that discharges the recording media S, already being processed for fixing the toner, out of the main body 24 of the image generation apparatus 1 and a paper ejecting tray 28 that is formed outside of the main body 24 and piles the recording media S discharged out from the main body 24 by the paper ejecting roller 27.

A belt-fixing device is used for the fixing device 26 explained above.

Toner bottles 29, each for a yellow color, a cyan color, a magenta color and black color, are installed in a space of the lower part of the paper ejecting tray 28.

The image generation apparatus 1 depicted in FIG. 1 batch-transfers the images, which are formed by each photo receptor drum 4 into a superimposed color image by transferring each by each, to the recording media S by using a secondary image transferring roller 14. As another system, it is possible to directly superimpose all color images onto the recording media S each corresponding to each photo receptor drum 4.

Figure 2:
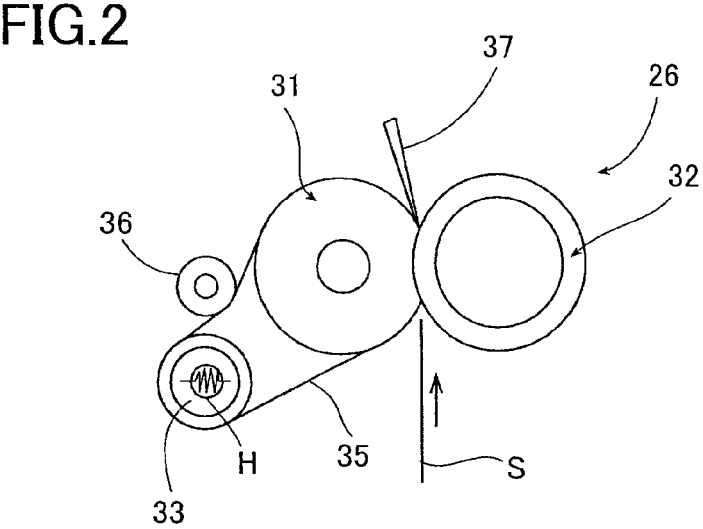
FIG. 2 is a schematic magnified side view of fixing members of the image generation apparatus shown in FIG. 1.

FIG. 2 is a schematic of a magnified side view of the construction of the fixing device 26 explained above.

The fixing device 26 has a fuser roller 31, a pressing roller 32 that applies a pressure against the fuser roller 31, a heating roller 33 which has a thermal source H therein and a fixing member (or called a fixer) such as a fixing belt 35 working as a moving body and being engaged to both the heating roller 33 and the fuser roller 31 which rotate therewith.

In addition, the fixing device 26 has a tension roller 36 which further provides tension to the fixing belt 35, a separation click 37 set at the downstream of the conveying direction of the recording media S and a temperature sensor (not shown in FIG. 2) that senses the temperature of the fixing belt 35 locating above the heating roller 33.

The fuser roller 31 explained above is a composite member such that silicone rubber covers a metal rod thereon.

The pressing roller 32 consists of a metal rod made of aluminum, iron etc. covered with an elastic layer such as silicon rubber cover thereon and a peel ply such as a layer or PFA (a trade mark of perfluoroalkoxy) or PTFE (a trademark of polytetrafluoroethylene) formed further thereon.

The heating roller 33 mentioned above is made from a hollow pipe of aluminum or iron and a thermal source such as halogen heater is installed therein.

The fixing belt 35 is a base material made of nickel or polyimide with a peel ply such as a surface layer of PFA or PTFE formed further thereon or that has further an intermediate elastic layer of silicon rubber between the base material and the surface layer. The fixing belt 35 is engaged to both the fuser roller 31 and the heating roller 33 which rotate therewith and keeps appropriate tension by externally pushing with the tension roller 36.

The separation click 37 explained above contacts to the surface of the fuser roller 31 of the fixing belt 35 at the front edge (atop) and a plurality thereof is arranged in the width direction (vertical to the page of paper) of the fixing belt 35.

The temperature sensor explained above does not contact to the fixing belt 35 but a non-contacting temperature sensor (that is a thermopile) is only set thereto. Instead of such temperature sensor, it is possible to use a contacting temperature sensor (that is a thermistor).

The tension roller 36 explained above is a metal rod covered with silicon rubber.

The fixing device 26 that is composed with these materials and members fixe images on the recording media S by applying a pre-determined pressure and heat at a nipping part when the recording media S come from portions shown in bellow in the schematic of FIG. 2 toward the nipping portion being formed with the fuser roller 31 (or the fixing belt 35 and the pressing roller 32) and enabling to hold and convey.

Figure 3:
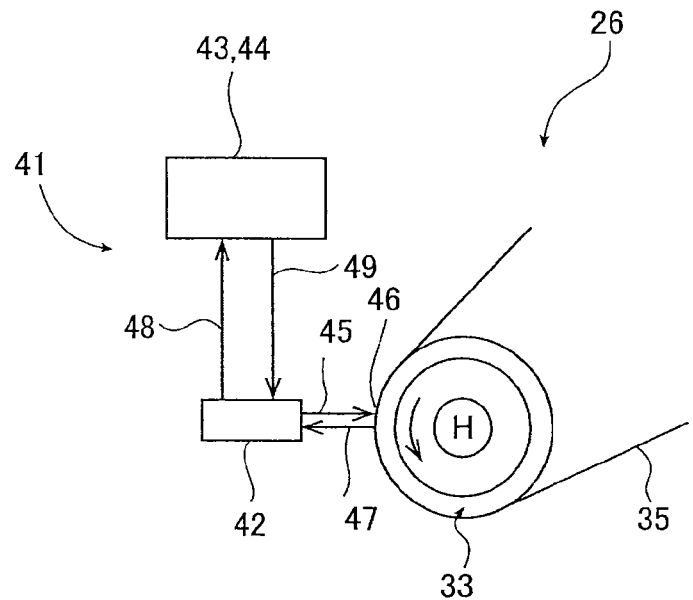
FIG. 3 is a schematic whole view of a surface detection device according to the present invention.

A surface condition detection device 41 is attached to the fixing devices 36 as shown in FIG. 3. Such surface condition detection device 41 is to detect the surface condition of the moving body (that is a fixing member).

The surface condition detection device 41 comprises a reflection type optical sensor 42 and a surface condition judging device 43.

The reflection type optical sensor 42 as mentioned above is placed in an arrangement to oppose to the fixing belt 35 at the portion of the heating roller 33 in the fixing belt 35 (a moving body) and be constructed to be such an detection system that receives the reflected light 47 each coming from a plurality of optical spots 46 each on the different position in the direction of the width on the fixing belt 35 by emitting the light beam 45 (or detection light) thereto.

The surface condition judging device 43 is placed in the image generation apparatus 1 and connected to the reflection type optical sensor 42 so that the surface condition judging device 43 can judge the surface condition of the fixing bet 35 by carrying out various signal processing with the detected signal 48 sent from the reflection type optical sensors 42. The surface condition judging device 43 also has a function to work as a controller 44 to control the reflection type optical sensor 42 by sending a control signal 49 thereto.

Figure 4:
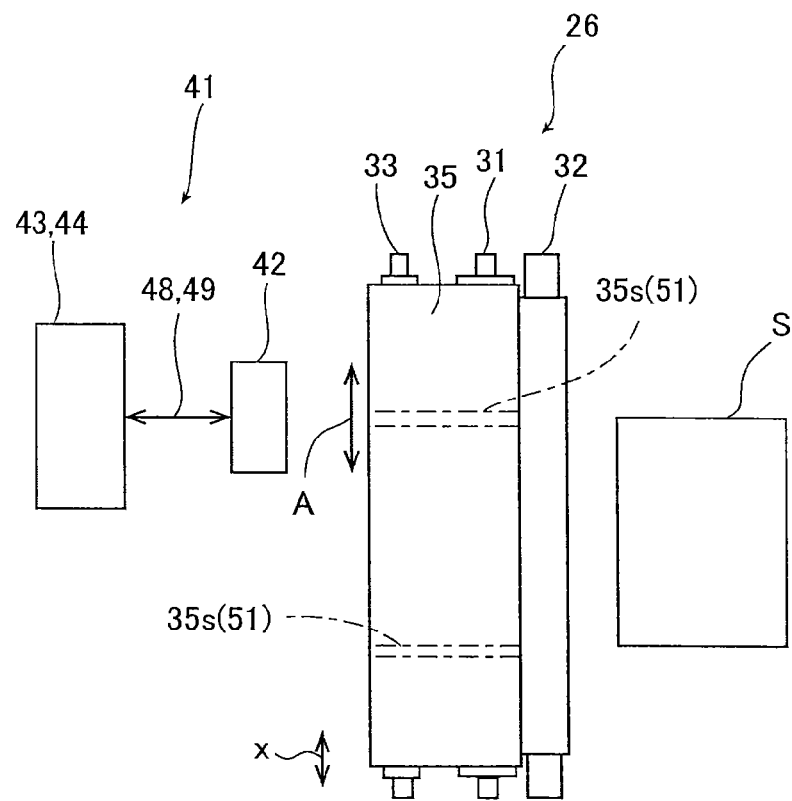
FIG. 4 is a schematic view of a surface condition sensing device in a direction vertical to the rotational axis of the heating roller.

FIG. 4 is a schematic view of the surface condition detection device shown in FIG. 3 in the direction vertical to the rotational axis of the heating roller 33 (that is, downwardly from the upper space of FIG. 3).

In this arrangement, only one reflection type optical sensor 42 is, for example, when an A4 blanks is used in the longitudinal-laid direction, placed for the width direction x of the fixing belt 35 that is an periphery position 35s which is the side of recording media S in the passing direction or nearby thereof.

The reflection type optical sensor 42, as discussed later in details, forms a rather long detection region A on the surface of the fixing belt 35 by emitting a plurality of optical spot 46 sequentially generated in the direct position along the width direction x. Forming such rather long detection region A, the relative positional relation between the reflection type optical sensor 42 and the width periphery portion 35s of the recording media S can be acceptable even for the case that the relative positional relation is not precise.

The surface condition judging device 43 can detects a surface condition of the fixing belt 35 in a range of rather long detection region A in the direction of the width direction x thereof by inputting the detection signal 48 from the reflection type optical sensor 42.

The periphery of the recording media S being included in the detection region A, the existence, position, level etc. of scratches 51 which have a shape of longitudinal streak scratches can be quantified.

The level of the scratches 51 literally implies the degree of scratches such that the depth (or surface roughness) and the width (or size) etc. thereof.

Before explaining concrete embodiments of the presentation inventions, featuring the structures, the functions and the effects of these embodiments are explained in the following paragraphs.

The following embodiments relate to the reflection type optical sensor 42 that detects a surface condition of a moving body (which is a fixing belt as discussed later) used for the image generation apparatus 1 forming images on recording media.

As shown in FIGS. 10A to 10D, the reflection type optical sensor 42 comprise a plurality of light emitter systems having at least two light-emitting members 52, a plurality of light-emitting lenses 58 corresponding to a plurality of the light emitter systems, a light-emitting optical system that guides the light beam 45 emitted from the light emitter systems to the moving body and a light-receiving optical system 56 (referring to FIG. 5A) that, having light-receiving lenses 61 corresponding to the light-receiving members 55, guides the reflected light 47 reflected by the moving body to the light receiver system.

The part indication numbers for the light-emitting optical system 53 and the light receiving optical system 56 are presented in the embodiments shown in FIGS. 5A to 5D. For the purpose of the simplicity, these numbers are omitted for such systems in the other figures, however they are still these part indication numbers are consistently same for the systems.

Since it is possible to further specifically detect, in real-time and in details, the surface condition of the moving body in the position of the width direction thereof by comparing the reflected light 47 that is the light beam 45 each received the at least two light-receiving member 55, it becomes possible to precisely detect the surface condition. For example, it is possible to detect precise condition such as the existing of actual scratches 51 on the moving body and the position, depth and width thereof.

When a plurality of light-emitting members 52 is set in the light-emitting optical system 53, it is possible to improve the precision in detecting the surface condition of the moving body as well as optimize the design of the light-emitting portion 54 and the detecting portion 57 since the light-emitting optical system 53 that has large diameter lenses are used for the plurality of light-emitting member 52 can increase the intensity of the reflected light 47 from the optical spot 46 with maintaining the pitch (or the arrangement pitch) of a plurality of the optical spots 46 in comparison to the case when a plurality of light-emitting optical systems 53 that have small diameter lenses are used.

It is preferably to arrange each light-receiving members 55 explained above in such a way that, regarding the array direction of arrangement (that is the width direction x of the moving body), the optical axis position of a plurality of the light-emitting lenses 58 each corresponding to the light emitter systems as explained above is set at the position between arbitral two light-receiving members 55 among each light-receiving member 55 above explained or near to such two light-receiving members 55.

The output variation of the light-receiving member 55 caused by the fluctuation of the rotation angle (that is a skew angle) around the conveying direction of the moving body (as of the recording medium S) each light-receiving member 55 can be suppressed and stabilized by the optical axis position of a plurality of the light-emitting lens 58 each corresponding to the light emitter systems as explained above being set at the position between arbitral two light-receiving members 55 among the each light-receiving member 55 above explained or near to such two light-receiving members 55 regarding the array direction of arrangement (that is the width direction X of the moving body). Since the light-receiving member 55 becomes to have a similar behavior against the skew angle in such setting, it is possible to decrease the detection error in accordance to the suppression or stabilization of the output variation.

As shown in FIGS. 12A to 12D, cylindrical lenses 62 that convert the light (the reflected lights 47) in a single axial direction can be used for the light-receiving lenses 61.

By using the cylindrical lenses 61 that convert the light (the reflected lights 47) in a single axial direction, it is possible to suppress the variation of the receiving light distribution obtained by detecting portion 57 (against the width direction x of the moving body) in comparison to the use of spherical lenses for the light-receiving lenses 61.

By using the cylindrical lenses 62 for the light-receiving lenses 61, it is possible to more precisely detect the surface condition of the moving body since variation of the parameters (for example, the curvature radius, the set position, the thickness of the lens) of each lens (that is the small lens) can be removed.

As shown in FIGS. 13A to 13D, the light-emitting lenses 58 that composes the light-emitting optical system 53 and the light-receiving lenses 61 that compose the light-receiving optical system 56 are preferably formed in a integrated manor to form a lens array 63.

By forming the light-emitting lens 58 and the light-receiving lenses 61 into a single element, the precision of the physical arrangement of each lens against each other can be improved as well as improvement of the workability to assemble each lens (such as each the light-emitting lenses 58 and the light-receiving lenses 61), that is, for example, to assemble a plurality of lenses each by each.

As shown in FIGS. 14A to 14D, it is preferred to place a light-blocking member 65 between the light-emitter system explained above and the light-emitting optical system 53.

As setting the light-blocking member 65 between the light emitter system explained above and the light-emitting optical system 53, it is possible to more precisely detect the surface condition of the moving condition by reducing the detection or preventing to detection of the reflected light 47 from the portion other than the optical spot 46 the reflected light 47 reflected at the lens surface of other light-emitting lens 58 that does not correspond to the light-emitting member 52 that emits the light at the light-receiving members 52.

It is preferred to expose a plurality of optical spots 46 in series to the light.

By generating a plurality of the optical spots 46 in series by light emission, only one spot 46 is generated at a time and the reflected light 47 coming from a plurality of spots is not simultaneously at the same light-receiving position so that the precision of the detection of the reflected light 47 from each optical spot 47 can be improved.

Figure 15A:
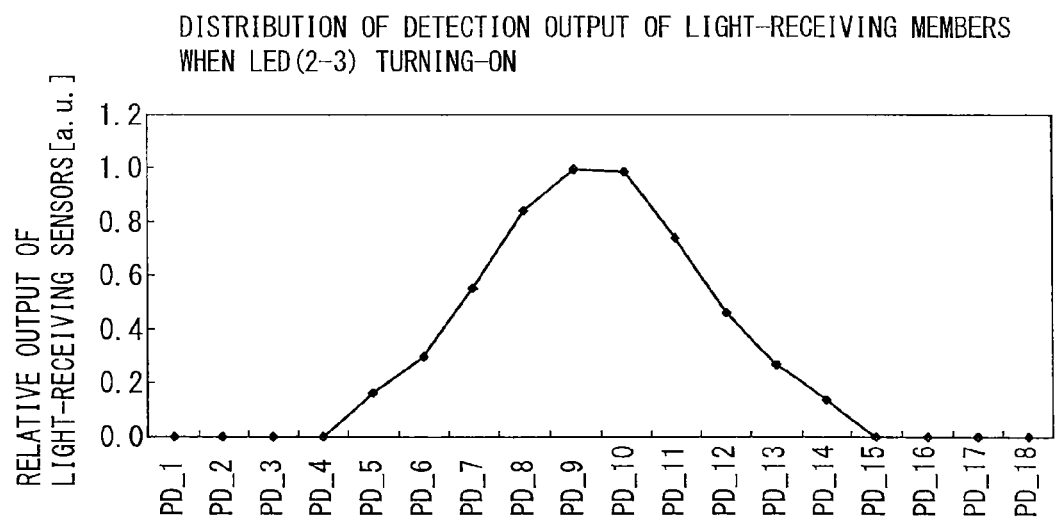
FIG. 15A is a diagram that shows distribution of detection output of a plurality of light-receiving members (those called PD_1 to PD_18) when light-emitting member LED(2-3) turns on, where PD and LED are the abbreviations implying of "photo diode" and "light-emitting diode", respectively.
Figure 15B:
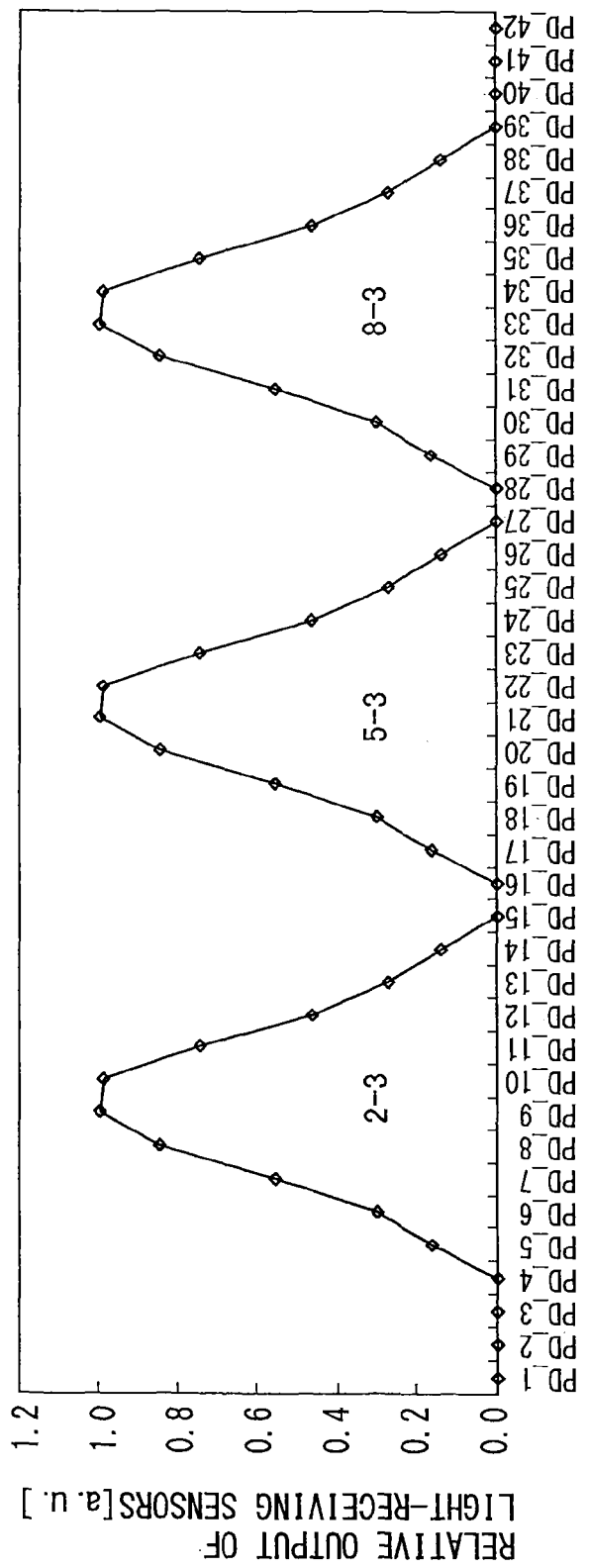

It is further preferred to simultaneously generate a plurality of the optical spots 46 by the light emission (referring to FIGS. 15A and 15B).

By simultaneously generating a plurality of the optical spots 46 to the light, it is possible to detect the surface condition of the moving body quicker and more precise fashion since the scanning cycle of the optical spot 46 in the width direction x of the moving body can be shortened in comparison to exposing a plurality of the optical spots 46 in series to the light.

Figure 16A:
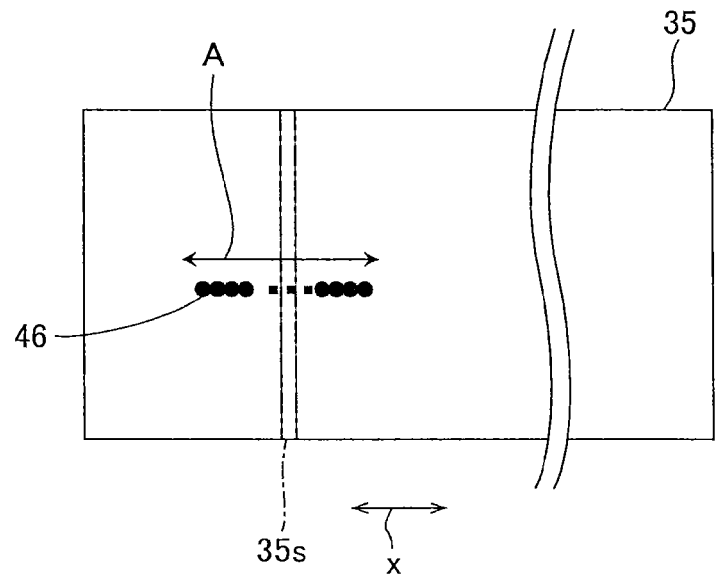
FIG. 16A is a schematic front view of the reflection type optical sensor aligned in the width direction observed in the vertical direction right to fixing belt.
Figure 16B:
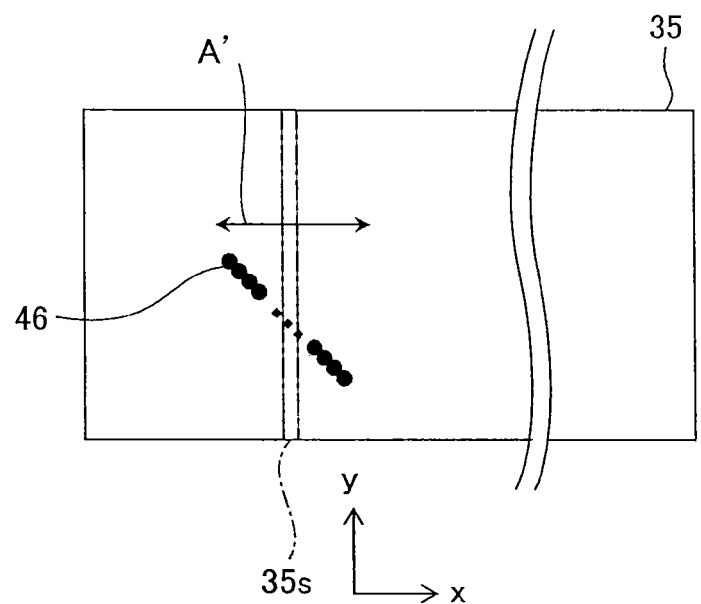
FIG. 16B is a schematic view of the reflection type optical sensor regarding the ninth embodiment aligned with a tilt angle to width direction and moving direction from the direction of planar direction of the fixing belt.

As shown in FIG. 16B, it is preferred to generating a plurality of the optical spots 46 with arbitral angle against the array direction of arrangement (that is the width direction of the moving body) of a plurality of the light emitter systems.

By generating a plurality of the optical spots 46 with arbitral angle against the array direction of arrangement (that is the width direction x of the moving body) of a plurality of the light emitter systems, even for the case that a plurality of the light-emitting members 52 are, for example, placed with a certain interval distance, the separation distance in the width direction x of a plurality of the optical spots 46 can be smaller than the above certain interval distance and the position resolution can be easily improved.

As the reflection type optical sensor 42, it is preferred to use the reflection type optical sensor 42 in the image generation apparatus 1.

Even in such use of the reflection type optical sensor 42, the image generation apparatus 1 has the same functional effects.

Figure 17A:
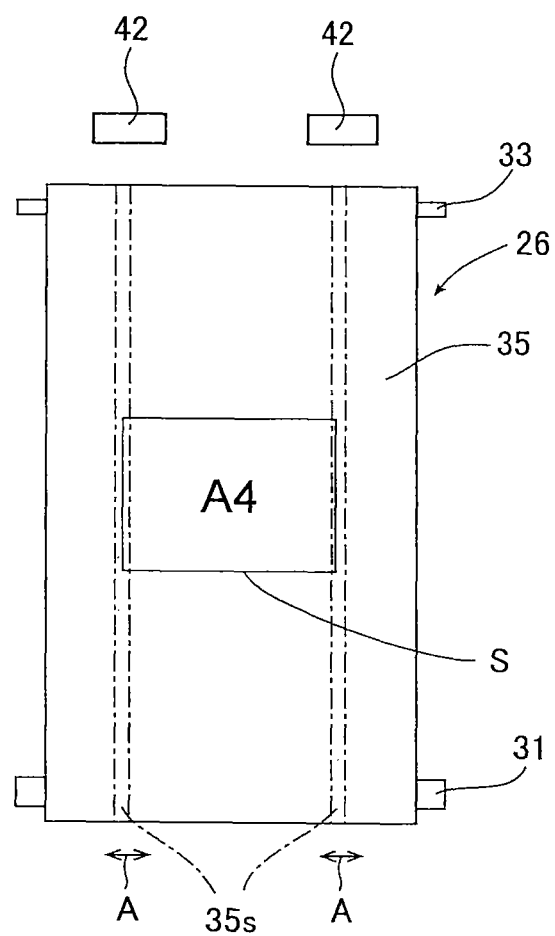
FIG. 17A is a schematic that shows the alignment of reflection type optical sensor regarding the eleventh embodiment against the location of width periphery of recording media (such as A4 etc. blanks) regarding the eleventh embodiment in a view of a fixing belt.
Figure 17B:
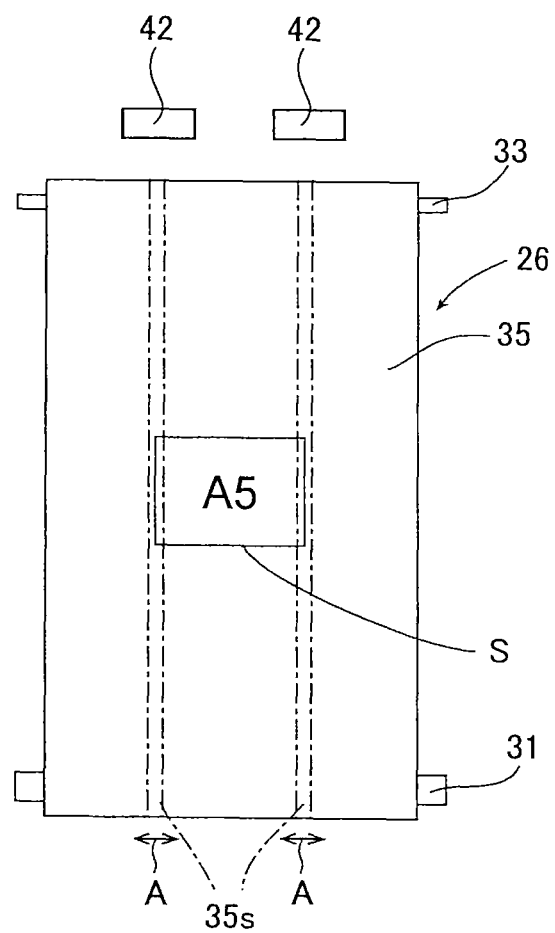
FIG. 17B is a schematic that shows the alignment of reflection type optical sensor regarding the eleventh embodiment against the location of width periphery of recording media (such as A5 etc. blanks) regarding the eleventh embodiment in a view of a fixing belt.
Figure 17C:
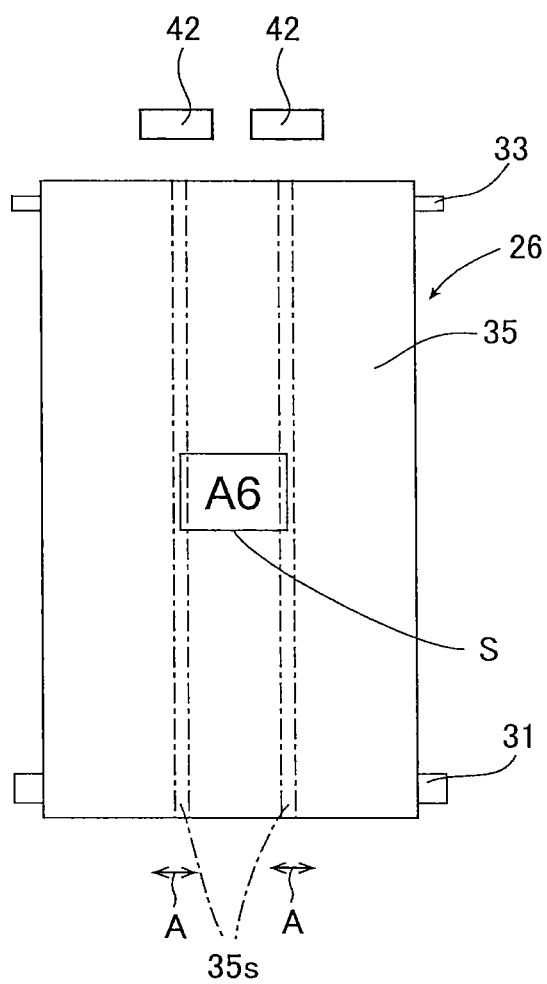
FIG. 17C is a schematic that shows the alignment of reflection type optical sensor regarding the eleventh embodiment against the location of width periphery of recording media (such as A6 etc. blanks) regarding the eleventh embodiment in a view of a fixing belt.
Figure 18:
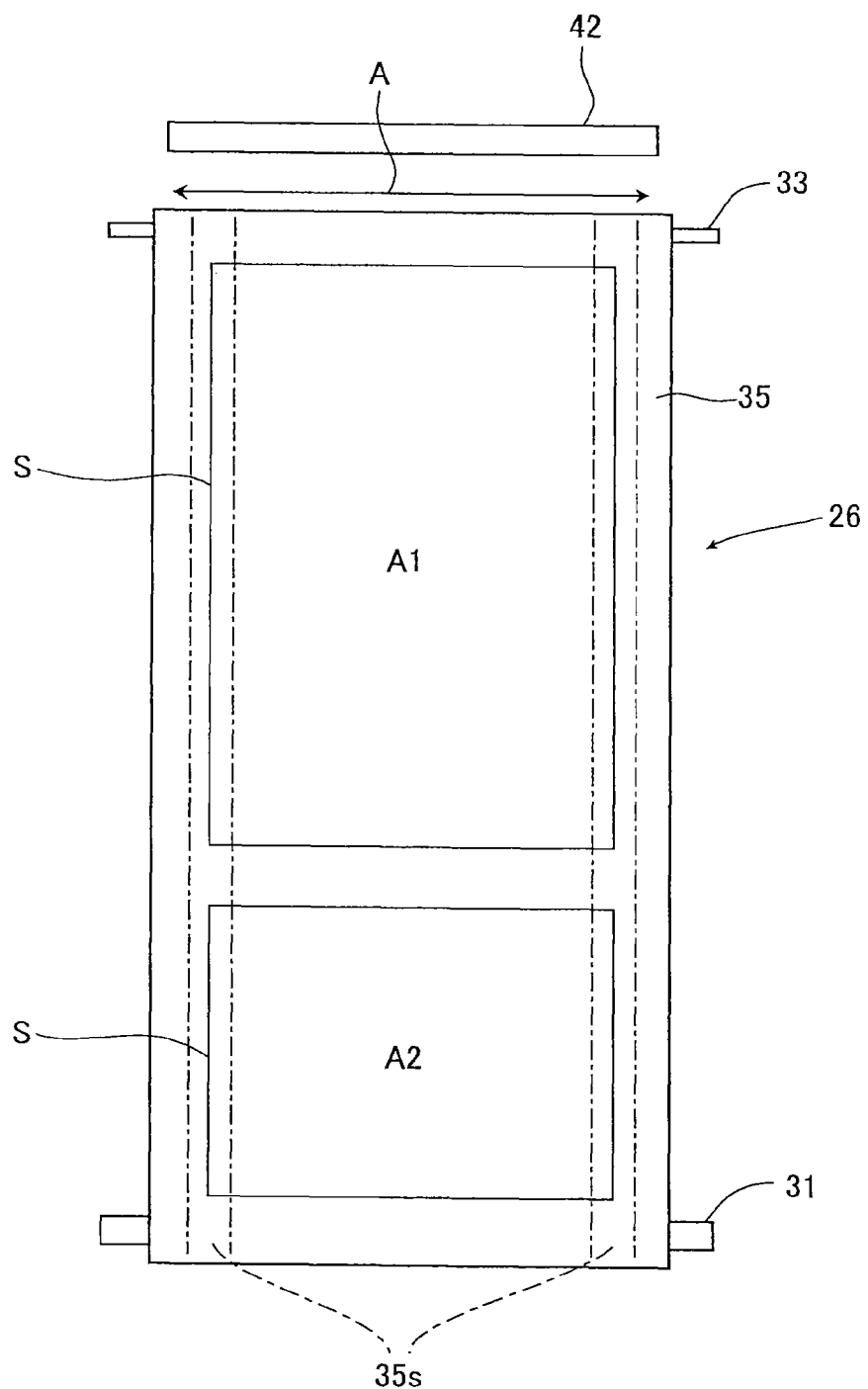
FIG. 18 is a schematic that shows the status of the reflection type optical sensor (regarding the twelfth embodiment) extending to whole width of fixing belt in the surface direction.

For the image generation apparatus 1 explained above, it is preferred to partially place the reflection type optical sensor 42 at or nearby the edge of the recording medium S that the moving body conveys as shown in FIGS. 17A to 17C or over total width of the recording medium S as shown in FIG. 18.

By partially placing the reflection type optical sensor 42 at or nearby the width periphery position 35*s* of the recording medium S that the moving body conveys, it is possible to make the reflection type optical sensor 42 into a small dimension as well as to effectively place the reflection type optical sensor 42 at or nearby the place where the moving body mostly suffers from scratches 51.

In such arrangement of the reflection type optical sensor 42, the setting place of the reflection type optical sensor 42 can be at or nearby the position of at least one of the width periphery position 35*s* of one of the recording medium S among those which have equal to or smaller than the largest size of the recording media S conveyable by the moving body. In the view of practice, it is preferable that the placing position of the refection type optical sensor 42 at or nearby at least one of the width periphery positions 35*s* of at least of one of the smaller size recording media S but excluding the largest size of the recording medium S conveyable by the moving body.

By arranging the reflection type optical sensor 42 over the whole width of the moving body, it is possible to simultaneously detect in one time a plurality of kinds of the scratches 51 that are created at the different places of the recording media 5, being conveyed by the moving body, due to the size thereof so that no miss-detection happens.

The moving body used in the image generation apparatus 1 can be a fixing belt 35 (referring to FIGS. 2 to 4).

The moving body being the fixing belt 35, it is possible to surely detect the surface condition of the fixing belt 35 since a material (such as PFA pulverized fuel ash) is used and the fixing belt can easily get scratches 51.

Fuser rollers 31 can be used instead of the fixing belt 35 for the moving body.

Concrete embodiments regarding the present invention are described in relation to the above discussion.

The First Embodiment

FIGS. 5A to 5D show the most fundamental structure of the reflection type optical sensors 42.

The definition of the direction is generally that the width direction x of the moving body (or the fixing body such as the fixing belt 35) is the principal direction (or the principal scanning direction), the moving direction y (or the tangential direction thereof) of the emitting portion of the optical spots 46 on the moving body (or the fixing member) the secondary scanning direction (or the secondary scanning direction) and separation direction between the moving body (or the fixing member) and the reflection type optical sensor 42 emitting direction of the light beam 45 or the reflection direction of the reflected light 47.

Figure 5A:
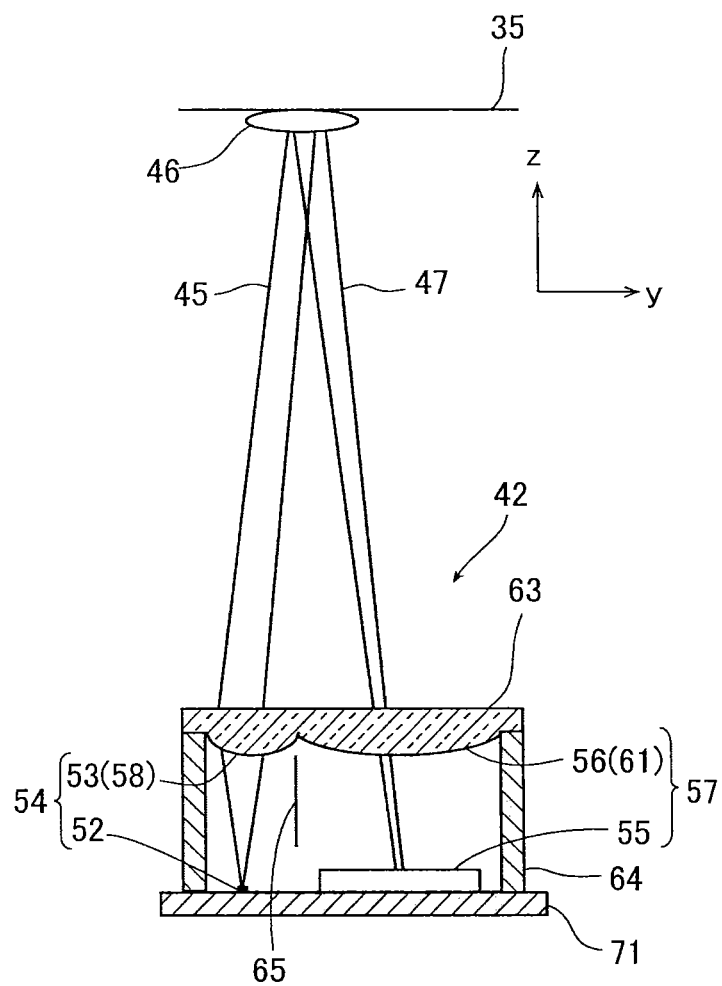
FIG. 5A is a schematic side view of the reflection type optical sensor regarding the first embodiment in a direction of width thereof.

FIG. 5A is a schematic side view of the reflection type optical sensor 42 in a width direction x.

Figure 5B:
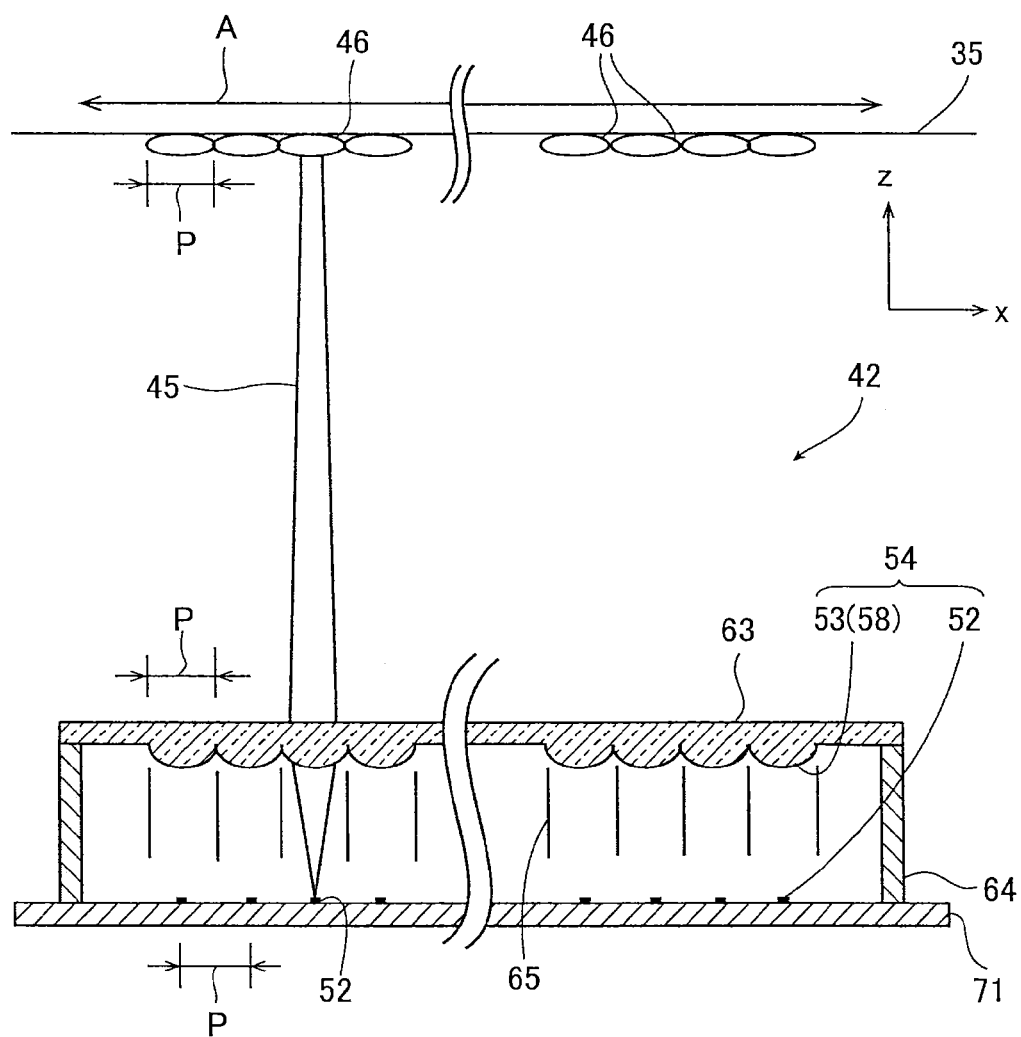
FIG. 5B is a schematic front view of the reflection type optical sensor shown in FIG. 5A from light-emitting member in a moving direction.

FIG. 5B is a schematic front view of the reflection type optical sensor 42 shown in FIG. 5A seen from the light-emitting member 52 in the above moving direction y.

Figure 5C:
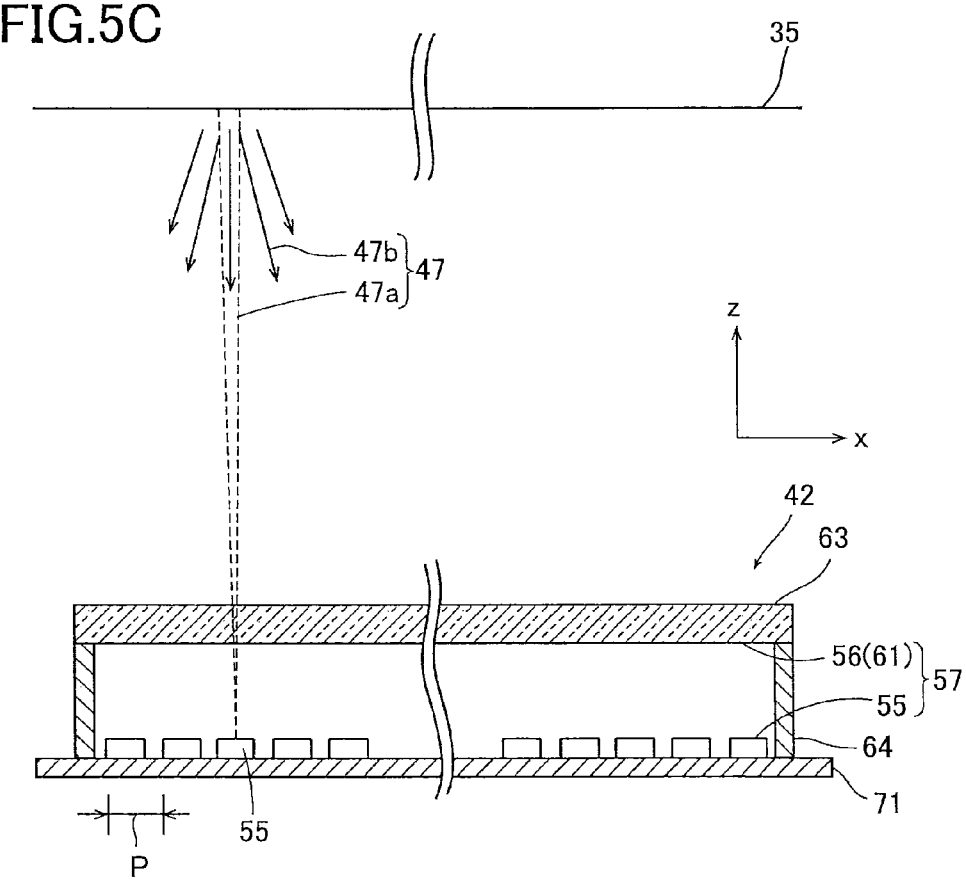
FIG. 5C is a schematic back view of the reflection type optical sensor shown in FIG. 5A from the light-receiving members.

FIG. 5C is a schematic back view of the reflection type optical sensor 42 shown in FIG. 5A seen from the light-receiving members 55 in the direction of the moving direction.

Figure 5D:
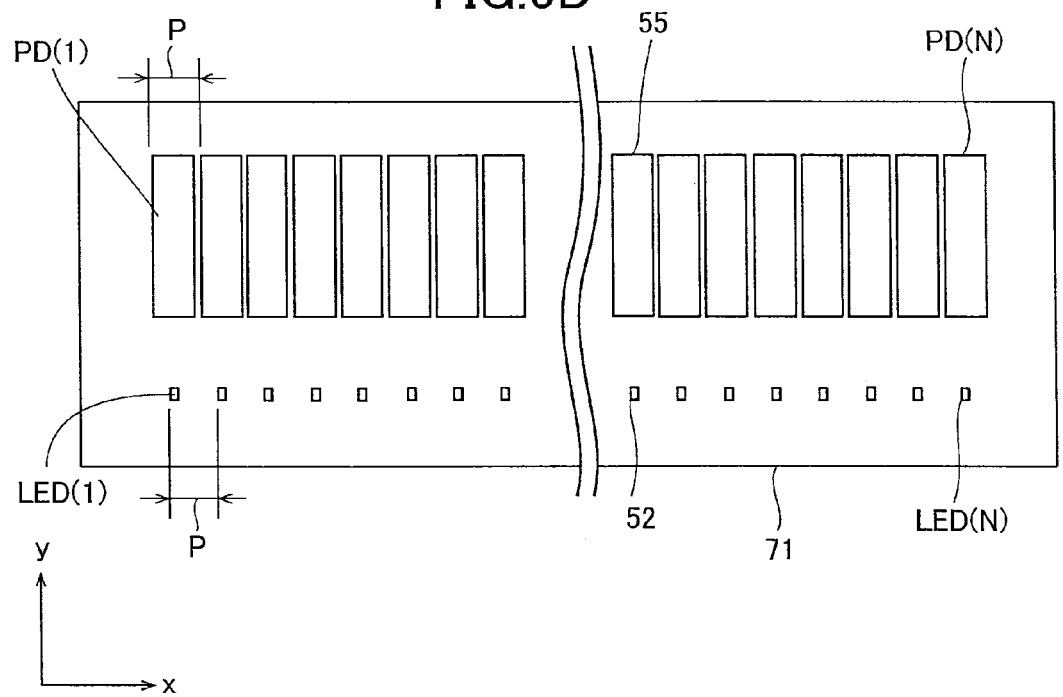
FIG. 5D is a schematic plan view of a board that supports the light-emitting members and the light-receiving member included in the reflection type optical sensor shown in FIG. 5A in the separating direction.

FIG. 5D is a schematic plan view of the board 71 that supports the light-emitting members 52 and the light-receiving member 55 in the separating direction z above explained.

First of all, the reflection type optical sensors 42 comprise the light-emitting members 52 (optical sources such as, for example, LEDs), the light-emitting optical system 52 that has the light-emitting lenses 58 arranged to form the optical spots 46 on the surface of the fixing belt 35 to which the light 45 is emitted and guided from the light-emitting members 52, the light receiver system having a plurality of light-receiving members 55 (such as light-receiving elements, for example, PDs (photo diodes)) and one light-receiving lens 61 corresponding at least two light-receiving members and further have the light receiver system to guide the reflected light 47.

The light-emitting member 52 and the light-receiving member 55 are supported by (or mounted on) the same board 71. The light-emitting lenses 58 and the light-receiving lenses 61 are formed into a single element as a lens array 63. The board 71 and the lens array 63 are supported by the sensor body (or case) of the reflection type optical sensor 42. The light-blocking member 65 is set in the sensor body 64 to suppress a flare.

It is possible to form the light-blocking member 65 and the sensor body 64 into an integrated plastic form.

As shown in FIG. 5B, a plurality of the light-emitting members 52 is arranged in the width direction x thereof and constructs a light emitting system. The width direction x is the direction of arrangement of the light-emitting member 52 in the light emitter system.

The plurality of light-emitting lenses 58 is arranged in the width direction to construct a light emitter system. Such width direction x is the array direction of arrangement of the light-emitting members 52 in the light emitter system.

The constant pitch or each light-emitting member 52 arrangement in the width direction x is assumed to be P as well as the pitch of the arrangement each light-emitting lens 58 in the width direction x.

The light-blocking members 65 separate the spaces in the separation direction z between the corresponding light-emitting member 52 and the light-emitting lens 58 and block the light in the light-emitting member 52 from the light in the light-emitting lens 52 so that a plurality of the light-blocking members 65 are arranged with a separation interval in these adjacent spaces.

Similar light-blocking members 65 are placed in the space between the light-emitting portion 54 and the detection portion 57.

In such structure, the light-blocking members 65 can be light-blocking surrounding walls formed in the sensor body 64 which has a formwork shape or can be a remaining wall of the sensor body 64 which is a formwork made from a drilled block that has an opening in the end of the space made by the formwork thereof.

The light 45 emitted from each of the light-emitting members 52 goes to the fixing belt 35 through a corresponding light-emitting lens 58 and from an optical spot 46 on the surface of the fixing belt 35. The reflection type optical sensor 42 generates a plurality of the optical spots 46 that have an arrangement pitch P in the width direction x.

One or a plurality of the light-receiving members 55 are placed in the width direction x as shown in FIG. 5D. The plurality of light-receiving members 55 are arranged in one-to-one correspondence against each light-emitting members 52 as shown in FIG. 5D wherein the light-receiving members 55 have a constant arrangement pitch P in the width direction. In other words, the light-emitting members 52 and the light-receiving members 55 are both arranged with the same pitch P in the width direction.

The light-receiving lenses 61 have no optical effects to the width direction x.

When the optical spots 46 are generated on the surface of the fixing belt 35 by emitting light thereto, the reflected light 47 comes from the surface of the fixing belt 35. Since the surface of the fixing belt 35 is not mirror surface, a scattering light component 47b is generated in addition to the nominal reflecting light component 47a.

A part of the reflected light 47 is guided to the light-receiving lenses 61, converted only in the moving direction y of the fixing belt 35 and detected by the light-receiving members 55. The detection of the reflected light 47 by the light-receiving members 55 is carried out once for each of a plurality of the optical spots 46 each having different position in the width direction.

Figure 6:
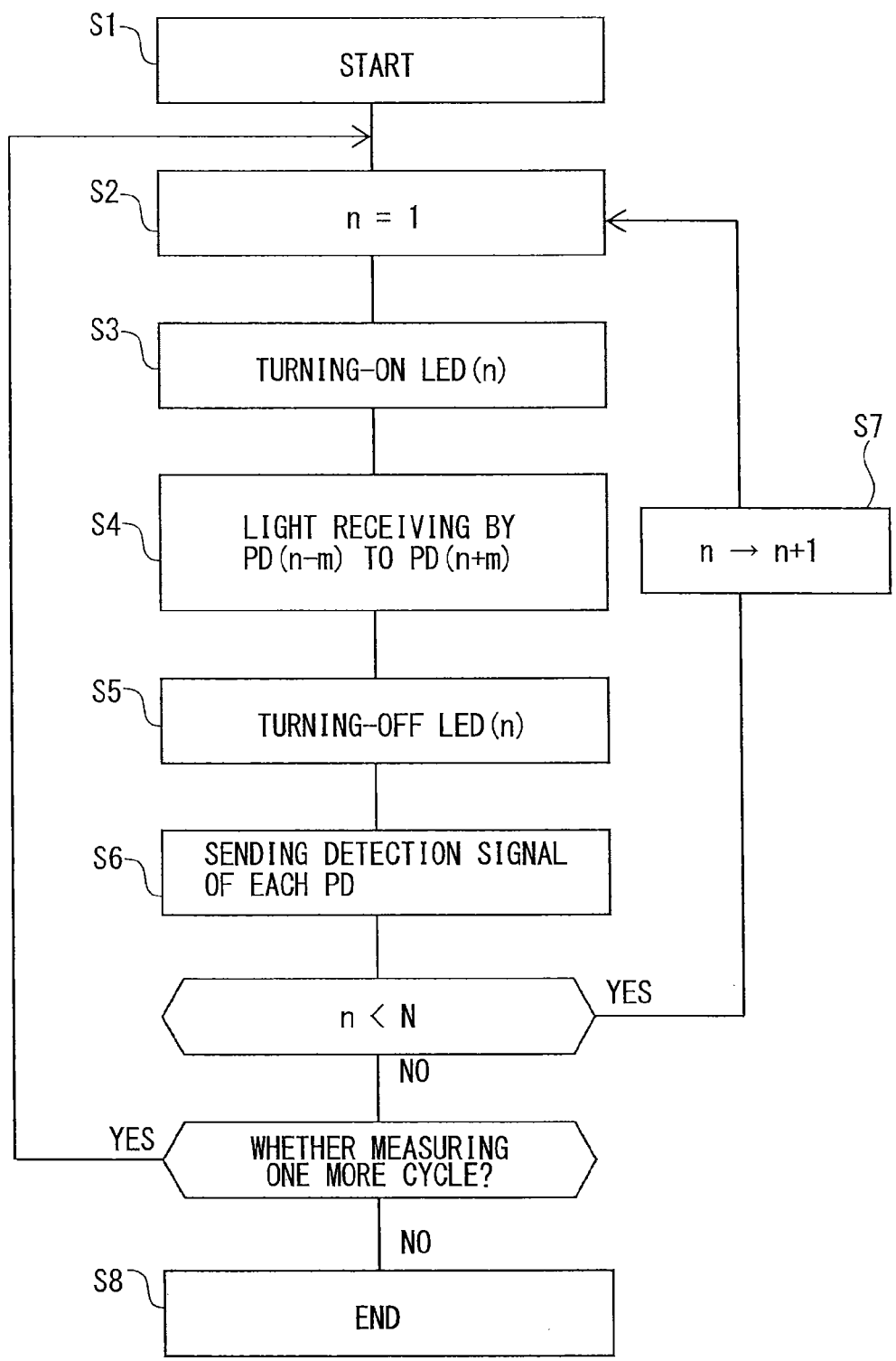
FIG. 6 is a schematic view that depicts a flow chart of the operating principle of a reflection type optical sensor.

The operation of the reflection type optical sensors 42 is explained using FIG. 6 that shows a flow chart thereof.

From the left end of FIG. 5D, the light-emitting members 52 are called LED(1), LED(2), . . . , LED(N) and the light-receiving members 55 similarly PD(1), PD(2), . . . , PD(N).

A plurality of the light-emitting members 52 repeats light-on and light-off each from the left end thereof, in other words, carrying out sequential on/off of the light.

When a control starts, an initial value '1' is set for the variable n in step 1 (or S1) and turns on the light of n-th light-emitting members 52 (or LED(n)).

Then, the reflected light 47 at the fixing belt 35 is detected by a plurality of the light-receiving members 55 locating peripheral to or including n-th light-receiving member 55 (or PD(n)) that corresponds to LED(n) that is turned on the light.

For the simplicity of the discussion, the quantity of the light-receiving members 55 that receive the same reflected light 47 from identically same optical spot 46 is odd pieces (2m+1), where m is an integer. Therefore, PD(n−m) to PD(n+m) can simultaneously detect the identically same reflected light 47.

When the (2m+1) pieces light-receiving members 55 detect the identically same reflected light 47, LED(n) is turned off.

Then in step 5 (or S5), the reflected light 47 detected by the (2m+1) pieces light-receiving members 55 is photo-electrically converted and amplified to be a detected signal 48. The detected signal 48 is sent to the surface condition judging device 43 as shown in FIG. 3.

In step 6 (or S6), n+1 is substituted into n in step 7 (or S7) if n<N in the comparison of n with N and then going back to step 1 (or S1), the above steps are repeated until the most right-end of light-emitting members 52, that is LED(N), turns on/off.

When the most right-ending LED(N) turns on/off after n=N, the step repetition is regarded as one cycle and the above sequential turn-on/off of the light ends.

However, adding step 8 (or S8) after step 6 (or S6), the above sequential turn-on/off of the light is carried out over a plurality of cycles and a process for averaging of the results of detection can be added to improve the precision of the detection.

For the light-emitting members 52 that turns on/off the light, all N pieces of the light-emitting members 52 from the left-end to the right-end are not necessary to be used but arbitrary N" (which is less and equal to N) pieces can be used. It is not necessary to start turning-n/off of the light with the most left-ending LED(1) and to end with the most right-ending LED(N), as well. It may work well to start turning-n/off of the light with the m-th light-emitting member 52, that is LED(N−m), from the most left-end position and to end with (N−m)-th light-emitting member 52, that is LED(N−m), from the most right-end.

The operation of the surface condition judging device 43 is discussed as follows using a flow chart shown in FIG. 7.

As for the surface condition judging device 43, receiving the detected signal 48 sent from the (2m+1) pieces of the light-receiving members 55 in step 11 (or S11), the detection result R(n) corresponding to each LED(n) is calculated after taking summation of the detected signals 48 detected at (2m+1) pieces of the light-receiving members 55. The intensity of the reflected light corresponding to each position in the width direction x at the optical spots 46 in other words, on the surface of the fixing belt 35 is obtained by this detection result R(n).

The operation to judge the surface condition of the fixing belt 35 is discussed in the following.

In case that there is a scratch 51 on the surface of the fixing belt 35, the nominal reflecting light component 47a and the scattering light component 47b in the reflected light 47 coming from the surface of the fixing belt 35 decreases and increases, respectively in comparison to the case that there is no scratch 51 on the surface of the fixing belt 35.

As for the reflection type optical sensors 42 shown in FIGS. 5A to 5D, the intensity of the light received by the light-receiving member 55, such as PD(n), decreases in accordance with the decrease of the nominal reflecting light component 47a when the nominal reflecting light component 47a decreases and the intensity of the light received by light-receiving members 55 from PD(n−m) to PD(n+m) increases in accordance with the increase of the scattering light component 47b when the scattering light component 47b decrease. When there are scratches 51, the intensity of light detected by light-receiving members 55 from PD(n−m) to PD(n+m) decreases in total.

By measuring the intensity of the received light, the surface condition, in other words, the position and the level of scratches 51 are calculated in a real-time fashion.

The method to judge the existence of the scratches 51 is explained in the flowing.

Since the detection result (n), corresponding to each position in the width direction on the fixing belt 35, that indicates the intensity of the reflected light is obtained, it is possible to judge the existence of the scratches 51 at the position where the intensity of the reflected light becomes low by comparing intensity of the reflected light each for each position in the width direction x by the surface condition judging device 43.

Figure 7:
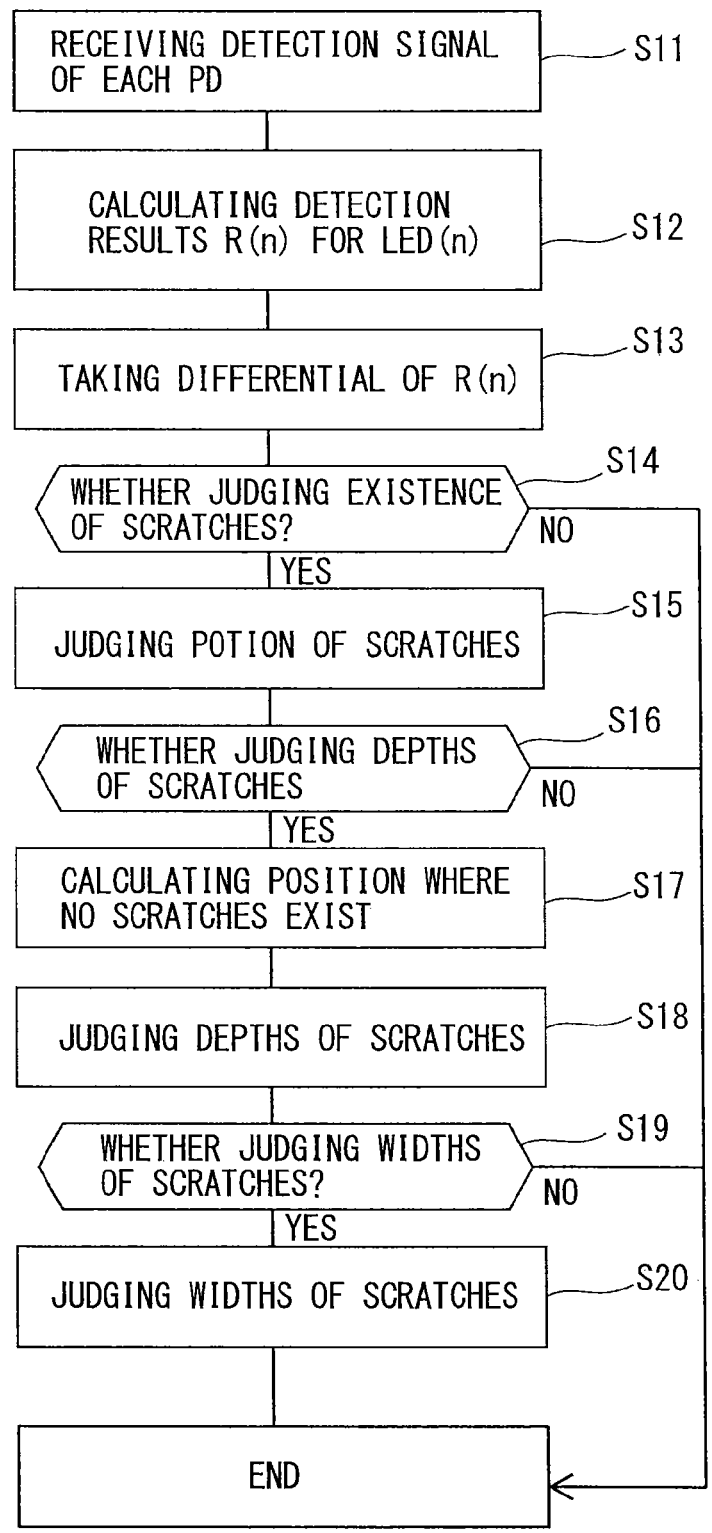
FIG. 7 is a schematic that depicts a flow chart of the operating principle of a surface condition judging device.
Figure 8A:
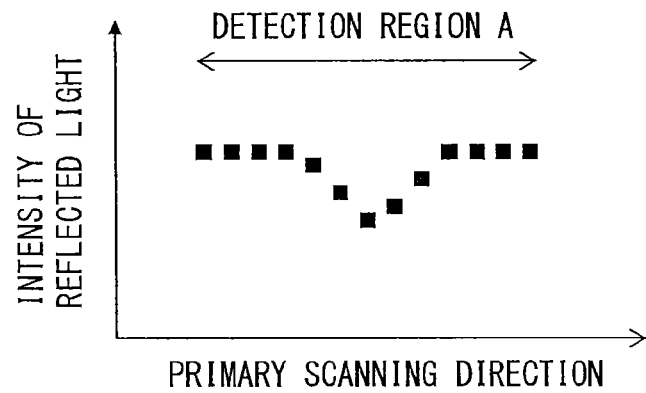
FIG. 8A is a schematic that depicts an output of the reflection type optical sensor, specifically, the relation of the intensity of the reflected light against the position along the principal scanning direction.
Figure 8B:
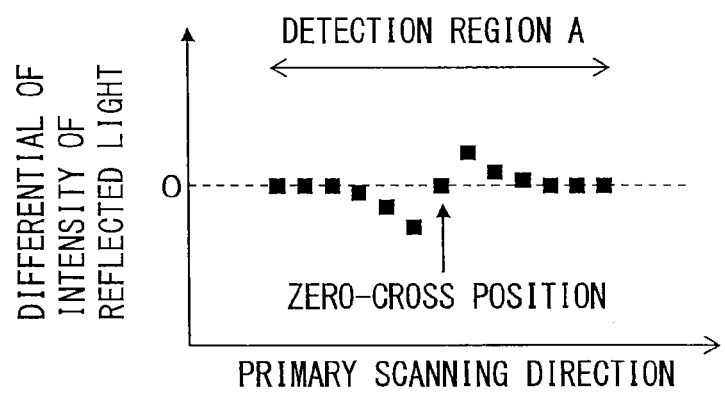
FIG. 8B is a diagram that shows the relation of the differential of the intensity of the reflected light against the position along the principal scanning direction.

FIG. 8A is a schematic that depicts the perspective of intensity of the reflected light received by the reflection type optical sensor 42 in each position in the width direction x (the primary scanning direction). As shown in FIG. 8B, it is possible to judge the positions of the scratches 51 (step 15 (or S15) in FIG. 7) as well as judging the existence of the scratches 51 (step 14 (or S14) in FIG. 7) by determining the position of zero-crossing where the differential value largely changes from the negative value to the positive one.

Since it is suggested that the decrease of the intensity of the reflected light is little when the absolute value of the differential is smaller than a predetermined threshold value, it may be possible to judge that there are no scratches 51. When it is judged that there are no scratches 51, the judgment process ends up.

Figure 9A:
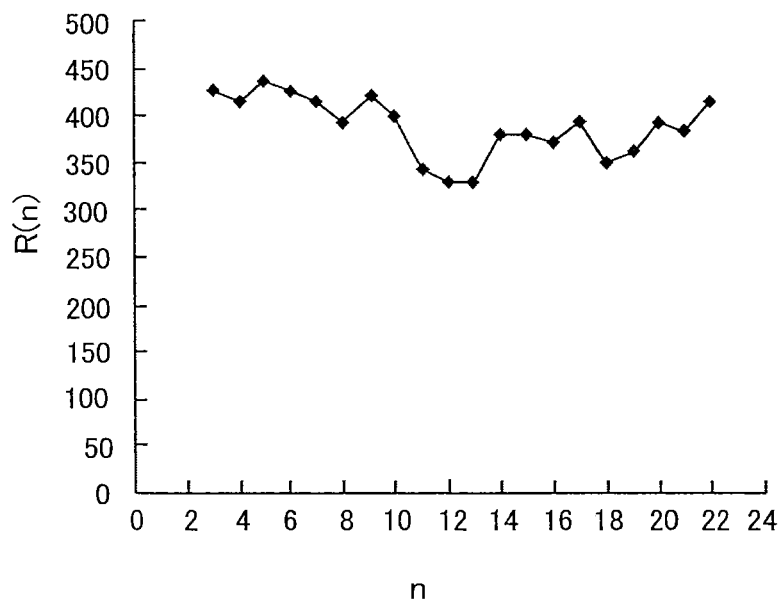
FIG. 9A is a diagram that shows the relation of a detection result R(n) using of the reflection type optical sensor against a light-illuminated position of an optical spot.

In FIG. 9A, an example of the detection result R(n), using the reflection type optical sensor 42 that is specifically provided with N=24, n=3 to 22, m=2 and an arrangement pitch P=1 mm for the fixing belt 35 experienced with 400,000 pieces of recording media S passing, is shown. Since the light emitted to the surface of the fixing belt 35 with the optical spots 46 in 1 mm pitch for the reflection type optical sensor 42, the abscissa axis indicates the light-illuminated positions (mm) of the optical spots as well as the order number n of the LED.

Figure 9B:
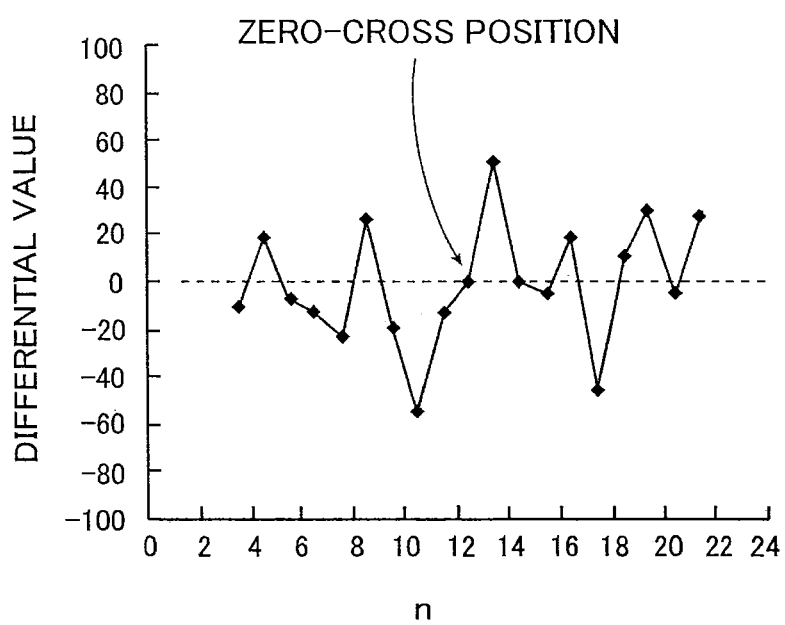
FIG. 9B is a diagram that shows the relation of the differential of the detection result R(n) using of the reflection type optical sensor against a light-illuminated position of an optical spot.

The differential of R(n) with regard to the width direction x, that is, more concretely the gradient of two points as R(n) and R(n+1) is shown in FIG. 9B. For the purpose of smoothening, a moving average is taken over the points R(n−1), R(n) and R(n+1) where are adjacent each other and the gradient of such moving averaged values may be used.

In FIG. 9B, n=12.5 at the zero-cross position, which is the intermediate between the positions of the optical spots 46 corresponding to LED(12) and LED(13), and then it is possible to judge that a scratch 51 exists at the position of 12.5 mm.

The method to judge the level of the scratches 51 is explained in the flowing.

At step 16 (or S16) shown in FIG. 7, judgment whether to judge the depths of the scratches 51 is done. When such judgment of the depths of the scratches 51 is not carried out, then the step for judgment ends up as is.

Figure 8C:
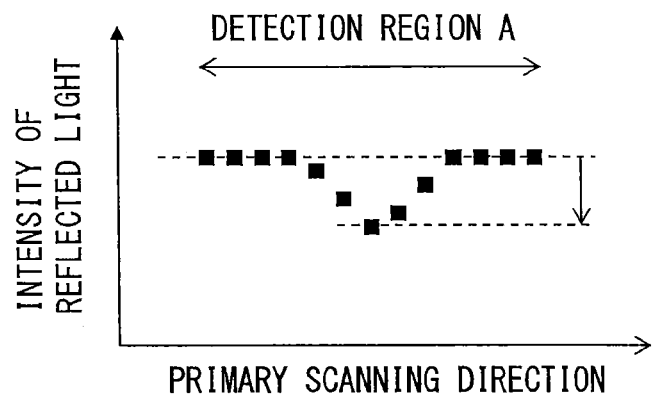
FIG. 8C is, similar to FIG. 8A, a diagram that shows the relation of the intensity of the reflected light against the position along the principal scanning direction in a view of judging scratch level.

Since it is expected that the deeper (rougher) the scratches 51 are, the more the intensity of the reflected light decreases, it is possible to detect the depths of the scratches 51 by measuring the decrease of the intensity of the reflected light. In other words, the deeper (rougher) the scratches 51 are, the more the light scattered on the surface of the fixing belt 35 so that the light received by light-receiving member 55 decreases, therefore it is possible to detect the depths of the scratches 51 by measuring the decrease of the intensity of the reflected light. FIG. 8C is a schematic that depicts the perspective of such depth detection.

FIG. 8C shows a case that the depths of the scratches 51 are simply obtained by measuring the minimum value for the detection results R(n), however it is expected that the light components due to the mounting status of the reflection type optical sensors 42 in the image generation apparatus 1 and tilt of fixing belt 35 etc. is biased to the detection result R(n).

In order to remove such light component for eliminating such bias, the following method is taken.

Firstly, two positions, ones where scratches 51 exist and the other ones where no scratches 51 do, are determined.

As for the positions where scratches 51 exist, it is possible to judge in the methods as explained above.

As for the positions where no scratches 51 exist, it is possible to determine such position that no scratches 51 exist by the result of the differential of the detection results R(n) with respect to the width direction x since the positions are those where changes of the detection result R(n) regarding the width direction are small so that the differential thereof are close to zero.

Assuming the position where scratch 51 exist be n0 and at least two positions where no scratches 51 exist be n1 and n2, it is possible to determine the decrease of the intensity of the reflected light by using the detection result R(n0) where a scratch 51 exist and those R(n1) and R(n2) where no scratches exist.

In order to remove such light component for eliminating such bias, the distance between the detection result at the position where the scratches 51 exist and an approximated straight line that goes through a plurality of detection results at the positions where scratches 51 do not exist is used.

The determination of the decrease of the intensity of the reflected light is actually explained against the results of FIG. 9B.

Figure 9C:
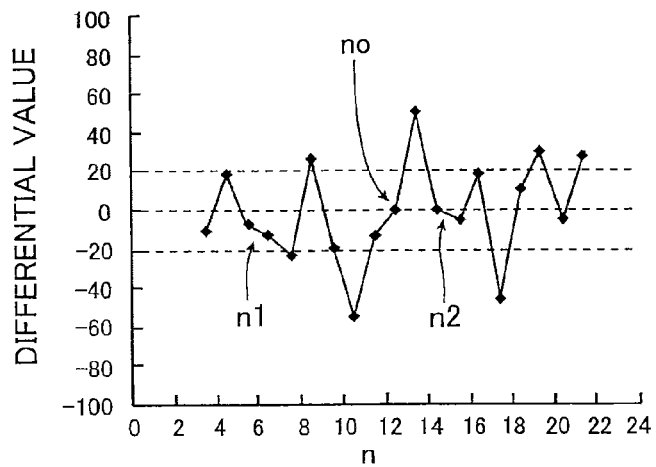
FIG. 9C is a diagram that shows a way to determine the position where no scratches exist.

FIG. 9C shows a small range of +/−20 regarding the differential of the detection result at the position n0 where scratches 51 exist as shown in FIG. 9B. From FIG. 9C, it is possible to select n1=5 and n2=15 for the positions n1 and n2 where no scratches 51 exist.

The depths of the scratches 51 (roughness of surface) are calculated using each detection result R(n) for n0=12.5 corresponding existence of scratches 51 and n1=6 and n2=15 corresponding no existence of scratches 51.

Figure 9D:
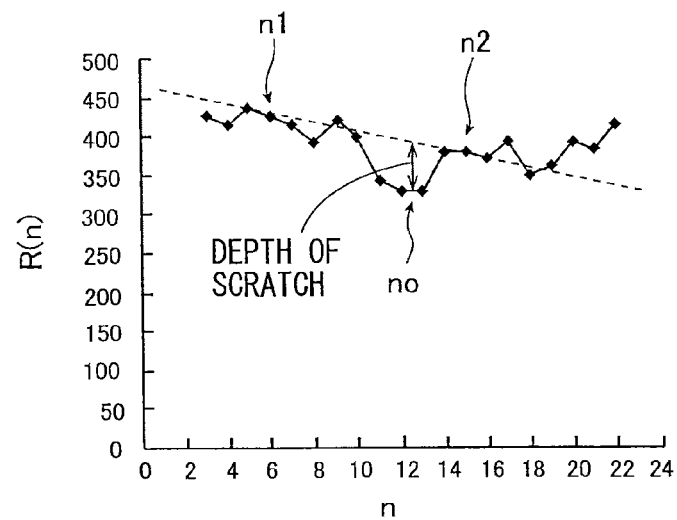
FIG. 9D is, similar to FIG. 9A, with a consideration of gradient of the moving body.

An approximated straight line is obtained by connecting R(n1) and R(n2) with a dotted straight line as shown in FIG. 9D. Then the depths of the scratches 51 are obtained (step 18 (or S18) shown in FIG. 7) as indicating with an arrow sign. For this example, the depth of the scratch 51 is 63.1 mm. (it is necessary to review as to whether a unit, mm of 63.1 is correct). The rate of the decrease of the intensity of the reflected light is 0.16 (16%).

As seen in FIG. 9D, there is a light component that biases the detection result corresponding to the depths of the scratches 51.

The larger the scratch level becomes, the more the decrease of the intensity of the reflected light.

The method for judging the widths (sizes) of the scratches 51 is explained in the following.

At the step 19 (or S19) shown in FIG. 7, judgment whether to judge the widths (sizes) of the scratches 51 is done. When such judgment of the widths of the scratches 51 is not carried out, then the step for judgment ends up as is.

The judgment of the center position of the scratches 51 where scratches 51 exist is possible to be carried out as explained above.

As for the widths of the scratches 51, it is determined to calculate the positions where the intensity of the reflected light regarding the detection result R(n) at such position that the scratches 51 exit is less than a pre-determined value of the decrease of the intensity of the reflected light that corresponds to the depths of the scratches 51, for example 50% thereof. Of cause the pre-determined value of the decrease of such intensity is not confined in 50% but can be arbitrarily selected.

Figure 9E:
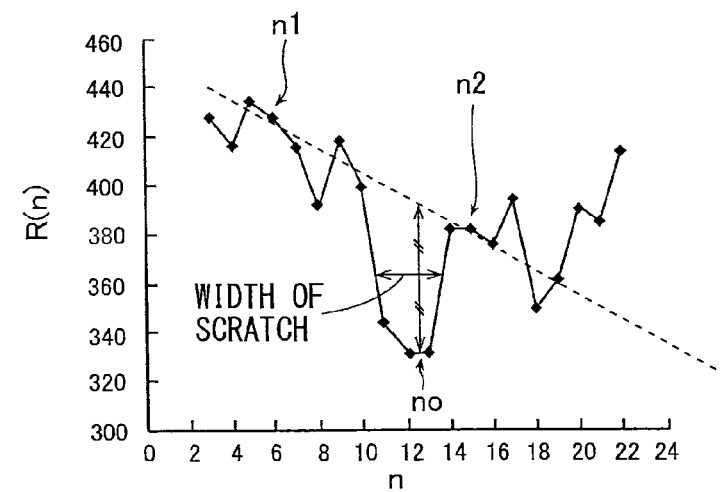
FIG. 9E is a diagram where the ordinate of the diagram shown in FIG. 9D is expanded.

FIG. 9E is a schematic that expands the axis of ordinate in vertical direction of FIG. 9D for ease of understanding. According to FIG. 9E, it is possible to judge the full width at half maximum of the scratches 51 is 3 mm.

In the assessment, all of the parameters regarding the surface conditions can be judged or only those necessary for the assessment may be judged.

The Second Embodiment

FIGS. 10A to 10D are schematics to show the reflection type optical sensors 42 (especially the reflection type optical sensors 42*a*).

Figure 10A:
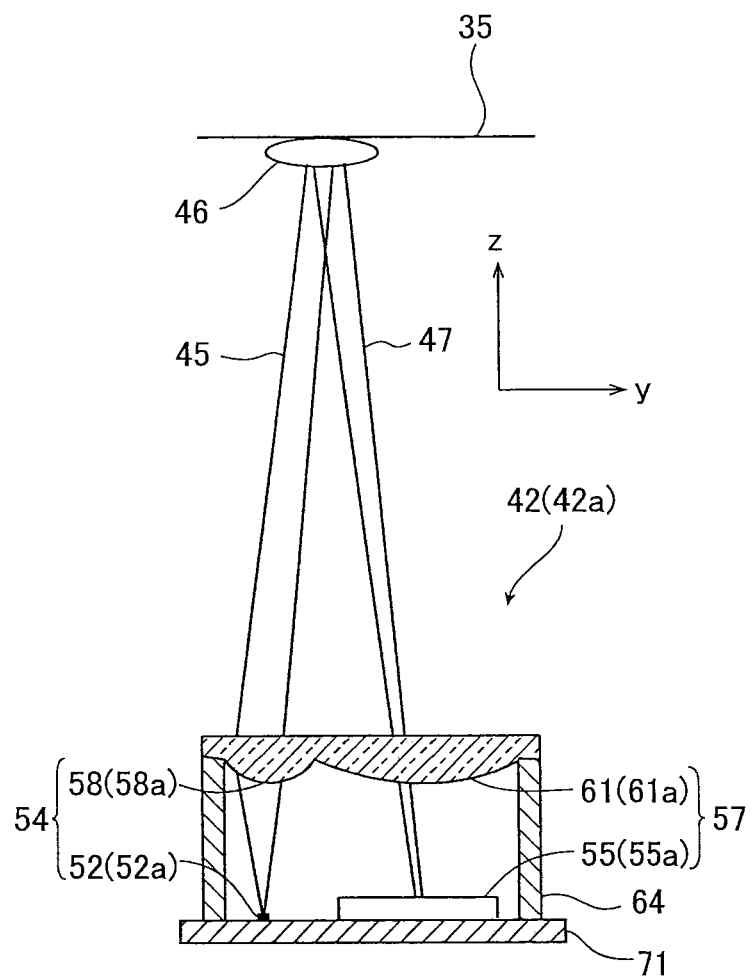
FIG. 10A is a schematic side view of the reflection type optical sensor in the width direction thereof.

FIG. 10A is a schematic side view of a reflection type optical sensor 42 in the width direction x thereof.

Figure 10B:
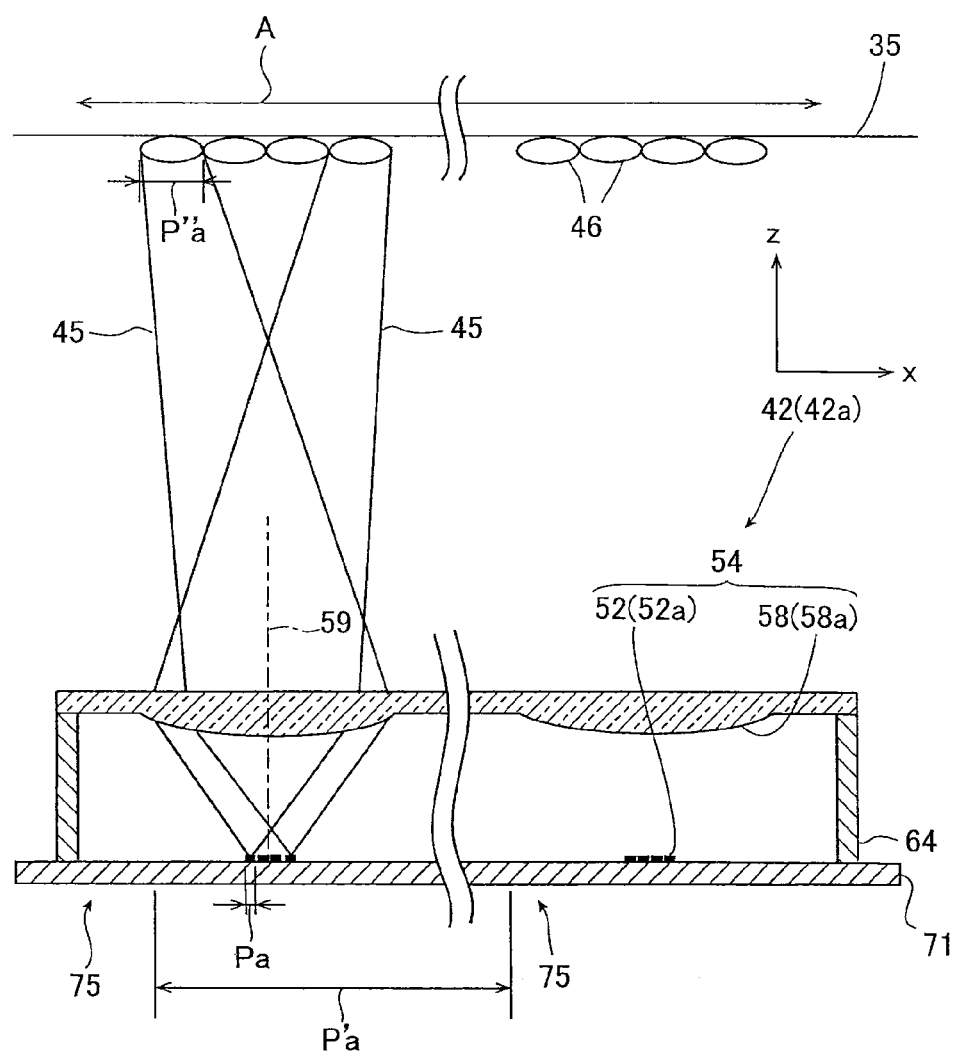
FIG. 10B is a schematic front view of the reflection type optical sensor shown in FIG. 10A from the light-emitting member in the moving direction.

FIG. 10B is a schematic front view of the reflection type optical sensor 42 shown in FIG. 10A from the light-emitting member 52 in the moving direction y.

Figure 10C:
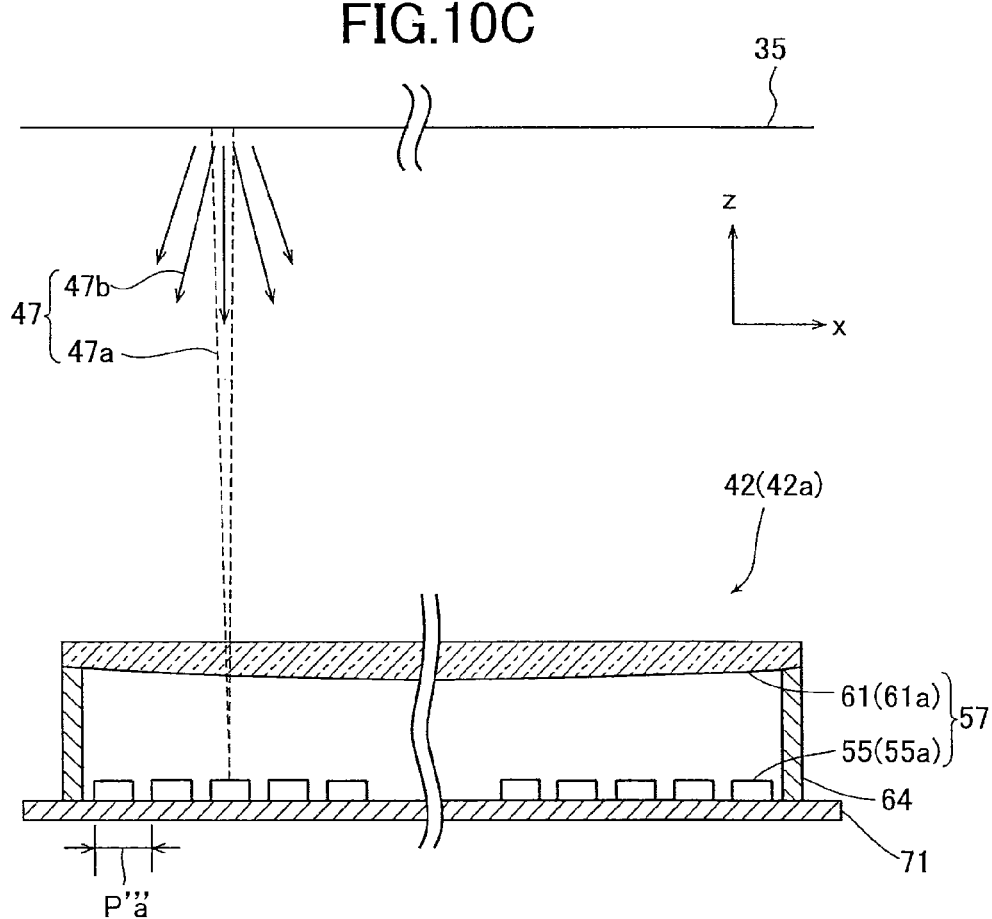
FIG. 10C is a schematic back view of the reflection type optical sensor shown in FIG. 10A from the light-emitting member in the moving direction.

FIG. 10C is a schematic of back view of the reflection type optical sensor 42 shown in FIG. 10A from the light-emitting member 52 in the moving direction y.

Figure 10D:
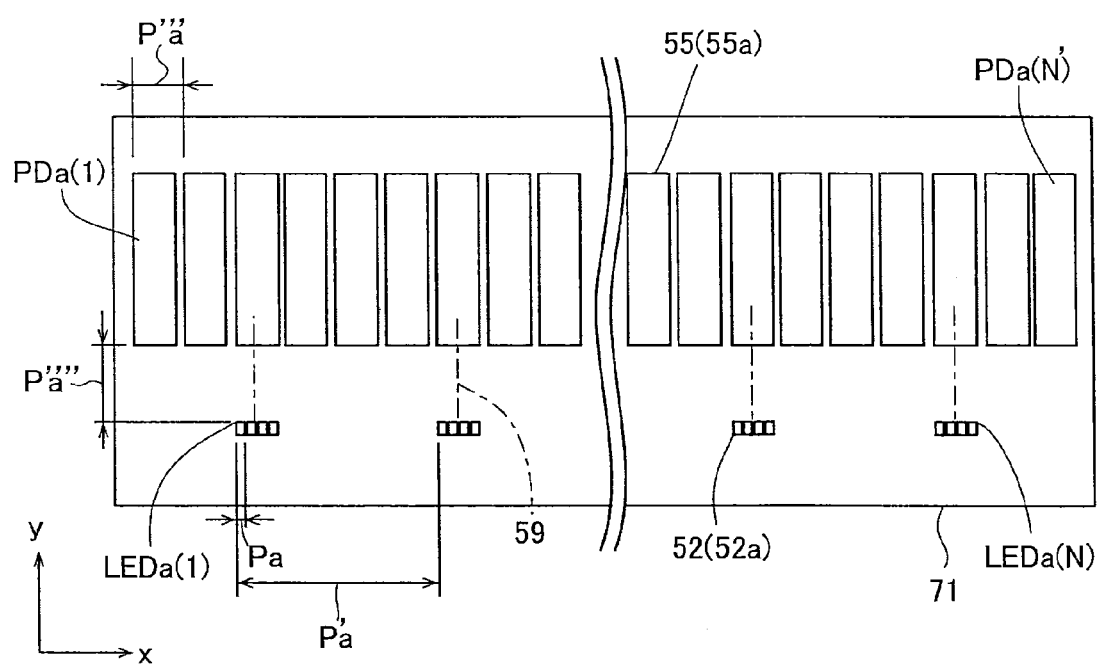
FIG. 10D is a schematic plan view of the board that supports the light-emitting member shown and the light-receiving member included in the reflection type optical sensor shown in FIG. 10A in the separating direction.

FIG. 10D is a schematic plan view of the board 71 that supports the light-emitting member 52 and the light-receiving member 55 in the separating direction z.

First of all, as shown in FIG. 10A, the reflection type optical sensors 42 (or, specifically the reflection type optical sensor 42*a* in this particular explanation) comprise a light-emitting member 52 (or, specifically a light-emitting member 52*a* in this particular explanation), a light-emitting lens 58 (or, specifically a light-emitting lens 58*a* in this particular explanation) that guides and converts the light emitted from the light-emitting member 52 to an optical spot 46 on the surface of the fixing belt 35 and a light-receiving member 55 (or, specifically a light-receiving member 55*a* in this particular explanation) that receives the reflected light 47 being guided by the light-receiving lens 61.

The light-emitting member 52 and the light-receiving member 55 are both supported (mounted) on the board 71. The board 71, the light-emitting lens 58 and the light-receiving lens 61 are supported by the sensor body 64.

As shown in FIG. 10B, a plurality of the light-emitting members 52 is closely arranged each other (for this particular case, four of the light-emitting members 52) in the width direction x so that a plurality of the light emitter systems is constructed and arrange.

A light-emitting lens 58 (or, specifically a light-emitting lens 58*a* in this particular explanation) corresponding to each light emitter system comprising a plurality (four pieces) of the light-emitting members 52 is prepared as a light-emitting optical system (multiple to one). The lens diameter of the light-emitting lens 58 (those adopted in FIG. 10B) in the width direction x is about four times larger as the lens diameter of the light-emitting lens 58 (those adopted in, for example, FIG. 5B). The lens parameters other than the lens diameter are same as those of the light-emitting lens 58 which is shown in FIG. 5A. The four light-emitting lenses 58 have an array pitch Pa (<P) in the width direction x.

As for the light-emitting lens 58, an anamorphic lens that has different optical power ratio for the width direction x and the moving direction y is adopted.

At the time to detect the surface condition of the fixing belt 35 using the reflection type optical sensor 42, the distance from detected surface or angle therefrom has variations due to surface waving, ruffling and curling of the fixing belt 35. It is difficult to remove all of these variations so that the precise detection of the surface condition is not possible since no correct output of the detected signal 48 is obtained in detecting the surface condition of the fixing belt 35 once variations of the above distance or angle between the reflection type optical sensors 42 and the fixing belt 35 are made.

For the present particular image generation apparatus 1, the influence of the variation of angles due to the surface waving of the fixing belt 35 is remarkably large among the deviation of distance of the detection surface or the angles in the reflection type optical sensors 42.

In this embodiment, an anamorphic lens that has different optical power ratio for the width direction x and the moving direction y is used. It is possible to keep the diameter of the light beam in the moving direction y of the reflected light 47 that is incidental to the light-receiving lens 61 by using the anamorphic lens to optimize the curvature radii in the moving direction y as well as keeping the diameter of the light beam in the width direction of the light that generates the optical spot 46 on the surface of the fixing belt 25 with a pre-determined designed diameter. It is possible to decrease the fluctuation of the detection output by suppressing the influence of the variation of angles due to the surface waving and avoid the degradation of the precision of the sensor detection.

A pair of a light emitter system composing with a plurality of the light-emitting members 52 and a light-emitting lens 58 corresponding thereto composes a light emitter unit 75. The light-emitting portion 54 (that comprises each light emitter system and light-emitting lens 58 with multiplying of quantity of light emitter units) of the reflection type optical sensor 42 is constructed by arranging a plurality of the light emitter units 75 in the width direction x.

The arrangement pitch of the light emitter units 75 in the width direction is P'a. In the present embodiment, the quantity of the light-emitting members 52a is four, however any quantity is acceptable if it is more than two.

For the purpose of easy understanding, the quantity of light emitter units 75 is selected to be nine. However, such quantity is not confined to be nine but those less than nine or more than nine are acceptable.

The reflection type optical sensors 42 have a plurality of optical spot 46 made on the fixing belt 35 with an arrangement pitch P''a in the width direction x since the light beam 45 emitted from each of the light-emitting members 52 generates an optical spot 46 on the surface of the fixing belt 35 through a corresponding light-emitting lens 58 in a right emitter unit 75.

As shown in FIG. 10C, a plurality of the light-receiving members 55 is arranged in the width direction x.

As shown in FIG. 10D, the line where a plurality of the light-receiving members 55 is arranged in the width direction is in the substantially same position with the optical axis 59 of the light-emitting lens 58a. For such arrangement, the arrangement pitch of the light-receiving members 55 in the width direction x is P''a.

For the present embodiment of the reflection type optical sensor 42, a relation such that P'''a, P'''a, P'a/4 and P are all substantially equal is satisfied.

One light-receiving lens 61 corresponds to all light-receiving members 55 that are arranged to be placed. For such light-receiving lens 61, an anamorphic lens that has different optical power ratio for the width direction x and the moving direction y can be adopted.

A plurality of the optical spots 46 is generated on the surface of the fixing belt 35 and the reflected light 47 is reflected from each of the optical spots 46. Since the surface of the fixing belt 35 is not a mirror surface, a scattering light component 47b is generated in addition to the nominal reflecting light component 47a in the reflection and a part of the reflected light 47 is guided by the light-receiving lenses 61 and received by the light-receiving member 55a.

The light-emitting members 52 are arranged in the width direction x with a pitch P'a in the light emitter unit 75 as shown in FIG. 10D. The elements of the light-emitting members 52 which are composed with four elements thereof are arranged with the width direction x with a pitch Pa.

The light-receiving members 55 are arranged in the width direction with a pitch P'''a. The separation distance between the light-emitting members 52 and the light-receiving members in the moving direction y is P''''a.

The light-emitting members 52 and the light-receiving members 55 are each named light-emitting members LEDa (1), LEDa(2), . . . , LEDa(N) and light-receiving members PDa(1), PDa(2), . . . , PDa(N), respectively.

Bing possible to use the light-emitting lens 58 which has a large diameter in the width direction x due to the construction such that the reflection type optical sensors 42a of the present embodiment has one light-emitting lens 58 corresponding to a plurality (four pieces for this case) of the light-emitting member 52, the pitch P''a of a plurality of the optical spots 46 on the surface of the fixing belt 35 can be kept equal to the pitch P shown in FIG. 5 and the intensity of the incidental light to the fixing belt 35 can be four times larger than that wherein the reflection type optical sensors 42 as shown in FIG. 5 is used.

As is clearly understood by FIG. 10B, at least two light beams 45 emitted from a plurality of the light-emitting members 52 in an identically same light emitter unit 75 are designed to substantially have surface symmetry to the surface that includes the light axis 59 of the light-emitting lens 58. In other words, each light emitter unit 75 is designed such that correspondence between the light-emitting members 52 and the optical spots 46 made on the surface of the fixing belt 35 provides a reverse relation in right and left. Therefore, the light emitter unit 75 in FIG. 10B has the most left light-emitting member 52 that corresponds to the fourth optical spot 46 from the left and the fourth light-emitting member 52 from the left corresponds to the most left optical spot 46. The four light-emitting members 52 in the light emitter unit 75 are symmetrically arranged in the both side from the surface that includes the light axis 59 of the light-emitting lens 58.

In this particular embodiment, the lenses may adopt the following parameters but are not limited to use them. The light-emitting lens 58 has a curvature radius of 4.6 mm, a conical constant of 0 and a lens diameter of 2.4 mm both in the width direction x, a curvature radius of 4.3 mm, a conical constant of −2.0 and a lens diameter of 10.5 mm in the moving direction y and the lens thickness of 6.6 mm.

The light-receiving lens 61 has a curvature radius of 5.0 mm, a conical constant of −1.0 and a lens diameter of 17 mm both in the width direction x, a curvature radius of 4.8 mm, a conical constant of −1.6 and a lens diameter of 10.1 mm in the moving direction y and the lens thickness of 6.6 mm.

The distance between the light-emitting lens 58 and the light-receiving lens 61 in the moving direction y is 2.53 mm and the distance of the light-emitting member 52 to the light-emitting lens 58 in the direction of the optical axis (separation direction z) is 10.37 mm and equal to the distance of the light-receiving member 55 to the light-receiving lens 61 in the optical axis direction.

The Third Embodiment

FIGS. 11A to 11D show the reflection type optical sensor 42 (the reflection type optical sensor 42b) regarding the present embodiment.

Figure 11A:
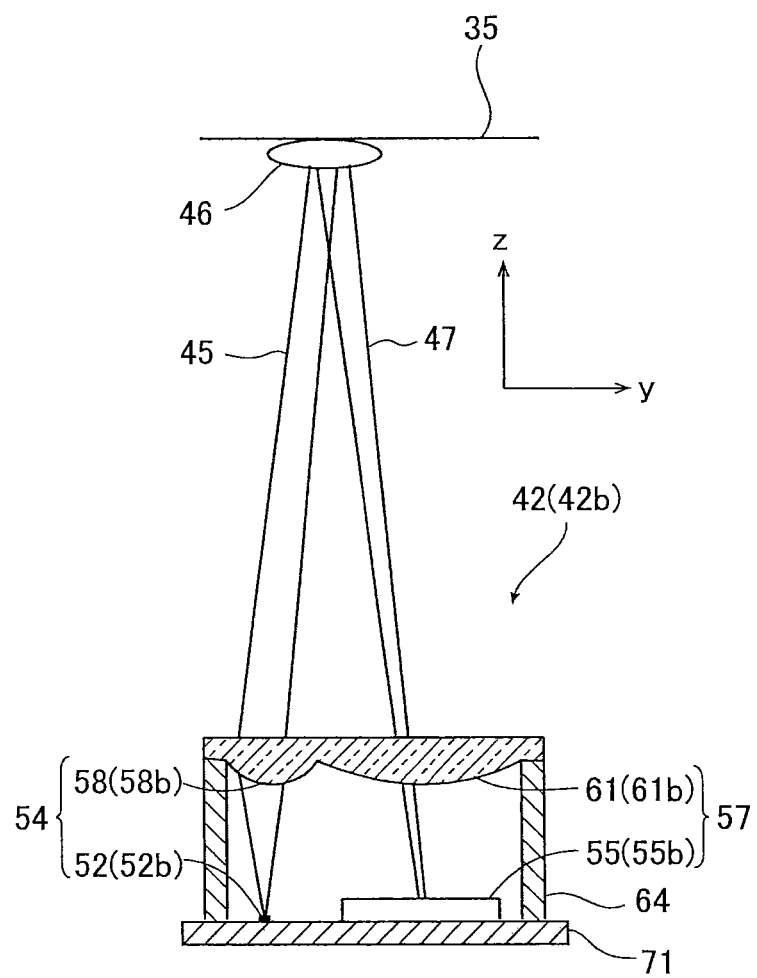
FIG. 11A is a schematic side view of the reflection type optical sensor regarding the third embodiment in the direction of width thereof.

FIG. 11A is a schematic side view of the reflection type optical sensor 42 from the width direction x.

Figure 11B:
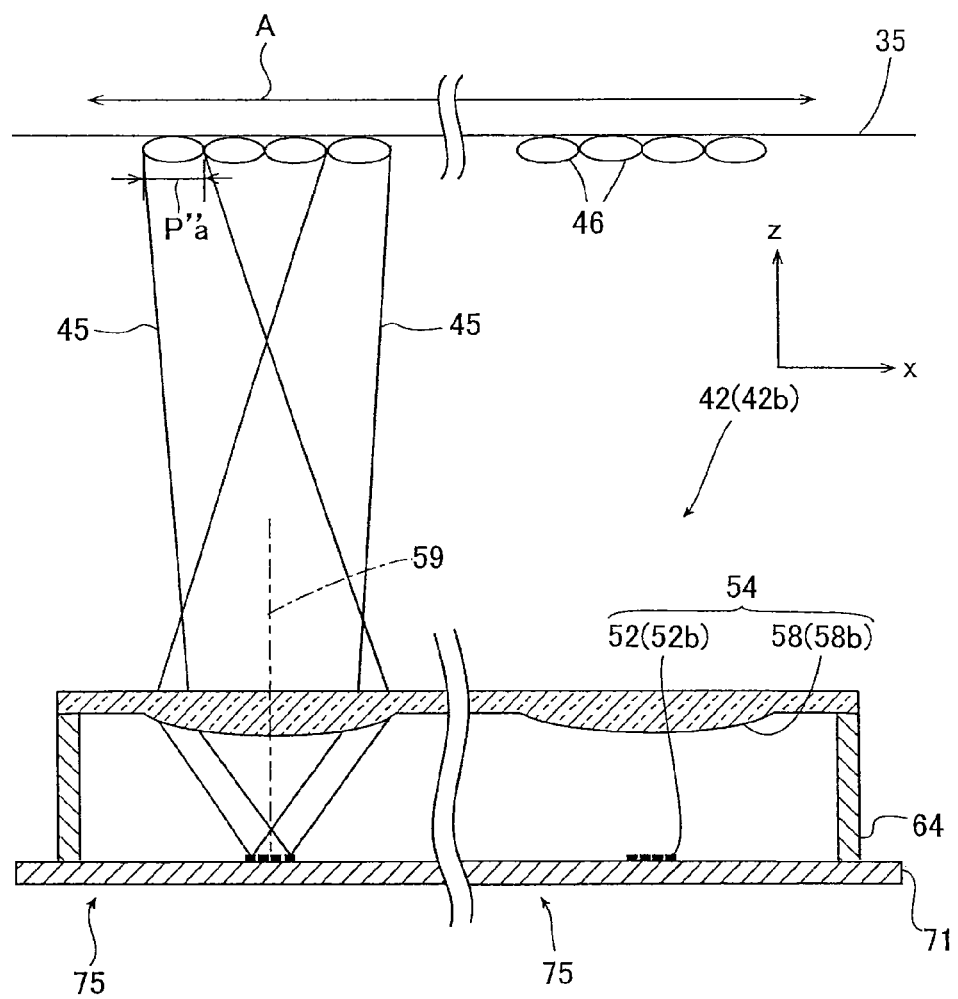
FIG. 11B is a schematic front view of the reflection type optical sensor shown in FIG. 11A from a light-emitting member in the moving direction.

FIG. 11B is a schematic front view of the reflection type optical sensor 42 shown in FIG. 11A from the light-emitting member 52 in the moving direction y.

Figure 11C:
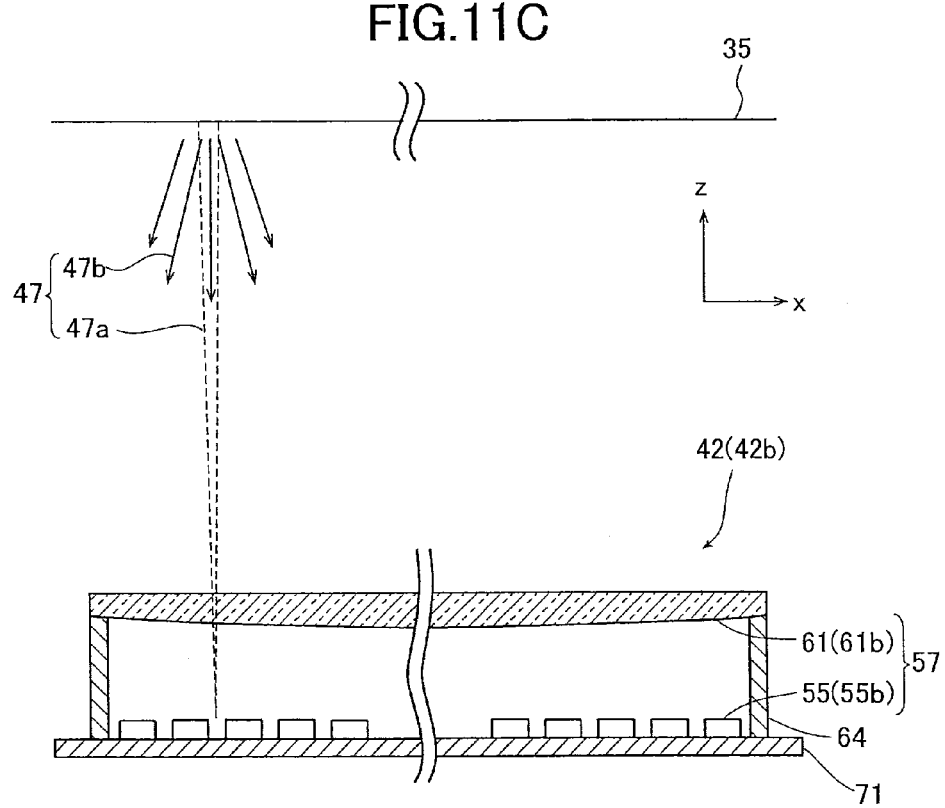
FIG. 11C is a schematic back view of the reflection type optical sensor shown in FIG. 11A from a light-receiving member in the moving direction.

FIG. 11C is a schematic back view of the reflection type optical sensor 42 shown in FIG. 11A from the light-receiving member 55b in the moving direction y.

Figure 11D:
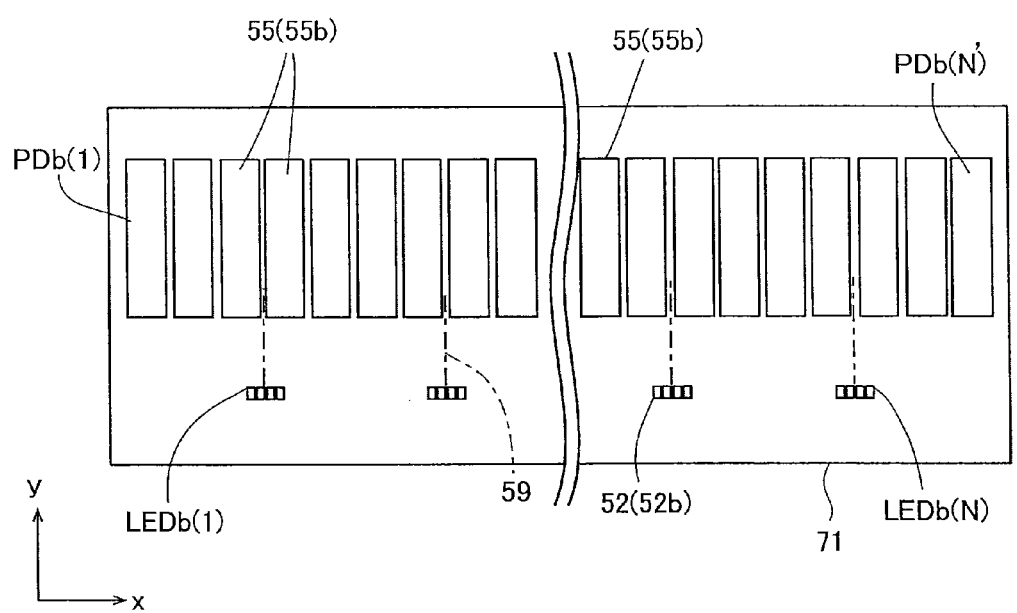
FIG. 11D is a schematic plan view of the board that supports a light-emitting member and a light-receiving member included in a reflection type optical sensor shown in FIG. 11A in the separating direction.

FIG. 11D is a schematic plan view of a board 71 that supports the light-emitting member 52 and a light-receiving member 55 in the separating direction z.

In the embodiment shown in FIGS. 10A to 10D, a plurality of the light-receiving members 55a is arranged with a pitch P″a in the width direction x against the light-emitting members 52a. As shown in FIG. 10C, the plurality of light-receiving members 55a are arranged in the substantially same positions of the optical axis 59 of the light-emitting lens 58a.

The feature of the present embodiment is that the position of the optical axis 59 of the light-emitting lens 58b in the width direction x is positioned in or near the intermediate position between two adjacent light-receiving members 55b.

First of all, as shown in FIG. 11A, the reflection type optical sensors 42 (or the reflection type optical sensor 42b) includes the light-emitting members 52 (or the light-emitting members 52b), the light-emitting lens 58 (or the light-emitting lens 58b) arranged such that the light beam 45 emitted from the light-emitting member 52 is guided to illuminate the moving body (or the fixing belt 35) and forms an optical spot 46 on the surface of the fixing belt 35, the light-receiving lenses 61 (or the light-receiving lens 61b) that is arranged to guide the reflected light 47 reflected by the fixing belt 35 and a light-receiving member 55 (or the light-receiving member 55b) that detects the reflected light 47.

The light-emitting members 52 and the light-receiving member 55 are supported by (that is, mounted on) the identically same board 71. The board 71, the light-emitting lens 58 and the light-receiving lens 61 are supported by a sensor body 64.

The modification from above embodiment is, as described above, only the position of the light-receiving members 55. The pitch P″a of the adjacent light-receiving members 55 is not modified so that lens parameters are same as those of the above embodiment.

FIGS. 11E to 11H show the reflection type optical sensors 42a and the output variation of the light-receiving member 55 when the fixing belt 35 (the moving body) to be tested is tilted by every 0.25 degrees in the range of 0 degree to +/−1.0 deg., where the skew angle B is a tilt angle of the fixing belt 35 with a rotational axis in the moving direction y.

Figure 11G:
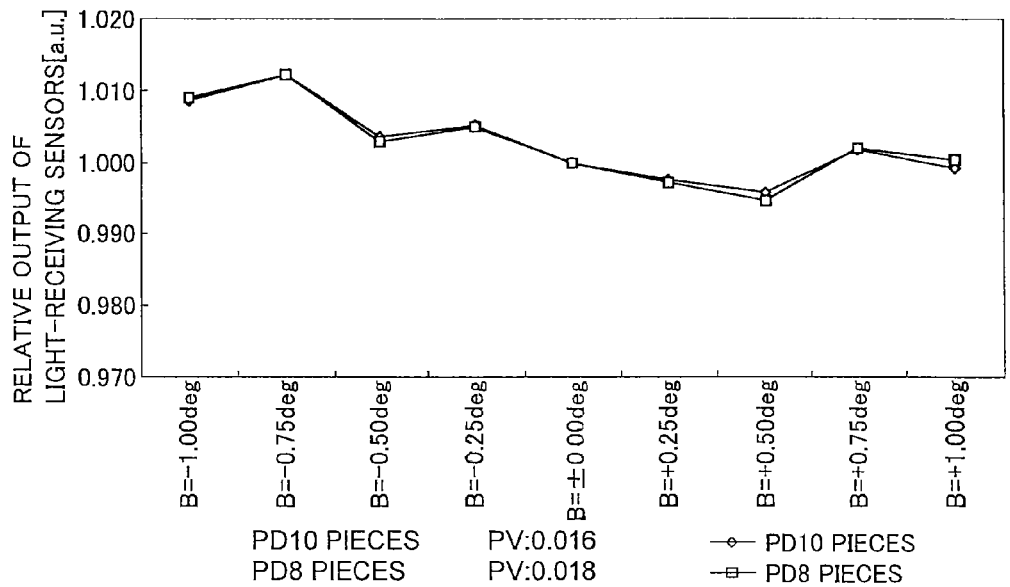
FIG. 11G is a diagram that shows an output variation of the light-receiving member used in the second embodiment when the light is emitted in a skew angle B of 0 to +/−1.0 degree with 0.25 degrees step using a reflection type optical sensor (LEDb(8)) regarding the second embodiment applied to a fixing belt (a moving body) as a test object.
Figure 11H:
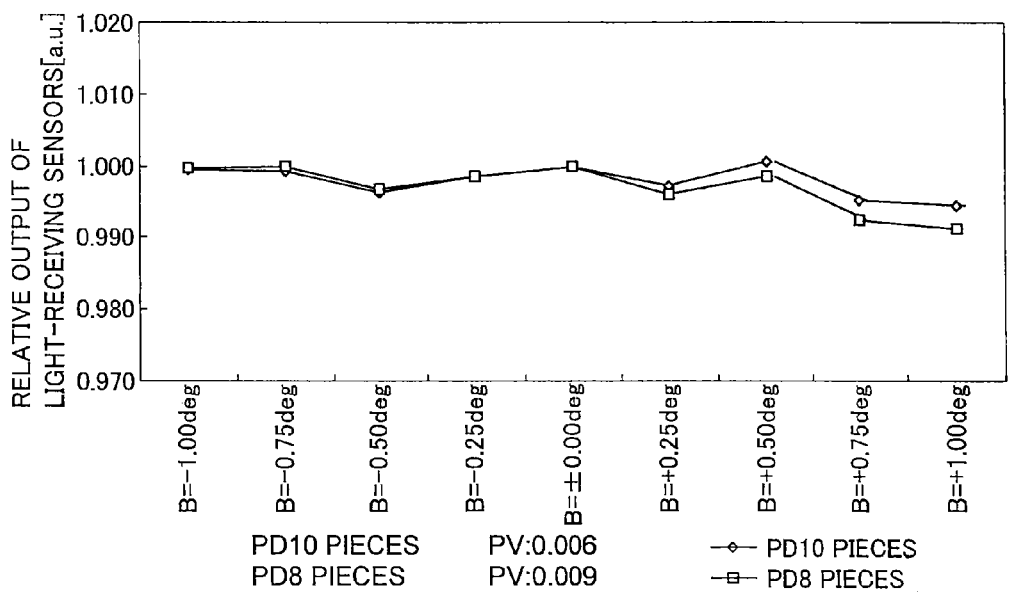
FIG. 11H is a diagram that shows an output variation of the light-receiving member used in the second embodiment when the light is emitted in a skew angle B of 0 to +/−1.0 degree with 0.25 degrees step using a reflection type optical sensor (LEDb(8)) regarding the third embodiment applied to a fixing belt (a moving body) as a test object.

The light-emitting member 52 that turns on the light is the seventh light-emitting member 52 (that is light-emitting members LEDa(7) and LEDb(7) as shown in FIGS. 11E and 11F, respectively) from the left side and the eighth light-emitting member 52 (that is light-emitting members LEDa(8) and LEDb(8) as shown in FIGS. 11G and 11H). The output of the light-receiving member 55 is set to be unity (we call this as a relative light-receiving output) for the skew angle B=0 degree. As mentioned above, total summation of the detected signals 48 at the plurality of light-receiving members 55 is the detection output (or the intensity of the reflected light) as the result of the detection. For the purpose of simplicity, the quantity of the light-receiving members 55 is limited up to 10 pieces or 8 ones.

Letting PV value be the absolute differential value between the maximum and the minimum of the detection output for the skew angle ranging of +/−1.0 deg., the PV values for the cases when different light-emitting members 55 turn on the light are compared for each reflection type optical sensors 42a and 42b. Idealistically, PV values should be consistently same even for the different light-emitting members 52 turns on the light. The better, the smaller the differences are. It is possible to judge that the smaller the PV values are, the smaller the detection errors due to the difference of the light-emitting members 52 are.

According to the results as shown in FIGS. 11E to 11H, the PV values are smaller when the reflection type optical sensors 42b in the present embodiment are used than when the reflection type optical sensors 42a in the above embodiment are used.

As discussed above, once the reflection type optical sensors 42b are designed such that the fluctuation of the detection output due to a skew angle which is a tilt angle of the fixing belt 35 around the axis directing to the moving direction y has the same behavior even for different light-emitting members 52 that turn on the light, it is possible to suppress the detection error due to the difference of the light-emitting members 52.

The Fourth Embodiment

FIGS. 12A to 12D depict the reflection type optical sensors 42 (specifically, the reflection type optical sensors 42c) used for the present embodiment.

Figure 12A:
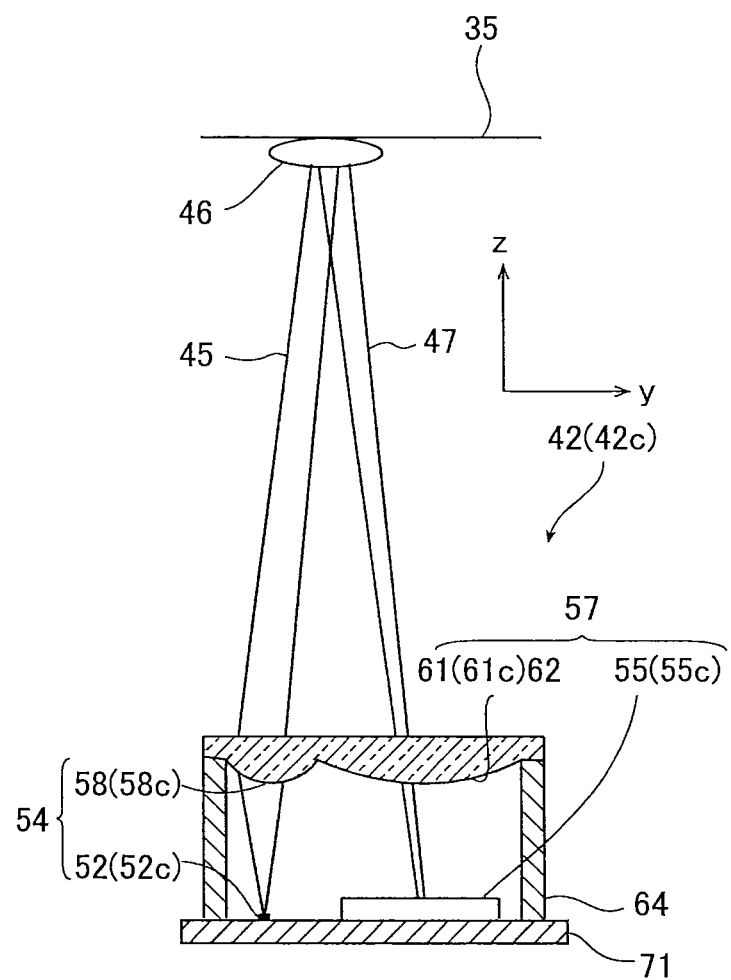
FIG. 12A is a schematic side view of the reflection type optical sensor regarding the fourth embodiment in the direction of the width thereof.

FIG. 12A is a schematic side view of a reflection type optical sensor 42 in the width direction x.

Figure 12B:
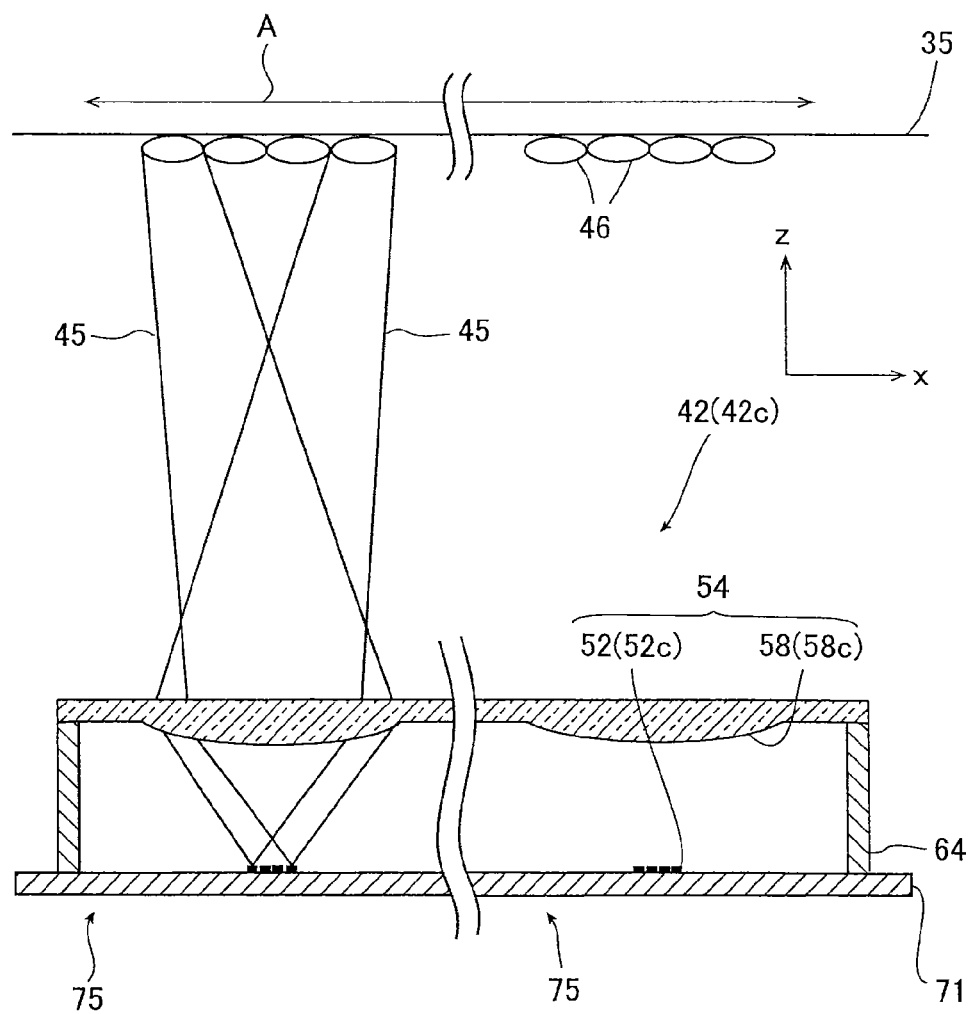
FIG. 12B is a schematic front view of the reflection type optical sensor shown in FIG. 12A from a light-emitting member in the moving direction.

FIG. 12B is a schematic front view of the reflection type optical sensor 42 as shown in FIG. 12A from a light-emitting member in the moving direction y.

Figure 12C:
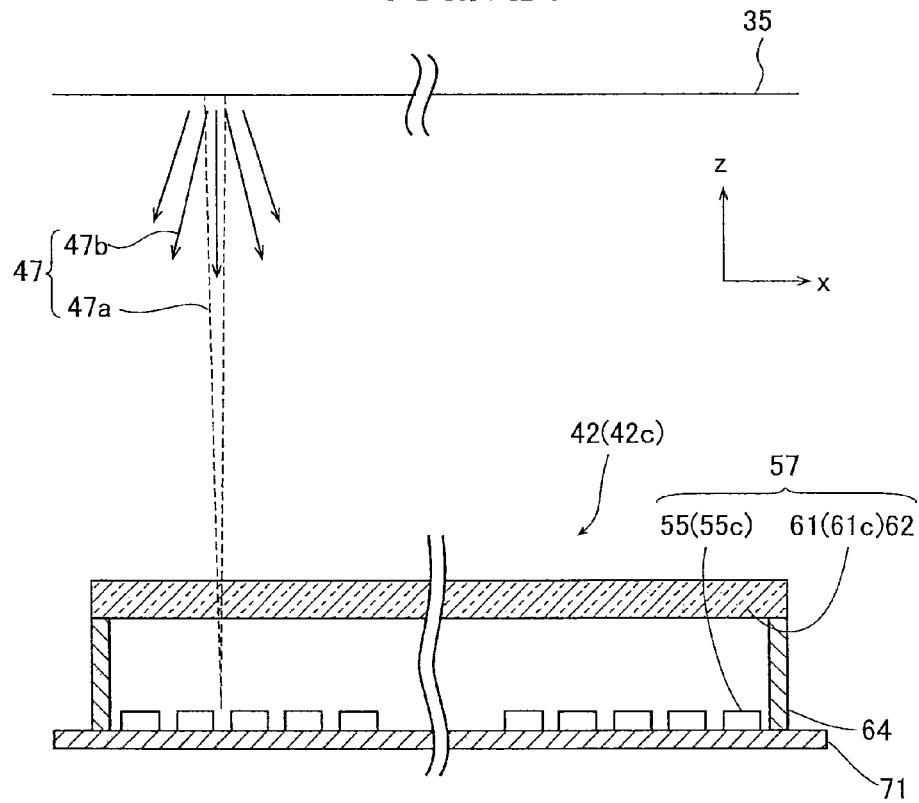
FIG. 12C is a schematic back view of the reflection type optical sensor shown in FIG. 12A from a light-receiving member in the moving direction.

FIG. 12C is a schematic back view of the reflection type optical sensor 42 as shown in FIG. 12A from the light-receiving member 55 in the moving direction y.

Figure 12D:
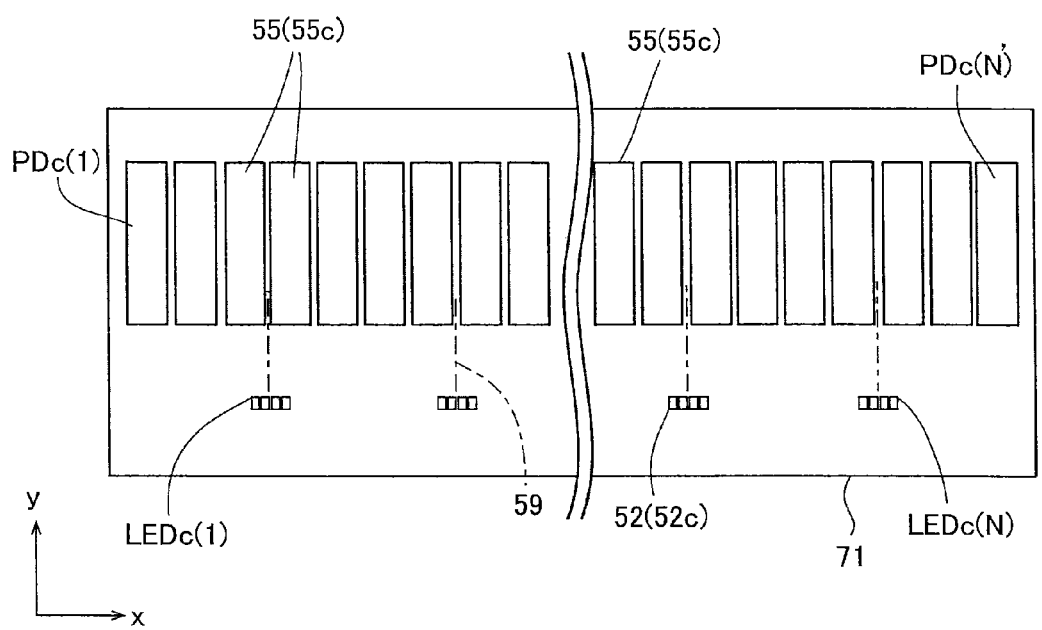
FIG. 12D is a schematic plan view of the board that supports a light-emitting member and a light-receiving member included in the reflection type optical sensor shown in FIG. 12A in the separating direction.

FIG. 12D is a schematic plan view of the board 71 that supports the light-emitting member 52 and the light-receiving member 55 in the separating direction z.

An anamorphic lens is used for the light-receiving lenses 61b of the reflection type optical sensors 42b for the embodiment shown in FIGS. 11A to 11D. However the present embodiment has a feature that a cylindrical lens 62 that convert the light (reflected light 47) in one axis is used for the light-receiving lens 61c of the reflection type optical sensors 42c (of cause it is possible to use cylindrical lenses 62 for the other embodiments). It is known that cylindrical lenses have no optical effects to the width direction x or array direction of arrangement of the optical spots 46 (including the case such that the arranged line of the optical spots 46 are tilted against the array direction of arrangement).

As shown in FIG. 12A, the reflection type optical sensors 42 (particularly the reflection type optical sensor 42c) includes the light-emitting members 52 (particularly the light-emitting members 52c), the light-emitting lens 58 (particularly the light-emitting lens 58c) arranged such that the light beam 45 emitted from the light-emitting member 52 is guided to illuminate the moving body (or the fixing belt 35) and forms an optical spot 46 on the surface of the fixing belt 35, the light-receiving lenses 61 (particularly the light-receiving lens 61c) that is arranged to guide the reflected light 47 reflected by the fixing belt 35 and a light-receiving member 55 (particularly the light-receiving member 55c) that detects the reflected light 47.

The light-emitting members 52 and the light-receiving member 55 are supported by (mounted on) identically same board 71. The board 71, the light-emitting lens 58 and the light-receiving lens 61 are supported by a sensor body 64.

As shown in FIG. 12B, the reflection type optical sensors 42 is constructed such that a plurality of the light-receiving members 55 (particularly PDc) are arranged in the width direction x. Therefore, it is necessary to the reflected light 47 incidental to the light-receiving members 55 has to be converted in the moving direction y, considering the positions and the size of the light-receiving members 55, however not to in the width direction x by effecting of the light-receiving lenses 61 therein. As the result, cylindrical lenses 62 that have no optical effects in the width direction x used for the light-receiving lenses 61.

Using cylindrical lenses 62 that has no optical effects in the width direction x used for the light-receiving lenses 61, it is possible to suppress the variation of the intensity distribution of the receiving light in the width direction x regarding the light-receiving members 55 against the difference of the light emitting members 52 that turn on the light and therefore to precisely detect the surface condition of the fixing belt 35.

In this particular embodiment, the lenses may adopt the following parameters but are not limited to use them. The light-emitting lens 58 has similar parameters to those used in each previous embodiment. As light-receiving lenses 61, the curvature radius and conical constant in the width direction are different from those adopted in the first embodiment. The curvature radius and the conical constant of the light-receiving lenses 61 in the width direction are infinity and zero, respectively.

The position and pitch of the arrangement regarding the light-emitting members 52 and the light-receiving members 55 are same as those adopted in the second embodiment.

The Fifth Embodiment

FIG. 13A to 13D depict the reflection type optical sensors 42 (specifically, the reflection type optical sensors 42d) used for the present embodiment.

Figure 13A:
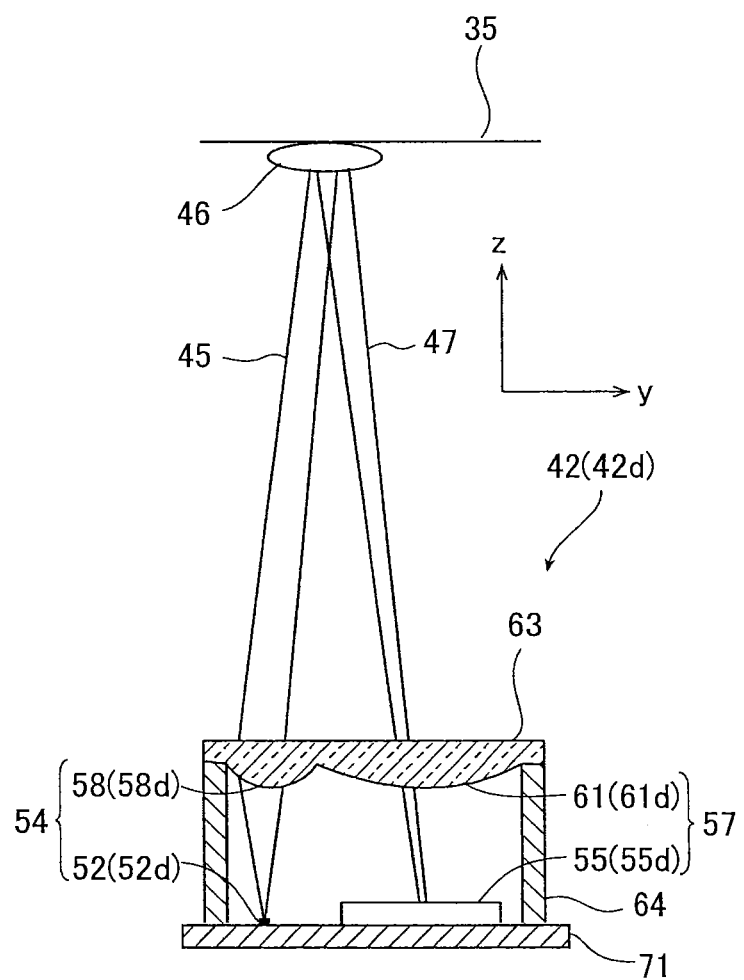
FIG. 13A is a schematic side view of the reflection type optical sensor regarding 5 in the direction of the width thereof.

FIG. 13A is a schematic side view of the reflection type optical sensor 42 in the width direction x.

Figure 13B:
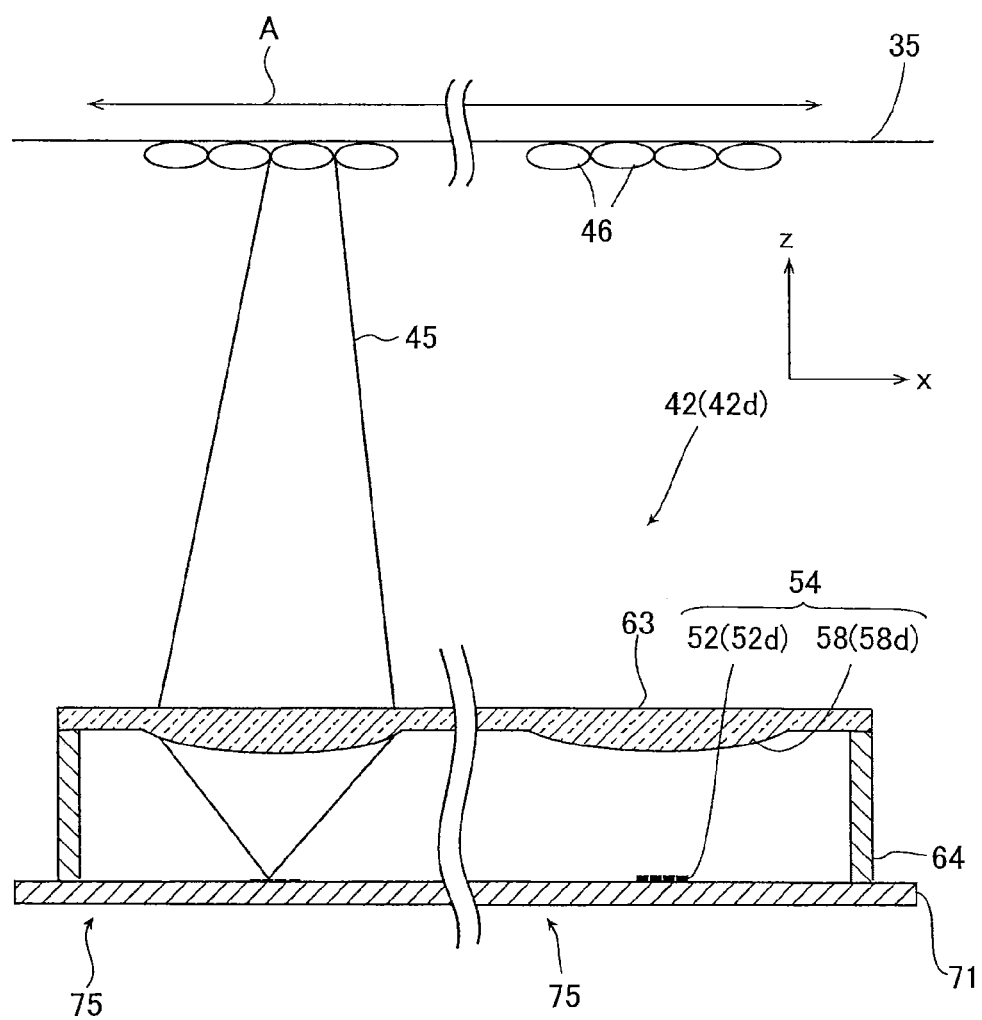
FIG. 13B is a schematic front view of the reflection type optical sensor shown in FIG. 13A from a light-emitting member in the moving direction.

FIG. 13B is a schematic front view of the reflection type optical sensor 42 as shown in FIG. 13A from a light-emitting member in the moving direction y.

Figure 13C:
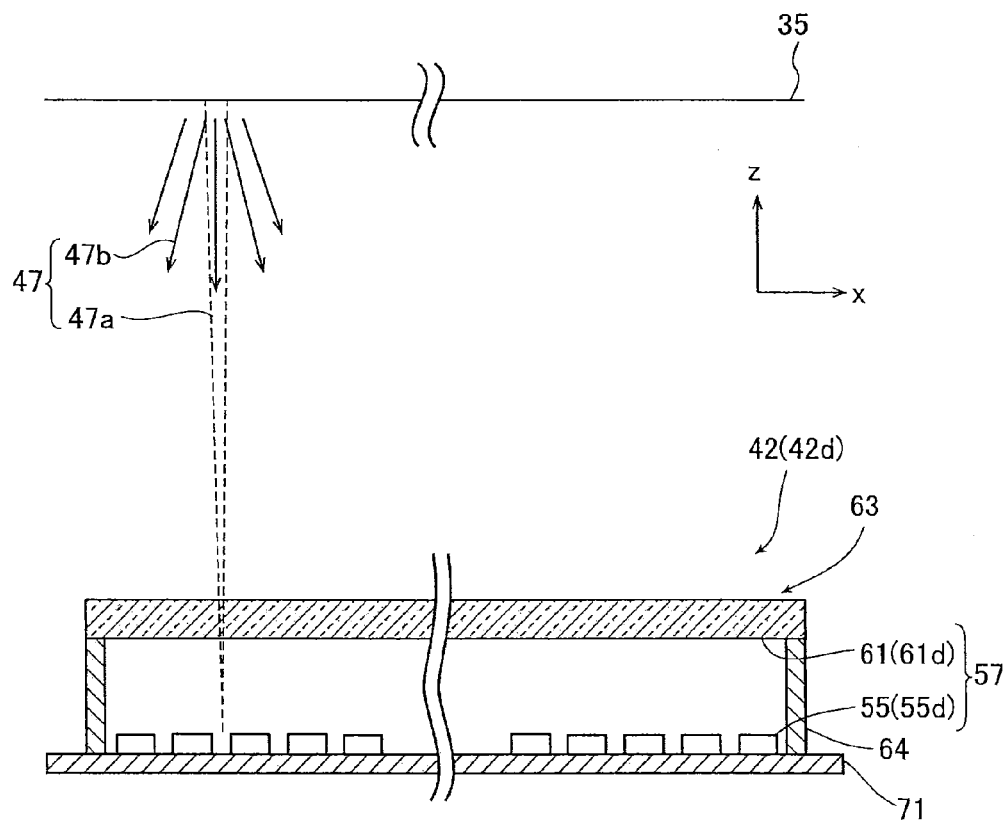
FIG. 13C is a schematic back view of the reflection type optical sensor shown in FIG. 13A from a light-receiving member in the moving direction

FIG. 13C is a schematic back view of the reflection type optical sensor 42 as shown in FIG. 13A from the light-receiving member 55 in the moving direction y.

Figure 13D:
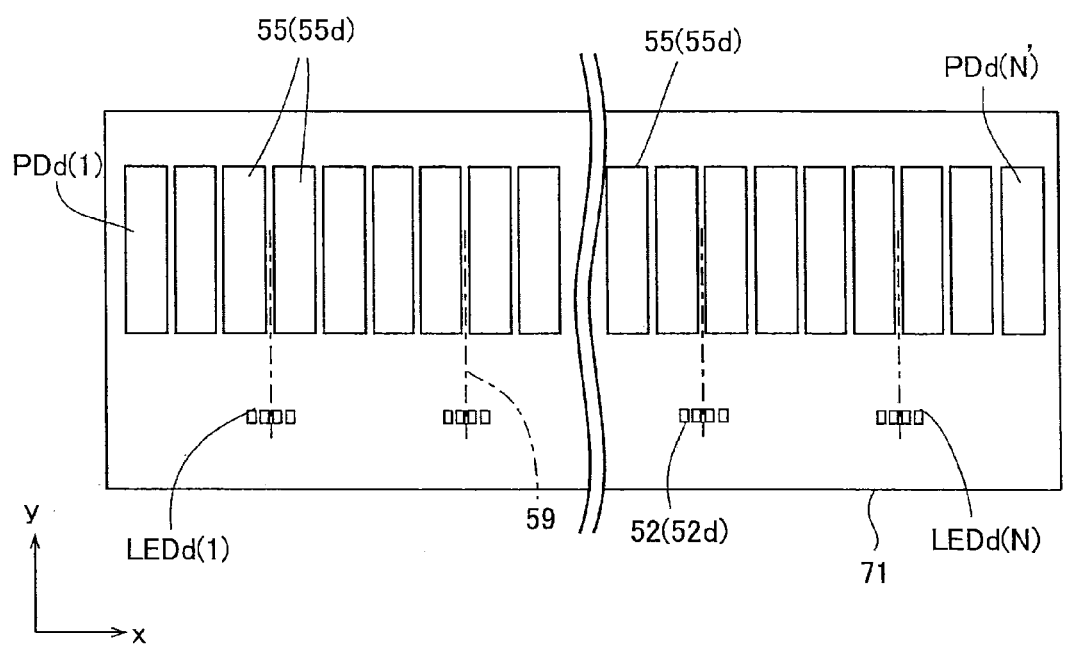
FIG. 13D is a schematic plan view of a board that supports a light-emitting member and a light-receiving member included in a reflection type optical sensor shown in FIG. 13A in the separating direction.

FIG. 13D is a schematic plan view of the board 71 that supports the light-emitting member 52 and the light-receiving member 55 in the separating direction z.

In each of the previous embodiments, the reflection type optical sensors 42 are designed such that the light-emitting lenses 58 and the light-receiving lenses 61 are arranged in pre-determined positions. The present embodiment features that the light-emitting lenses 58 and the light-receiving lenses 61 are formed into a single element called a lens array 63 (of cause it is possible to use the lens array 63 for the other embodiments).

As shown in FIG. 13A, the reflection type optical sensors 42 (the reflection type optical sensor 42d) includes the light-emitting members 52 (the light-emitting members 52d), the light-emitting lens 58 (the light-emitting lens 58d) arranged such that the light beam 45 emitted from the light-emitting member 52 is guided to illuminate the moving body (or the fixing belt 35) and forms an optical spot 46 on the surface of the fixing belt 35, the light-receiving lenses 61 (particularly the light-receiving lens 61d) that is arranged to guide the reflected light 47 reflected by the fixing belt 35 and a light-receiving member 55 (particularly the light-receiving member 55d) that detects the reflected light 47.

The light-emitting members 52 and the light-receiving member 55 are supported by (mounted on) identically same board 71. The board 71, the light-emitting lens 58 and the lens array 61 mentioned above are supported by a sensor body 64.

For this embodiment, it can be expected to decrease the fluctuation of the detection output and to accurately detect the surface condition of the fixing belt 35 since the workability to assemble lenses (such as the light-emitting lens 58 or the light-receiving lens 61) with the refection type optical sensors 42 and the accuracy to physically arrange a plurality of lenses can be improved.

FIGS. 14A to 14D show the reflection type optical sensors 42 of the present embodiment.

Figure 14A:
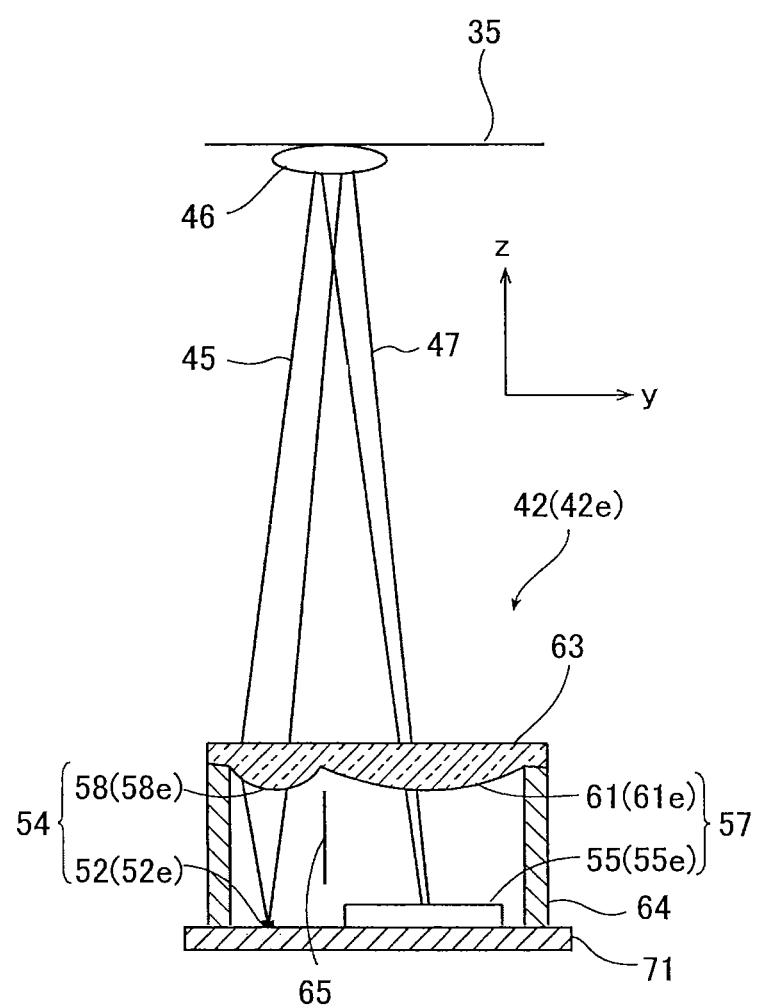
FIG. 14A is a schematic side view of the reflection type optical sensor regarding the sixth embodiment.

FIG. 14A is a schematic side view of the reflection type optical sensor 42 in the width direction x.

Figure 14B:
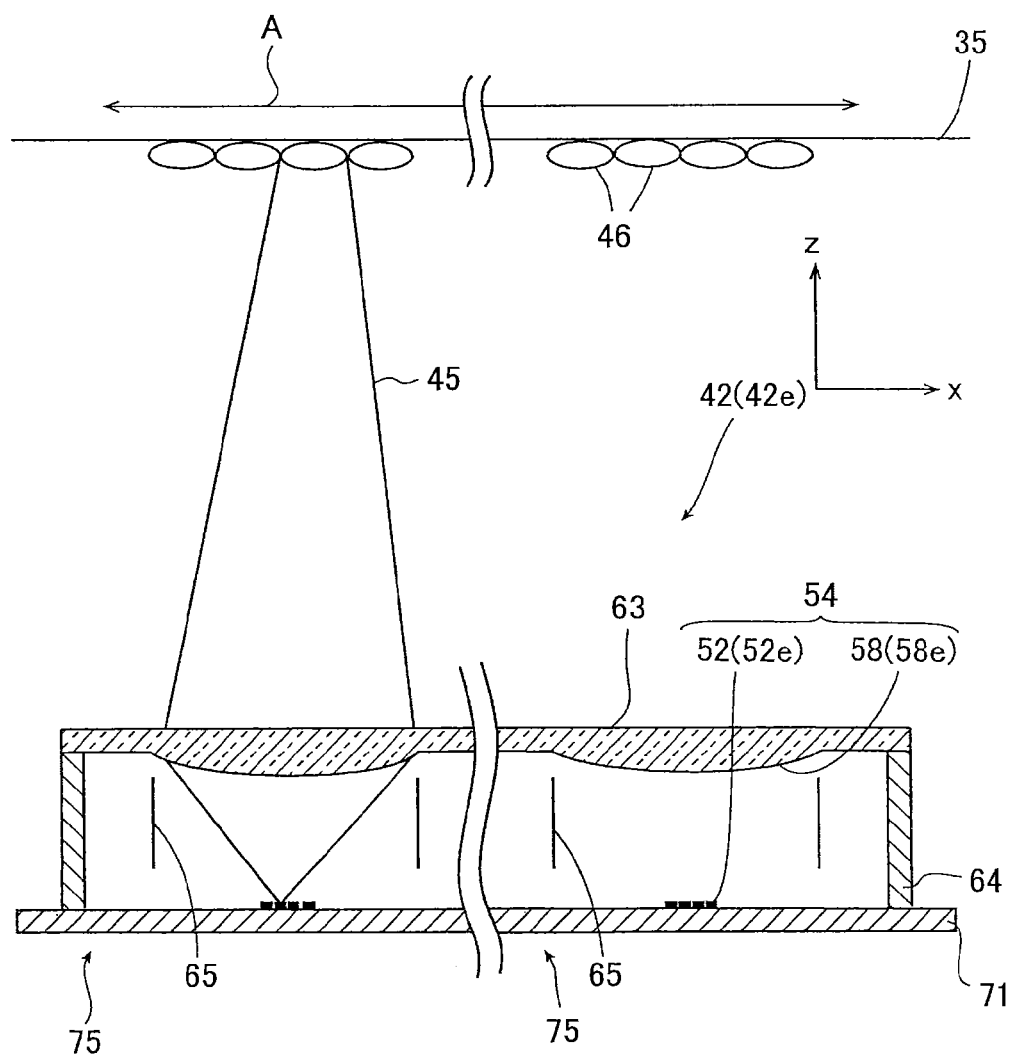
FIG. 14B is a schematic front view of the reflection type optical sensor shown in FIG. 14A from a light-emitting member in moving direction.

FIG. 14B is a schematic front view of the reflection type optical sensor 42 shown in FIG. 14A from the light-emitting member 52 in moving direction y.

Figure 14C:
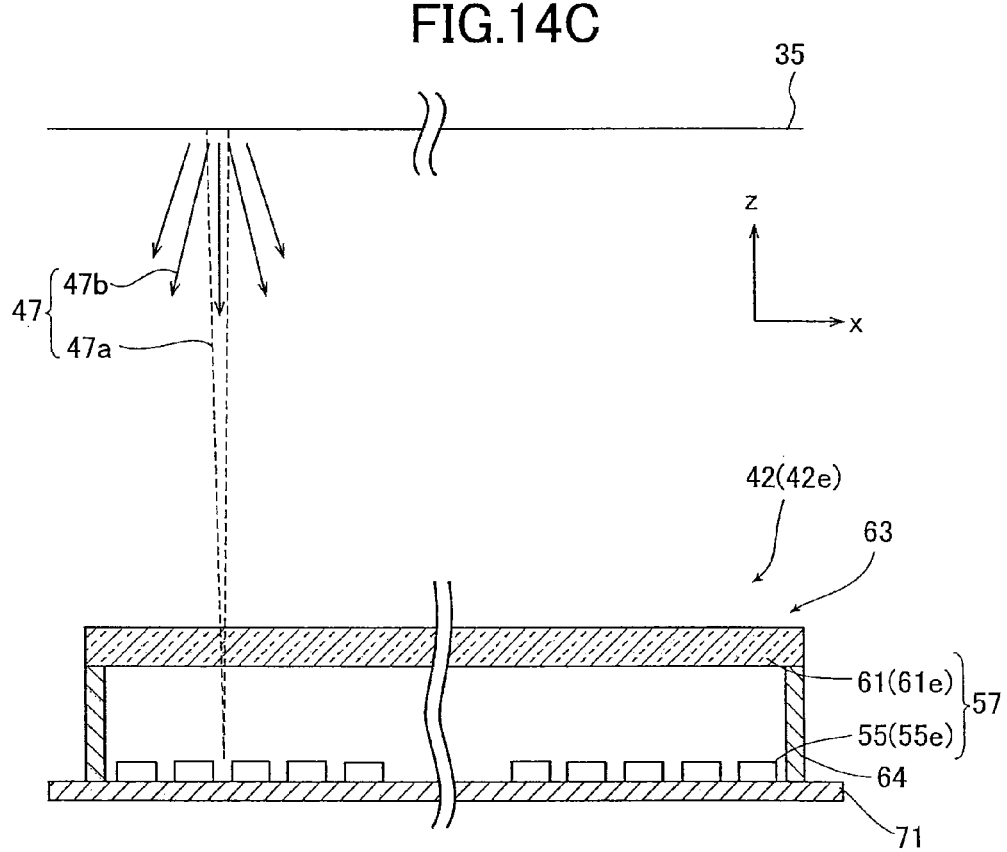
FIG. 14C is a schematic back view of the reflection type optical sensor shown in FIG. 14A from a light-receiving member in the moving direction

FIG. 14C is a schematic back view of the reflection type optical sensor 42 shown in FIG. 14A from the light-receiving member 55 in the moving direction y.

Figure 14D:
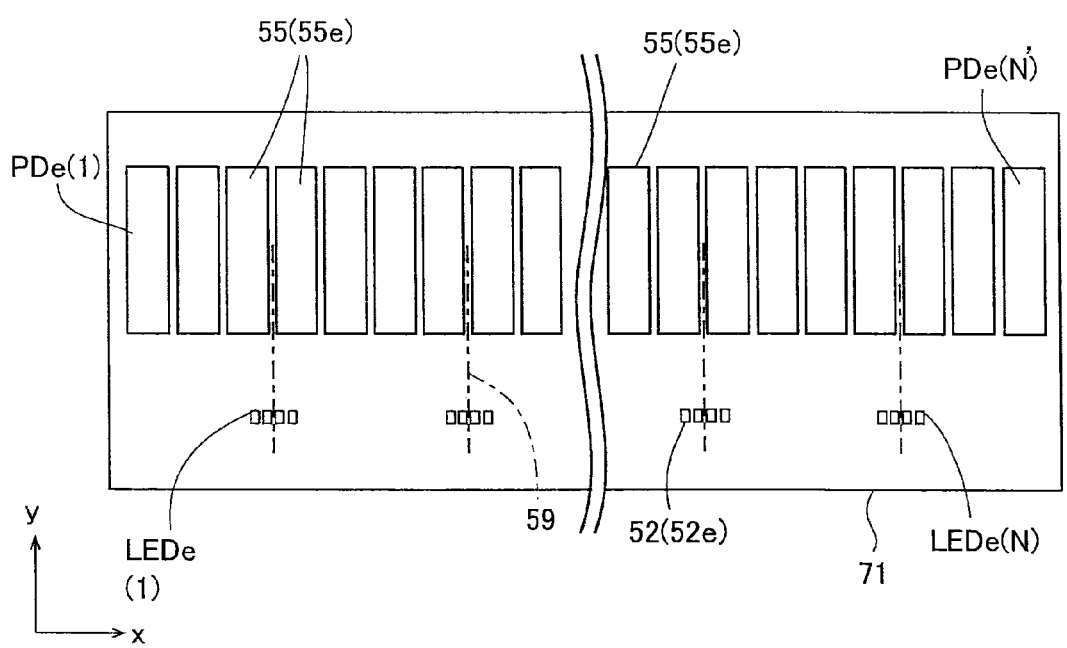
FIG. 14D is a schematic plan view of the board that supports a light-emitting member and a light-receiving member included in a reflection type optical sensor shown in FIG. 14A in the separating direction.

FIG. 14D is a schematic plan view of the board 71 that supports the light-emitting member 52 and the light-receiving member 55 in the separating direction z.

The present embodiment has the feature that the light-blocking member 65 is formed in the reflection type optical sensors 42 shown in each previous embodiments (of cause it is possible to use the light-blocking member 65 for the other embodiments).

As shown in FIG. 14A, the reflection type optical sensors 42 (particularly the reflection type optical sensor 42e) includes the light-emitting members 52 (particularly the light-emitting members 52e) that emits near infrared light, the light-emitting lens 58 particularly (the light-emitting lens 58e) arranged such that the light beam 45 emitted from the light-emitting member 52 is guided to illuminate the moving body (or the fixing belt 35) and forms an optical spot 46 on the surface of the fixing belt 35, the light-receiving lenses 61 (particularly the light-receiving lens 61e) that is arranged to guide the reflected light 47 reflected by the fixing belt 35 and a light-receiving member 55 (particularly the light-receiving member 55e) that detects the reflected light 47.

The light-emitting members 52 and the light-receiving member 55 are supported by (mounted on) identically same board 71. The board 71, the light-emitting lens 58 and the lens array 61 mentioned above are supported by a sensor body 64.

In the present embodiment, the light-blocking member 65 is set the reflection type optical sensors 42 to cut flare.

The flare is the light other than the reflected light 47 coming from the optical spots 46. The light other that the reflected lights 47 coming from the optical spots 46 means, for example, those of the reflected light 47 other than the optical spots 46 on the surface of the boding body, the reflected light 47 on the lens surface of the light-emitting lens 58 that is the light-emitting lens 58 corresponding to the light-emitting members 52 or on the surface of other light-emitting lens 58 that does not corresponds to the light-emitting member 52 which emits the light, etc.

The light-blocking member 65 is designed in such a way that it interrupts the adjacent light emitter units 75.

More concretely, the light-emitting members 52 are each set to interrupt between the space between the light-emitting member 52 and the light-emitting lens 58 and the external space thereof and also the bordering of these spaces.

The light-blocking member 65 is set between the light-emitting portion 54 and the detecting portion 57 as well.

In such structure, the light-blocking members 65 can be light-blocking surrounding walls formed in the sensor body 64 which has a formwork shape or can be a remaining wall of the sensor body 64 which is a thick formwork made from a drilled block that has two openings at the ends of the space and the remaining wall therebetween.

Using plastic press forming, such structure is made in a single body configuration with the light-blocking member 65 and the sensor body 64.

Using the light-blocking member 65 in the sensor body, the reflected light that is the light transmitting through the light-emitting lens 58 other than the light-emitting lens 58 corresponding to an arbitral light-emitting member 53 (which is an LED) which turns on the light and is reflected by the fixing belt 35 and the reflected light that is directly reflected on the surfaces of the light-emitting lens 58 corresponding to an arbitral light-emitting member 52 which turns on the light or else other light-emitting lens 58 are blocked to directly so that it is possible to precisely detect the surface condition of the fixing belt 35.

The Seventh Embodiment

In the reflection type optical sensor 42 shown in above each embodiment, as explained in the present embodiment, carrying out sequential turning-on/off of the light in the light-emitting members 52 such that each of a plurality of the light-emitting members 52 (which is LEDs) repeatedly turns on and off the light in sequential manor, the reflection type optical sensor 42 can precisely specify the positions of the scratches 52 on the surface of the moving body (or a fixing member such as the fixing belt 35) in the width direction.

The another interpretation of the "carrying out sequential turning-on/off of the light of the light-emitting members 52" is, for example, that each of a plurality of the light-emitting members 52 in the light emitter unit 75 repeatedly turns on and off the light in sequential manner and each light-emitting member 52 repeatedly carries turning-on/off the light from the right-hand side similar to the repetition as explained above after the light-emitting member 52 locating in the most left-hand side in the light emitter unit 75 completes to turning-on/off the light in case that the optical spot 46 is scanned on the moving body (the fixing belt 35) in the positive orientation (for example, from left hand side to the right hand side). This is as explained above, due to the relation of the correspondence between the light-emitting members 52 in the light emitter unit 75 and the optical spots made on the moving body (the fixing belt 35) is reverse against the width direction x. Of cause in the embodiments shown in FIGS. 5A to 5D, the sequential turn-on/off of the light in the light-emitting members 52 is carried out the light-emitting members 52 to sequentially turns on/off the light from the left-hand side to the right-hand side.

Once the sequential turning-on/off of the light carried out over all of the light-emitting members 52, the sequence is a single cycle. Such single cycle can be repeated in the sequential turning-on/off of the light explained above.

Carrying out such sequential turning-on of the light, it is possible to scan the optical spot 46 generated on the fixing belt 35 is scanned with the positive orientation in the width direction x.

The behavior of the light-receiving members 55 (which are PDs) while the optical spots 46 are scanned with the positive orientation in the width direction x is that a plurality of the light-receiving members 55 detects the reflected light 47 from the fixing belt 35 synchronous to turning-on of the light at LED(n) that is the n-th light-emitting member 52.

For the purpose of the simplicity, assuming the quantity of the light-emitting members 55 are 2m pieces, then the light detected by the light-receiving members 55 is done by 2*m* pieces of the light-receiving members 55, where m is an integer. The method of selecting 2*m* light-receiving members 55 is explained as follows.

It is not necessary that all of the light-emitting members 52 turning on/off the light from the left side to the right side are used. An arbitral N" (N" is equal to or less than N) pieces of the light-emitting members 52 may be used.

When LED(n) which is the n-th light-emitting member 52 turns on the light, the light-receiving member 55 which receives the maximum intensity of the receiving light among thereof and which receives the second maximum intensity of the receiving light are selected.

In most cases, the selected two light-emitting members 55 are adjacent in the arrangement. Assuming the center of the two light-receiving members 55 in the width direction be X=0, the rest 2m(2) light-receiving members 55 (which is a PD) locating in X=+/−1.51×P''' (l=1, 2, . . . , (m−1)) are selected.

The detected signals 48 that are opto-electronically converted by 2*m* light-receiving members 55 and amplified thereafter are sent to the surface condition judging device 43 upon receipt thereby.

In order to improve the precision of the detection, a method such that the detection results obtained from the above sequential turning-on/off of the light is carried out over a plurality of cycles and a process for averaging of the results of detection is executed.

The sequential turning-on of the light of a plurality in the light-emitting members 52 (which are LEDs) is controlled by a control signal sent from a surface condition judging device 34 (or the controller 44).

The Eighth Embodiment

The present embodiment features that, simultaneously turning on a plurality of light-emitting members 52 (which are LEDs) for simultaneously making a plurality of the optical spots 46, the line of the optical scanning in a single cycle in the width direction x is shortened.

For example, assuming the quantity of the light emitter units 75 be 9 pieces and the light emitter unit 75(1), the light emitter unit 75(2), . . . , the light emitter unit 75(9) be arranged in the positive orientation of the width direction x, the light-emitting members 52 (which are LEDs) of the light emitter unit 75(2) to the light emitter unit 75(8) turning-n the light when the surface condition of the moving body (or the fixing member as the fixing belt 35) is detected. In each light in emitter unit 75, the light-emitter unit 52 (2) is further arranged as an order of LED(1), LED(2), LED(3) and LED(4) in the positive orientation in the width direction x. The light-emitting member 52(3) of the light emitter unit 75 (2) is called light-emitting member LED(2-3).

FIG. 15A shows the distribution of the detection output from plurality of the light-receiving members 55 (which are PDs). The detection output is normalized as unity against the maximum value. The detections output from the light-receiving members 55 as (PD_1) to (PD_4) and those as (PD_15) to (PD_18) are zeros. Therefore, ten pieces of the light-receiving members 55 receive the reflected light 47 when light-emitting member LED(2-3) (or LED2-2) turns on.

When two of the light-emitting members 52 simultaneously turn on the light, it is necessary that the reflected light 47 due to other light-emitting members 52 turning on the light is not detected by the ten pieces of the light-receiving members 55 which are used for obtaining the detection results.

Therefore, it is necessary that two light-emitting remembers 52 separating in a certain range each other in the width direction x have to turn on the light when a plurality of light-emitting members 52 simultaneously turn on the light.

FIG. 15B shows the detection output of a plurality of the light-receiving members 55 when light-emitting members LED(2-3), LED(5-3) and LED(8-3) simultaneously turn on the light.

Three of the detection outputs, each similar detection output to that in the case that a single light-emitting member 52 turns on the light is obtained by three light-emitting members 52 each separated in long range simultaneously turn on the light. For the embodiment shown in FIG. 15B, it is understandable that the light-emitting member 52 (named as LED(1)) of the light emitter unit 75 (named as LED(2, 5, 8), the light-emitting member 52 (named as LED(2)) of the light emitter unit 75 (named as LED(2, 5, 8)9, the light-emitting member 52 (named as LED(3)) of the light emitter unit 75 (named as LED(2, 5, 8)9 and the light-emitting member 52 (named as LED(4)) of the light emitter unit 75 (named as LED(2, 5, 8)) can simultaneously turn on the light, the light-emitting member 52 (named as LED(1)) of the light emitter unit 75 (named as LED(3, 6)), the light-emitting member 52 (named LED(2)) of the light emitter unit 75 (named as LED(3, 6)), the light-emitting member 52 (named as LED(3)) of the light emitter unit 75 (named as LED(3, 6)) and the light-emitting member 52 (named as LED(4)) of the light emitter unit 75 (named as LED(3, 6)) can simultaneously turn on the light and the light-emitting member 52 (LED(1)) of the light emitter unit 75 (named as LED(4, 7)), the light-emitting member 52 (named as LED(2)) of the light emitter unit 75 (named as LED(4, 7)), the light-emitting member 52 (named LED(3)) of the light emitter unit 75 (named as LED(4, 7)) and the light-emitting member 52 (named LED(4)) of the light emitter unit 75 (named as LED(4, 7)) can simultaneously turn on the light.

It is possible to shorten the single cycle of the optical scanning line in the width direction x by simultaneously turning on the light of a plurality of the light-emitting members 52 separated in enough range each other. Then it is possible to shorten the time necessary for forming an image since the conveying speed of the fixing bet 35 is increased due to the shortening of the line cycle time.

It is preferable the light emitter unit 75 is constructed in accordance to the relation with the light-emitting members 52 simultaneously turning on the light. For example, the light-emitting members 52 that are in the same arrangement even for the different light emitter units 75 simultaneously turn on the light. The light-emitting members 52 that are in the same arrangement in the light emitter units 75 placing every two units simultaneously turn on the light such that the same light-receiving member 55 does not simultaneously detect a plurality of the reflected light beams 47.

The control of a plurality of the light-emitting members 52 (LED) simultaneously turning on the light is carried out by the control signal sent from the surface condition judging device 43 (or the controller 44).

The Ninth Embodiment

The present embodiment features that the optical spots 46 are generated with a arbitral tilted angle against the width direction x and the moving direction y as shown in FIG. 16B in contrast to that the optical spots 46 are generated along with the width direction x for the moving body (the fixing members as the fixing belt 35) in each embodiment previously discussed as shown in, for example, FIG. 16A.

The optical spots 46 tilting to the width direction x, it is possible to reduced the arrangement pitch of the optical spots 46 in the width direction.

More concretely, the reflection type optical sensors 42 are tilted against the width direction x and the moving direction y in the present embodiment in contrast that the reflection type optical sensors 42 are arranged in the direction of the width direction x in each of the previous embodiments.

The reflection type optical sensors 42 tilting to the width direction x and the moving direction y, it is possible to reduce the arrangement pitch of the optical spots 46 in the width direction.

In FIG. 16B, the reflection type optical sensors 42 are tilted with 45 degrees against the width direction x.

The reflection type optical sensors 42 being tilted with 45 degrees, the reflection type optical sensors 42 has better resolution of position in the detection results in comparison to the reflection type optical sensors 42 not being tilted since the arrangement pitch can be as little as 1/square root 2 times though the length of the width direction of the detection region A' is shortened to be 1/square root 2 times for the case of no tilting.

The tilting angle of the reflection type optical sensors 42 is not limited as that explained, smaller angles such as 0 degree to 45 degrees or larger angles as 45 degrees to 90 degrees are arbitrarily selected. The reflection type optical sensors 42 can be tilted to left down instead of right down of the schematic as shown in FIG. 16B.

The optical spots 46 are tilted by the reflection type optical sensors 42 themselves being tilted as explained above, however, other than such tiling, the light-emitting members 52 may be set in tilt angle in the reflection type optical sensors 42 with the arrangement that the reflection type optical sensors 42 is, for example, placed in parallel to the width direction x, or the light 45 may be deflected by using the light-emitting lenses 58 so that the arrangement pitch of the optical spots 46 in the width direction x is made smaller than the spacing between the light-emitting members in the arrangement direction.

In addition to the above tilting, the reflection type optical sensors 42 wherein the optical spots 46 are tilted are set by using the light-emitting members 52 further tilted in the reflection type optical sensors 42 or the light 45 deflected in use of the light-emitting lens 58.

When the light-emitting members 52 further are set with a tilting angle in the reflection type optical sensors 42, every light emitter systems (or the light emitter unit 75) can be set in a tilting angle.

The Tenth Embodiment

In the present embodiment, the reflection type optical sensors 42 are installed in the inside of the image generation apparatus 1 (see FIG. 1).

By setting the reflection type optical sensors 42 in the image generation apparatus 1, the detection of the scratches 51 on the moving body (or the fixing members as the fixing belt 35) in a real-time, which had been impossible before the present invention disclosed, and the detection of the position and the width of the scratches 51 on the fixing belt 35 are possible.

As explained in each above embodiment, optimizing light-receiving/emitting device (such as the light-emitting members 52 and/or the light-receiving members 55) for the use in the reflection type optical sensors 42 and optical system (light-emitting optical system 53 and light-receiving optical system 56) for use of the reflection type optical sensors 42, it is possible to improve the precision of the detection of the scratches 51 on the surface of the fixing belt 35 by increasing the intensity of the reflected light 47 from the fixing belt 35 with keeping the spacing of the adjacent optical spots 46 on the moving body (the fixing member as the fixing belt 35).

The Eleventh Embodiment

In the present embodiment, the reflection type sensors 42 are set near the width periphery position 35s of the small size blanks (recording media S) in the image generation apparatus 1.

When the length of the detection region A in the width direction is shortened, it is possible to include the width periphery position 35s of the blanks in the detection region A.

There is a merit to make it possible to compact the reflection type optical sensors 42 especially in the width direction x due to enabling to shorten the detection region A.

The widths of the scratches 51 being generally in the range of several hundreds of microns to several millimeters, the preferred length of the detection region A is 5 mm to 15 mm in the width direction x for the purpose of compacting the reflection type optical sensors 42.

It is possible to generally use a plurality size of the blanks such as A3, A4 and A5 for the image generation apparatus 1.

As a concrete example, the maximum size of the blanks is mostly the A3 size paper laid in longitudinal direction, smaller size blanks mean those small than A3 size.

If the image generation apparatus 1 can process the A2 size paper laid in longitudinal direction as the maximum size of the blanks, smaller size blanks mean those small than A3 size.

The reflection type optical sensors 42 can be set at the width periphery position 35s of the blanks which is the maximum size paper laid in longitudinal direction in the construction of the image generation apparatus 1.

Since there are two positions on the paper for the width periphery position 35s of the small size blanks, the reflection type optical sensors 42 can be placed each to each of both width peripheries of the blank, in other words two of the reflection type optical sensors 42 in the width direction x therefore the scratches 51 are made in both periphery sides of the blanks. However, since there is no large difference of the longitudinal streak scratches 51, which are due to both end surfaces of the blanks are evenly generated in both sides of the blanks, in between one side of the width ends and the other side thereof, it is satisfactorily enough to have the reflection type optical sensor 42 in either side thereof.

The Twelfth Embodiment

The present embodiment, the reflection type optical sensors 42 are enlarged to the width direction x in order to cover various size of blanks, as shown in FIG. 18.

When widening the refection type optical sensors 42 in the width direction, the image generation apparatus 1 can process A2, A3, A4, A5, B3, B4, B5 and B6 size blanks since the width periphery position 35s of all such size can be exposed to be irradiated by the reflection type optical sensors 42.

The Thirteenth Embodiment

In the present embodiment, the fixing belt 35 is used for the moving body.

By using the fixing belt 35 as the moving body, it is possible to precisely detect the surface condition of the fixing belt 35 using the reflection type optical sensors 42 as shown in the present invention.

A fuser roller 31 can be used for the moving body.

In addition, the embodiment of the reflection optical detection device in the above embodiment is not limited in the reflection type optical sensors shown in the above embodiments but those enabling to detect the reflect light are usable.

Though the reflection type optical sensors as described in the above embodiments have an array including a plurality of LEDs and a plurality of PDs which oppose each other, another structure of the reflection type optical sensor such that the laser beam out coming from the light-emitting members are deflected by optical defectors and one or a plurality of PDs receiving the laser beam which reflects on the fixing belt 35 can be used. As another preferred embodiment, a structure of the image generation apparatus wherein a reflection type optical sensor including an LED and a PD is driven to scan the primary direction of the fixing belt 35 can be used.

The detail technologies to accomplish the second purpose of the present invention are discussed in the following paragraphs.

The reflection type optical sensors regarding the present invention is used for an image generation apparatus and comprises reflection type optical sensors to detect the surface conditions of a moving body including a plurality of light emitter systems that have light-emitting members and a light-emitting optical system that have a plurality of light-emitting lenses and a light-receiving device including a light receiver systems that have light-receiving members receiving reflect light reflected on a moving body and light-receiving optical systems that have light-receiving lenses corresponding to the light-receiving members.

By forming the light-emitting lenses and the light-receiving lenses into a single element, the precision of the physical arrangement of each lens against each other one can be improved as well as improvement of the workability regarding the assembly of each lens. In such assembly process, it is preferable to form all of the light-emitting lenses and the light-receiving lenses into a single element. It is also preferable to compose a plurality of the single elements into which some of the light-emitting lenses and the light-receiving lenses are formed.

A plurality of the light-emitting lenses and the light-receiving lenses are aligned such that the centers of lenses are deviated from the optical axis. Using such alignment, it is possible to suppress the output variation of the light-receiving member resulting from angle deviation (especially the deviation of elevation angle) of the moving body against the reflection type optical sensors.

Setting a planner portion parallel to the optical axis at the border between the light-emitting lens and the light-receiving lens, the light (called "ghost light" hereinafter) other than that is necessary to detect the surface condition of the moving body can be reduced. Therefore the reflection type optical sensors regarding the present invention is excelling in the optical performance, preferred to be able to be used for the image generation apparatus etc. The "planner portion parallel to the optical axis" does not imply only the exact parallel to the optical axis but also substantively parallel thereto regardless to existence of unlevel surface of the planner portion, slight gradient in the parallelism etc. As will be explained, the major feature such that the ghost light other than that is necessary to detect the surface condition of the moving body is reduced is only preferred function thereof.

It is preferred that the light-emitting members of the light emitter systems are set to substantially have surface symmetry to the surface that includes the optical axis of the light-emitting lens corresponding light-emitting lens. By using such construction, it is possible to radiate the light with a substantially equal separation distance on the surface of the moving body. The surface symmetry is not exact one but includes substantive symmetry.

It is preferred that the reflection type optical sensors in the present invention is designed such that the light-receiving lenses are located farther for the light-receiver system for the optical axis in comparison to the light-emitting lenses. It is possible to make the curvature radius of the light-receiving lenses large by setting the light-receiving lens for the optical axis of the lens largely apart from the light emitter system. As the result, especially in the case when the moving body is especially a fixing member to fix the images, the output variation of the light-receiving members of the reflection type optical sensors due to the deviations of elevation angles of the fixing members can be preferably reduced.

For the reflection type optical sensors regarding the present invention, the light-receiving lenses are preferably cylindrical lenses that convert the light into an axial line. Using a single cylindrical lenses for the light-receiving lenses, the deviation of lens parameters (for example, curvatures of the lens radius, lens positions, lens thicknesses, etc.) among lenses can be removed, therefore it is possible to detect the surface conditions of the moving body.

Using cylindrical lenses that have no optical effects in the primary scanning direction for the light-receiving lenses, the deviation of the intensity distribution of the received light by the light-receiving members caused by the difference of the light emitter systems that turn on the light can be suppressed in comparison to the use of spherical lenses for the light-receiving lenses.

For the reflection type optical sensors regarding the present invention, it is preferred to set an open-end space between the light-emitting system and the light-emitting optical system. By setting the open-end space which is surrounded by a light-blocking surrounding wall, it is possible to prevent direct incidence of i) the light emitted through the light-emitting lenses other than the light-emitting lens corresponding to an arbitral light emitter system that turns on the light and ii) the directly reflected light on the surfaces of the light-emitting lenses other than that corresponding to the light emitter system that turns on the light (such directly reflected light is called "flare" hereinafter). Therefore, it is possible to precisely detect the surface condition of the moving body. In order to make such an open-end space, it is possible to use a step of a planner portion as the reference, the accuracy of the position thereof and the optical performance of the reflection type sensor can be improved.

It is preferred that the reflection type optical sensors regarding the present invention are to radiate the light to sequentially generate the optical spots on the surface of the moving body. Sequentially making a plurality of the optical spots, cross talk (a light-receiving member simultaneously receives the each reflected light reflected by each of a plurality of the light emitter systems) is removed in comparison to the case to simultaneously radiate the light to generate the optical spots at once.

The reflection type optical sensors of the present invention may have such a structure that the light-emitting members of a plurality of the light emitter systems may radiate light to simultaneously generate the optical spots on the moving body. Simultaneously generating a plurality of the optical spots, it is possible to shorten a line cycle (that is the time necessary to make all light emitter systems turning on the light). In order to detect the surface condition in a short time, it is possible to remove a missing detection to surely detect the scratches of the surface of the moving body. The light radiation in sequentially generating the optical spots is preferably selected to be effective to the purposes of the reflection type optical sensors, depths and/or widths of scratches, the environment conditions under which the reflection type optical sensors are used.

For the reflection type optical sensors of the present invention, it is preferable that a plurality of the optical spots is generated from the radiation from the light-emitting members of a plurality of the light emitter systems with arbitral angle against the detection direction of the surface of the moving body. For this purpose, the light emitter systems are aligned with a tilt angle against the detection direction of the moving body, in other words a tilt angle against the primary scanning direction or the optical spots are radiated in a line of arrangement thereof with a tilt angle even under the parallel alignment of the light emitter systems to the primary scanning direction. The arrangement pitch of the optical spots is different between the case that the optical spots are generated in a line parallel to the primary scanning direction and the case t the optical spots are generated in a line parallel to the primary scanning direction. It is possible to make the arrangement pitch of the optical spots relatively small in the case the optical spots are generated in a line parallel to the primary scanning.

The reflection type optical sensors regarding the present invention may be placed at or near the periphery end position of the recording media carried by the moving body or placed over the full width of the recording media. In such arrangement of the reflection type optical sensors, it is possible to compact the reflection type optical sensors since the detection region including the end portion can be small so that it is possible to easily improve the position resolution.

It is preferable that the length in the arrangement direction of a plurality of the light emitter systems is same as that of the length of moving body in the arrangement direction for the reflection type optical sensors regarding the present invention. In such construction, it is possible to have length of the reflection type optical sensors in the primary scanning direction long enough to process various sizes of blanks and surely detect the scratches even made at the different positions on the moving body due to the difference of the sizes of the blanks. The length in the arrangement direction of a plurality of the light emitter systems can be substantively same as that of the length of moving body in the arrangement direction for the reflection type optical sensors so that the detection of the scratches can be sufficiently carried out.

In the image generation apparatus of the present invention, the reflection type optical sensors as explained above of the good optical properties is used as the reflection type sensors that detect the surface conditions of the moving body to fix the image on recording media. Therefore, it is possible to precisely detect the surface condition and keep high precision image quality. Also it is possible to provide the image generation apparatus that can keep low maintenance cost since the exchange of the moving body is not frequently required.

For the image generation apparatus in the present invention, it is preferred that the moving bodies are fixing belts which have no peripheries. Since surface materials such as PFA (a trade mark of perfluoroalkoxy) or PTFE (a trademark of polytetrafluoroethylene) are used, the surface of fixing belt can easily get scratches in extreme frequency. However, using the reflection type optical sensors as previously explained in the present invention, it is possible to quickly detect the occurrence of the scratches with precise surface detection of the fixing belt. Therefore, it is possible to make such a countermeasure that the recording media do not pass through the region where the scratches exist on the surface of the fixing belt and therefore to use the fixing belt with good efficiency in terms of extending the term to exchange the fixing belts.

In addition to the first embodiment to the twelfth embodiment as explained above, further embodiments that are to achieve the second purpose of the present invention are explained in the following discussion.

The Fourteenth Embodiment

The fourteenth embodiment of the image generation apparatus of the present invention is explained referring to schematics. The present embodiment shows an example using a full color printer with tandem structure (simply called a "printer" hereinafter) to which the image generation apparatus is applied. The image generation apparatus in the present invention is not confined in color printers but also include copy machines, facsimile terminals, printing machines and complex machines that combine these functions. The printer in the present embodiment is to form images by using four toners such as a yellow, a cyan, a magenta and a black toners for which the image generation apparatus equips each member corresponding thereto. The members used for a yellow color, a cyan color, a magenta color and a black color are denoted with letters Y, C, M and BK at the numbers assigned to the members.

Figure 19:
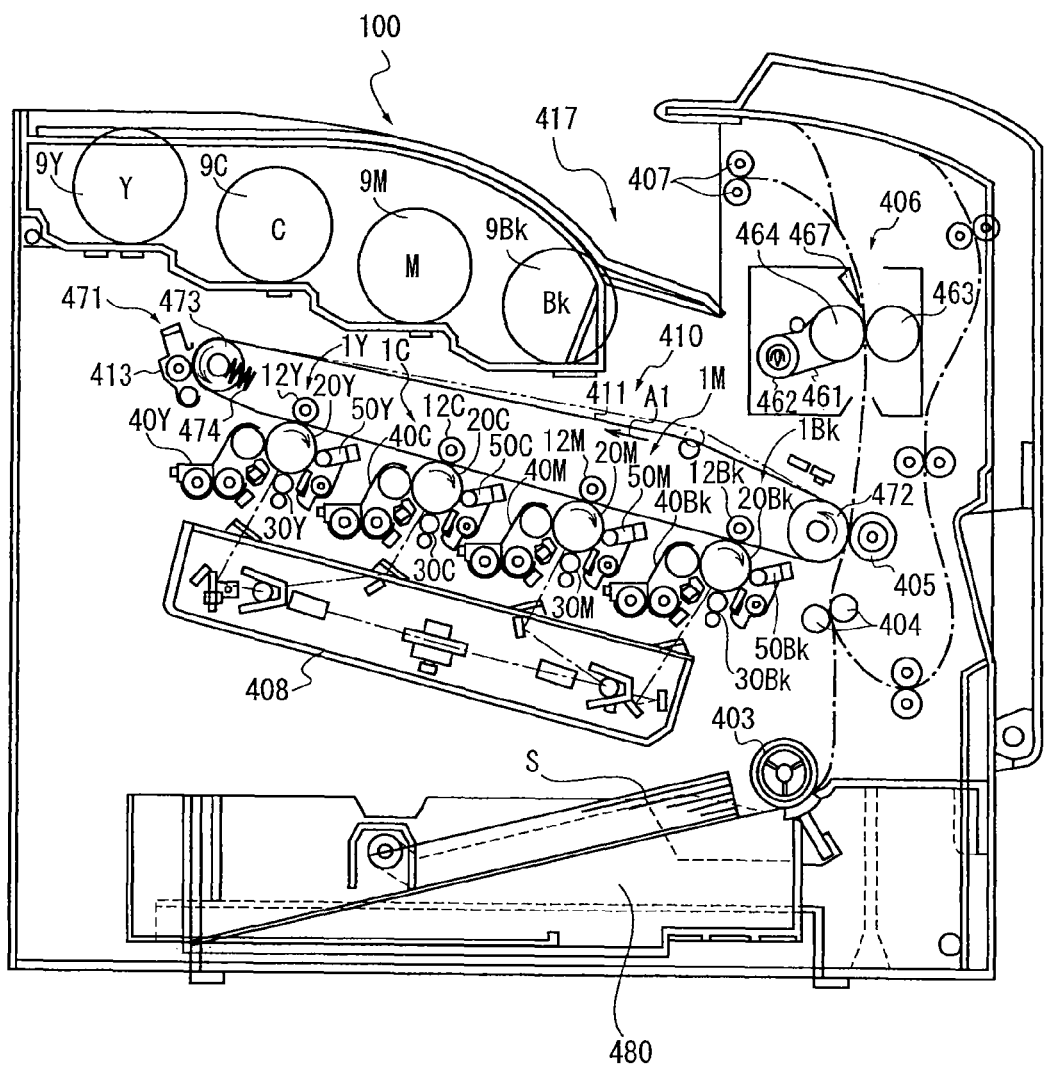
FIG. 19 is a schematic of overview of the image generation apparatus regarding the fourteenth embodiment.

As shown in FIG. 19, a tandem structure including photo receptor drums 20Y, 20C, 20M, 20BK as image carrier holders. Each of these photo receptor drums 20Y, 20C, 20M, 20BK can form each image corresponding to those decomposed in to yellow, cyan, magenta or black color.

The structure of the printer 100 of the present embodiment is explained in the following. As shown in FIG. 19, the printer 100 comprises four image stations 1Y, 1C, 1M and 1BK that carries out the process of charging and developing for colors as yellow, cyan, magenta and black corresponding to photo receptor drums 20Y, 20C, 20M, 20BK, respectively, an optical scanning device 408 for exposing device (that is optical writing device), an image transfer member such as an image transferring belt unit 410 and a secondary image transferring roller 5, an intermediate image transferring belt cleaning device 413, a fixing unit 406 for a fixing member, a reflection type optical sensor 200 as the reflection type optical detection device and a surface condition judging device 300 (see FIG. 20).

The printer 100 further comprises a sheet supply device 480 as a paper supply cassette to supply recording papers S as recording media, a pair of resist rollers 404 that convey the recording papers S a sensor (not shown in the figures) that detects the arrival of the front edge of the recording papers S at a pair of the resist rollers 404. The sheet supply device 480 carries recording papers conveyed toward between photo receptor drums 20Y, 20C, 20M, 20BK and an image transferring belt 411 to be explained later. A pair of resist rollers 404 sends the recording paper S carried by the sheet supply device 480 to meet a predetermined timing to form toner images by the image stations 1Y, 1C, 1M and 1BK to the transferring portion between each photo receptor drums 20Y, 20C, 20M or 20BK and an intermediate image transferring belt 411.

The printer 100 comprises a paper ejecting roller 407 that discharges the recording papers S that have been processed to fix the images to outside the main body of the printer 100, a paper ejecting tray 417, toner bottles 9Y, 9C, 9M and 9BK. The fixing unit 406 is to fix the toner image transferred to the recording paper S. The paper ejecting tray 417, being set in the upper part of the printer 100, carries the recording paper S ejected out from the printer 100 by the paper ejecting roller 407. The toner bottles 9Y, 9C, 9M and 9BK, being placed under the paper ejecting tray 417, are filled with yellow toner, cyan toner, magenta toner and black toner, respectively.

The image transferring belt unit 410, being opposingly placed above the photo receptor drums 20Y, 20C, 20M and 20BK, have the intermediate image transferring belt 411 and the primary image transferring roller 12Y, 12M 12C and 12BK. The secondary image transferring roller 405 is an image transferring roller opposed to the intermediate image transferring belt 411 and rotates in accordance with the rotation of an intermediate image transferring belt 411. The intermediate image transferring belt cleaning device is set against the intermediate image transferring belt 411 and cleaning the surface of the intermediate image transferring belt 411. The optical scanning devices 408 are set opposingly under the four image stations 1Y, 1C, 1M and 1BK.

The image transferring belt units 410 includes a driving roller 472 to which the intermediate image transferring belt 411 is engaged and a slave roller 473 as well, other than the intermediate image transferring belt 411 and the primary transferring rollers 12Y, 12C, 12M and 12BK.

The slave roller 473 has a function to add further tension to the intermediate image transferring belt 411. For this purpose, the salve roller 473 equips an additive tension device using springs. The second image transfer member 471 is constructed with such image transferring belt unit 410, the primary image transferring rollers 12Y, 12, C, 12M and 12BK, the secondary image transferring roller 405 and the intermediate image transferring belt cleaning device 413.

The intermediate image transferring belts 411, that is the first image transfer member (and working as the second image holding carrier), are placed at the positions corresponding to the photo receptor drums 20Y, 20C, 20M and 20 BK and visible images formed on the photo receptor drums 20Y, 20C, 20M and 20 BK transferred thereon can move toward the arrow sign A1 in FIG. 19. An endless belt is used for the intermediate image transferring belt 411. In the first transferring process, images are transferred in a superimposing manner onto the intermediate image transfer belt 411, wherein the images are batch-transferred to the recording papers used for the recording sheets via the secondary transferring process by using the second image transfer member 471.

The images being transferred in a superimposing manner to the intermediate image transferring belt 411 implies that each of the visible images formed on the photo receptor drums 20Y, 20C, 20M and 20BK is transferred to the same portion of the intermediate transferring belt 411 in an overlapping. For enabling such a transferring in a superimposing manger, each of the primary image transferring rollers 12, 12C, 12M and 12BK is place opposing to each of the photo receptor drums 20Y, 20C, 20M and 20BK via the intermediate image transferring belt 411. The image transfer using the primary image transferring roller 12Y, 12C, 12M and 12BK from the upper stream side to downstream side in the A1 direction by applying voltages with different timing.

The details being omitted to explain, the intermediate image transferring belt cleaning device 413 installed in the second image transfer member 471 opposes to the intermediate image transferring belt 411 and includes a cleaning brush and a cleaning blade. The cleaning brush and the cleaning blade clean the intermediate image transferring belt by striping to remove staying foreign materials such that residual toners etc. The intermediate image transferring belt has a discharge device (not shown in the figures) to bring out to dispose the removed residual toners.

As explained above, the printer 100 as shown in FIG. 19 has such a function that the color image superimposed is batch-transferred to the recording paper S via the secondary image transferring roller 405 by transferring the color images formed on photo receptor drums 20Y, 20C, 20M and 20BK each by each. However, the image generation apparatus regarding the present invention is not limited to the structure shown in the present embodiment but the structure such that the intermediate image transferring belt 411 holds the recording papers S and each color image on each of photo receptor drums 20Y, 20C, 20M and 20BK is directly superimpose to the recording papers S can be adopted.

The photo receptor drums 20Y, 20C, 20M and 20BK that generate images of yellow color, cyan color, magenta color and black color, respectively are arranged in this order from the upper stream of A1 paper passing. Around the photo receptor drums 20Y, 20C, 20M and 20BK, an image stations 1Y, 1C, 1M and 1BK that apply electrostatic-charging thereon and develop the images in the order of the rotation of photo receptor drums are placed. As the image station 1Y, 1C, 1M and 1BK, an electrostatic-charging device 30Y, 30C, 30M and 30BK, a developing device 40Y, 40C, 40M and 40 BK, a primary image transferring roller 12Y, 12C, 12M and 12BK and a cleaning device 50Y, 50C, 50M and 50 BK are placed in the rotation direction of the photo receptor drums 20Y, 20C, 20M and 20BK. For WRITE after electrostatic-charging, an optical scanning device 408 is used.

The optical scanning device 408 includes semiconductor laser devices, coupling lenses, f-theta lenses, toroidal lenses, mirrors and rotational polygon mirrors. The coupling lenses are to convert the laser light in to substantially parallel beams (called writing light Lb hereinafter). The writing light Lb is scanned by the mirrors of the polygon mirror in accordance to the rotation thereof and forms the optical spots on the surface of the photo receptor drums 20Y, 20C, 20M and 20BK via f-.theta lenses, toridal lenses and mirrors. The optical spots move in the longitudinal direction on the surface of the photo receptor drums 20Y, 20C, 20M and 20BK to scan the surface thereof. The optical scanning device 408 emits the writing light Lb to corresponding each of the photo receptor drums 20Y, 20C, 20M and 20BK and make an electrostatic latent image on the surface each thereof.

The sheet supply device 480 is set under the main body of the printer 100 and has convey roller 3 which contacts to the upper surface of the recording paper S. The recording paper S in the upper most position is conveyed to a pair of the resist roller 404 by driving to rotate the convey roller 3 in the counter clock wise.

For the fixing unit 406, a method of belt fixing is adopted. The system for such method comprises a fixing belt 461 (or 35), a heating roller 462 around which the fixing belt 461 is wrapped, a pressing roller 463 which opposes to the pressing roller 463 and a fuser roller 464 around which the fixing belt 461, opposing to the pressing roller 463, is wrapped. The detail structure of the fixing unit 406 is explained as follows.

Figure 20:
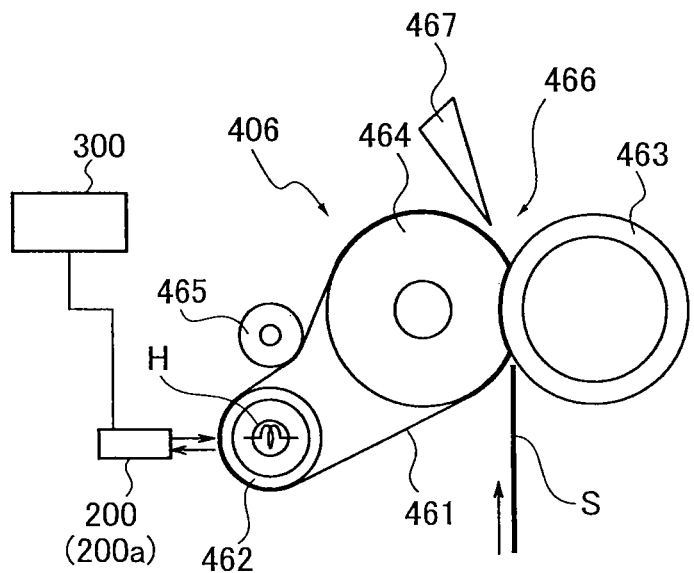
FIG. 20 is a schematic extended view of the fixing member shown in FIG. 19.

FIG. 20 shows the structure of the fixing unit 406. As shown in FIG. 20, the fixing unit 406 comprises the pressing roller 463 as a pressurizing body, the fixing belt 461 as a moving body, the heating roller 462 around which the fixing belt 461 is wrapped, the fuser roller 464 around which the fixing belt 61, opposing to the pressing roller 463, is wrapped, a tension roller 465 which adds tension to the fixing belt 464, a thermal sensor (not shown in the figures) to detect the temperature of a separation click 467 set at the downstream in the carrying direction of the recording paper S position at a nipping part and that of the fixing belt 461 on the heating roller 462.

The pressing roller 463 has an elastic layer made of silicon rubber etc. on the surface of a rod made of aluminum or iron etc. and a peel ply made of PFA or PTFE. The fixing belt 461 is a base material made of nickel or polyimide with a peel ply such as a surface layer of PFA or PTFE formed further thereon or that has further an intermediate elastic layer of silicon rubber between the base material and the surface layer. The fixing belt 461 is engaged to both the fuser roller 464 and the heating roller 462 which rotate therewith and keeps appropriate tension by externally pushing with the tension roller 465. The fuser roller 464 has a metal rod and a silicon rubber covering the surface thereof. The heating roller 462 has a hollow tube made of aluminum or iron and a heat source H such as halogen heater inside thereof.

The fixing unit 406 composing with these materials and elements forms the nipping part 466 that holds and carries the recording paper S. Once the recording paper S comes to the nipping part 466 from the downside and the image is fixed onto recording paper S by applying a pre-determined pressure and heat at the nipping part 466.

The tension roller 465 has silicon rubber on the surface of a metal rod. The separation click 467 has a sharp front edge facing and contacting to the surface of the fuser roller 464. A plurality of the separation clicks 467 are arranged in the direction of the axis (vertical direction from the page surface) of the fuser roller 464. The fixing unit 406 has a non-contacting thermal sensor (such as thermopile) as thermal sensor that monitors the temperature in non-contact to the fixing belt 461. The present invention is not limited to use such thermal sensor but a contacting thermal sensor (such a thermistor) that contacts with the fixing belt 461.

Figure 22:
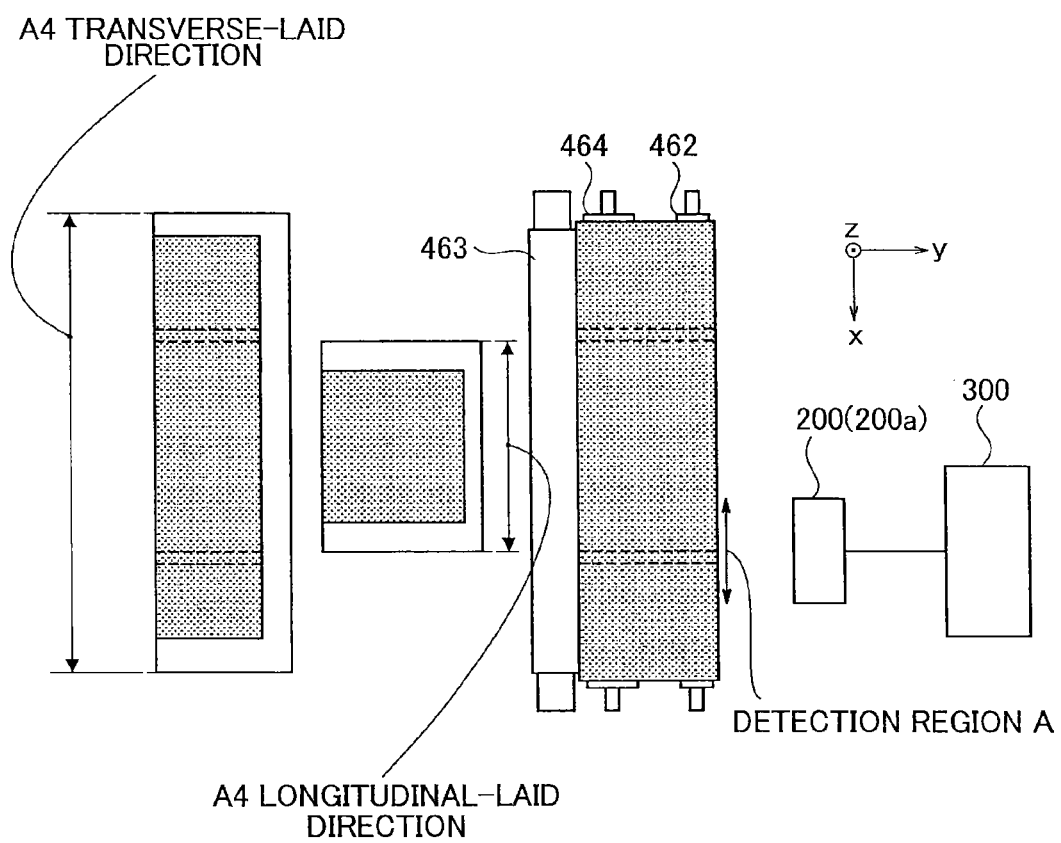
FIG. 22 is a schematic to explain the status when longitudinal streak scratches are generated on a fixing belt by an edge (or periphery) of A4 size paper in a longitudinal-laid direction.

As shown in FIG. 22, carrying out to repeat the fixing process for the A4 size paper laid in longitudinal direction using the fixing unit 406, longitudinal streak scratches are made at the positions, on the surface of the fixing belt 461, which are the longitudinal end peripheries of A4 conventional paper. Such streak scratches are made due to paper debris that is attached to both end peripheries of the paper and abrades the surface of the fixing belt 461. When a fixing process is carried out using A4 and/or A3 size paper laid in transverse direction, grazing streak comes out to the surface of the image corresponding to such longitudinal streak scratches. The appearance of this grazing streak degrades the quality of printed images.

Figure 21:
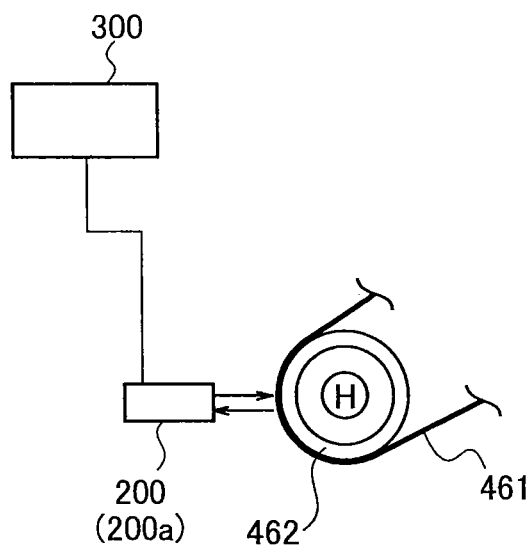
FIG. 21 is a schematic whole assembly view of the reflection type optical sensor and a surface condition judging device.

In order to solve this problem, the surface condition of the fixing belt 461 is judged by using the reflection type optical sensors 200 and the surface condition judging device 300. FIG. 21 shows the arrangement of the reflection type optical sensors 200 and the surface condition judging device 300. The reflection type optical sensors 200, as shown in FIG. 21, is placed in opposing to the fixing belt 461 on the heating roller 462.

The reflection type optical sensors 200 radiates the light and forms the optical spots in the primary scanning direction toward the surface of the fixing belt 461 and detect the reflected light from the fixing belt 461. The surface condition judgment device 300, being connected to the reflection type optical sensors 200, the judges the surface condition of the fixing belt 461 by receiving the detection signal from the reflection type optical sensors 200.

For the surface condition judging device 300, a main body controller device can be used to drive and control each portion or member of the printer 100. The main body controller device includes a CPU (a central processing unit) that executes various operations and drives and controls the portions of the printer 100, ROM (Read Only Memory) that stores fixed data such as computer executable programs, RAM (Random Access Memory) that functions as a working area of the data to freely be written or rewritten. The present invention is not limited to such a system construction but a separated controller device other than those installed in the main body is usable for the surface condition judging device 300.

FIG. 22 is a schematic to explain the status when longitudinal streak scratches in a view from the direction vertical to the axis (the primary scanning direction) of the heating roller 462. As shown in FIG. 22, a single device of the reflection type optical sensors 200 is, in the primary scanning direction on the fixing belt 461, set at the side of the end edge (called "edge portion" hereinafter) of the width direction of the blanks set in an A4 longitudinal-laid direction. The reflection type optical sensors 200 form a long detection region A on the fixing belt 461 by radiating the light to form a plural of the optical spots. According to such setting up, it is not necessary to rigorously keep the relative positional relation between the reflection type optical sensors 200 and the edge periphery portion of the blanks in the primary scanning direction since the reflection type optical sensors 200 form such a long detection region A.

The surface condition judging device 300 can detect the surface condition of the detection region A, which is long in the primary scanning direction, by receiving the detection signals from the reflection type optical sensors 200. When the edge portion of the blanks is included in the detection region A, the levels and/or the positions of longitudinal streak scratches made at the edge periphery portion of the blanks is, for the purpose of quantification, defined as the surface conditions of the fixing belt 461. The details for the quantification will be explained later. The levels of scratches represents the degree of the scratches, so that implies the depths (or roughness) and widths (magnitudes) of the scratches.

(Structure of the Reflection Type Optical Sensors)

The principal structure of the reflection type optical sensors 200 (or 200a) regarding the fourteenth embodiment is shown in FIGS. 23A and 23B. The x direction is the primary scanning direction of the fixing belt 461, the y direction is the secondary scanning direction, z is a direction vertical to the x-y plan and the direction of the reflection type optical sensors 200a directs an opposing direction to the fixing belt 461. The relation of the relevant directions is same as in the following embodiments or the examples for comparison.

FIG. 23A is a schematic cross-sectional view of the reflection type optical sensor regarding the fourteenth embodiment observed in the primarily scanning direction. As shown in FIG. 23A, the reflection type optical sensors 200a regarding fourteenth embodiment comprises a light-emitting diode (called an LED hereinafter) 211a, a light-emitting optical system having light-emitting lenses 221a arranged to guide the emitted light to the fixing belt 461 and generate optical spots SP, light-receiving lenses 222a guiding the reflected light reflected by the fixing belt 461, a light-receiving optical system having photo diodes (called PDs or a PD for a singular hereinafter) 212a, a board 210a supporting the LED 211a and a PD 212a and a case 240a to hold the board 210a and the lens array 220a. At the boarder portion of the light-emitting lenses 221a and the light-receiving lenses 222a, a step 223a is formed at the planner portion parallel to the optical axis.

A lens array 220a is an element made in such a way that plurality of light-emitting lenses 221a and a single light-receiving lens 222a are arranged in two dimensional arrays and formed into a single element.

Figure 24:
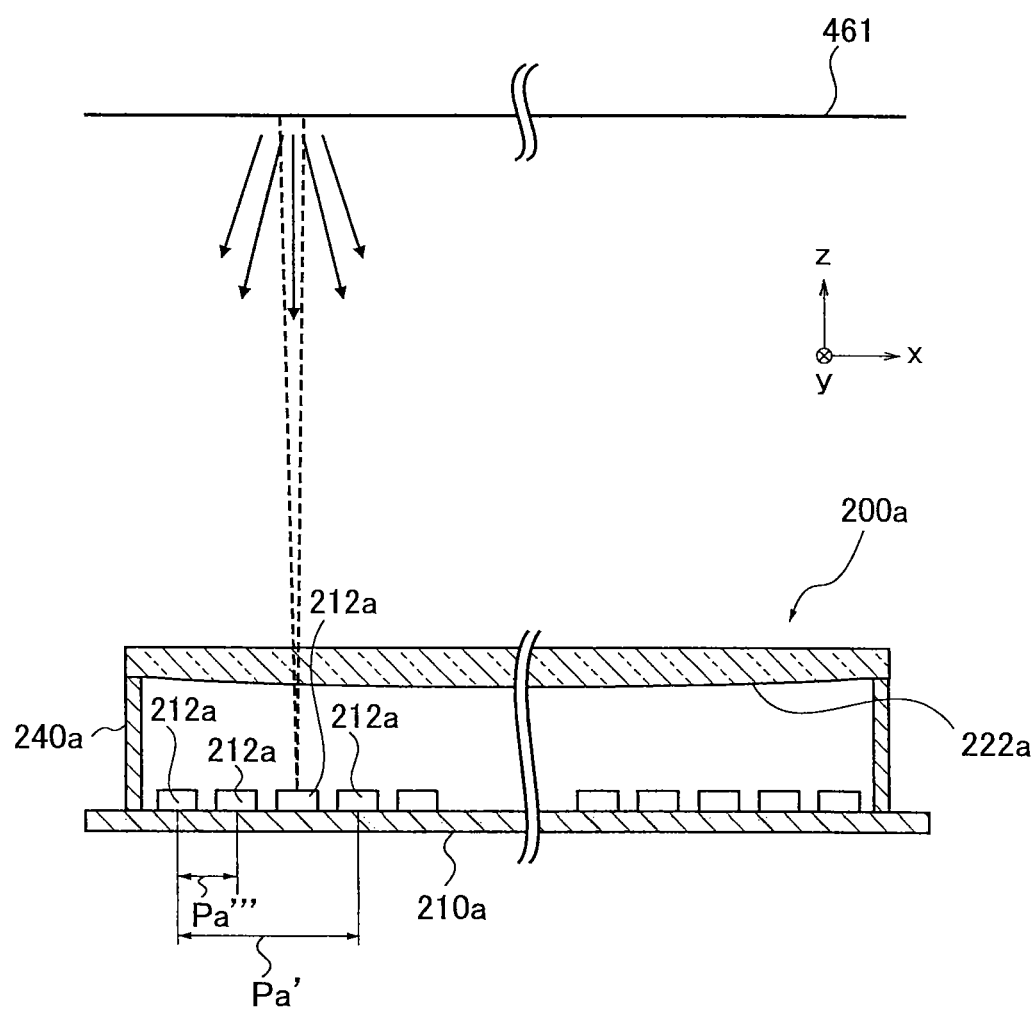
FIG. 24 is a schematic of FIG. 23A is a schematic of a cross-sectional view of a PD and light-receiving lens included in a reflection type optical sensor regarding the fourteenth embodiment scanned in the secondarily scanning direction for the purpose of explaining a structure thereof.
Figure 25:
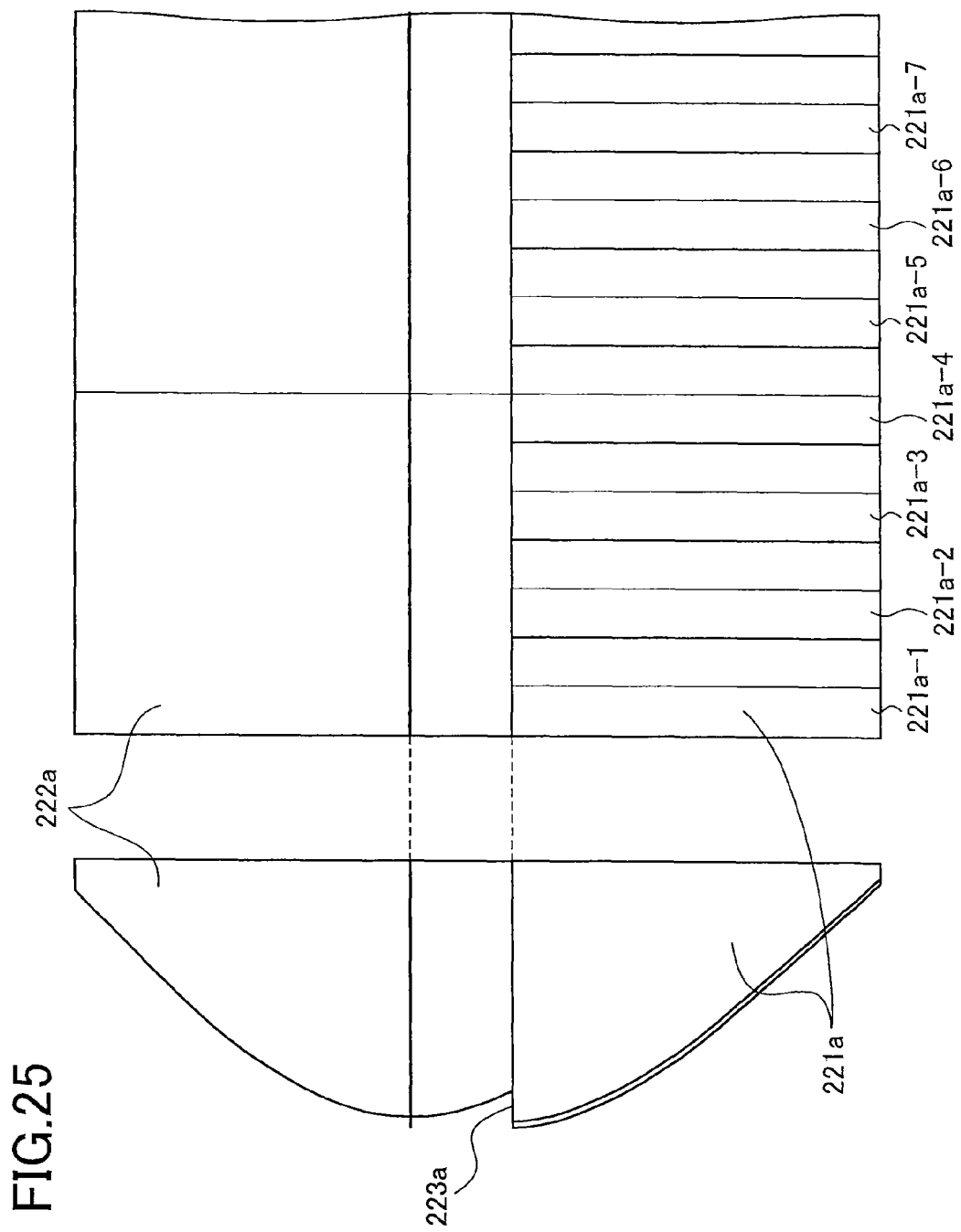
FIG. 25 is a schematic to explain details of as structure of a lens array included in a reflection type optical sensor used for the fourteenth embodiment.
Figure 26:
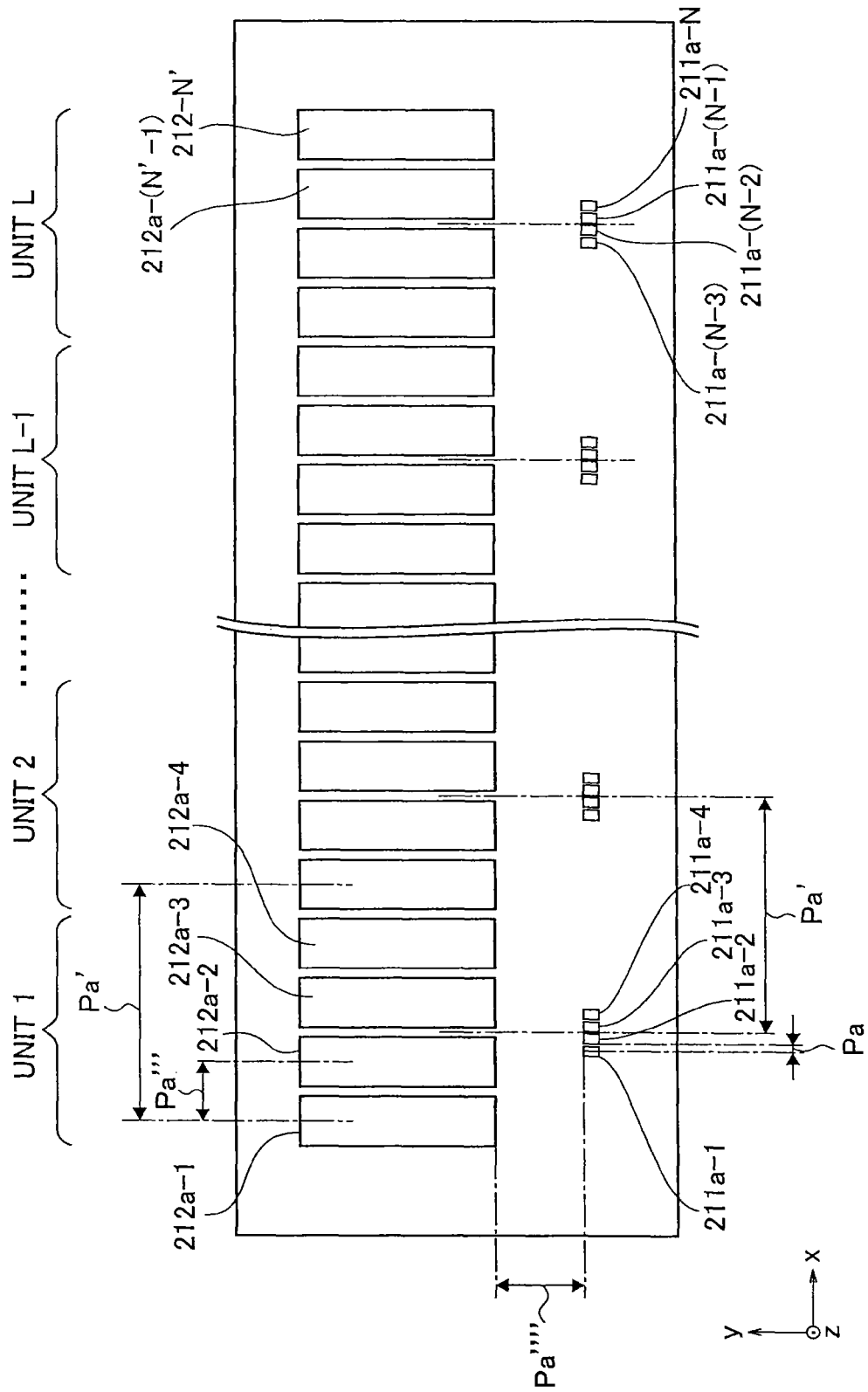
FIG. 26 is a schematic plan view of the board that supports an LED and a PD used for the fourteenth embodiment.

FIG. 23B is a schematic cross-sectional view of the reflection type optical sensor shown in FIG. 23A in the secondary scanning direction (y direction). FIG. 24 is a schematic cross-sectional view of the PD 212a and the light-receiving lenses 222a used for the reflection type optical sensors 200a observed in the secondary scanning direction (y direction). FIG. 25 is a schematic of the details of the light-emitting lenses 221a and the light-receiving lenses 222a. FIG. 26 is a schematic plan view of a board that supports an LED 211a and the PD 212a. For the cross-sectional views as shown in FIGS. 23A, 23B and 24, the portion in the front page surface of the case 240a is removed and the portion of the back side is omitted. Same removal and omission are taken place in the following embodiments.

As shown in FIGS. 23A and 26, the plurality of LED 211a is placed in the primary scanning direction. One light-emitting lens 221a corresponding to the four LEDs 211a are placed. The lens diameter in the primary scanning direction of the light-emitting lens 221a is 2.4 mm. The arrangement pitch of the four LEDs 211a is P (see FIG. 26). As shown by a dotted line in FIG. 23B, four LEDs 211a emits light of which beams are symmetry against the optical axis of the light-emitting lenses 221a. In the present embodiment, the light from the first LED and the light from the fourth LED are symmetry against the optical axis and the light from the second LED and the light from the third LED are symmetry against the optical axis as well. Therefore it is possible to generate the optical spots SP as those in a train with substantially equivalent distances (or distance P") on the surface of the fixing belt 461.

When the surface condition of the fixing belt 461 is detected in the reflection type optical sensors, the distance or the angel of the surface of detection against the reflection type optical sensors 200a are deviated due to ruffling, floppy or curling of the fixing belt 461. It is difficult to completely remove such deviation. Therefore, there is a problem that precise detection is scarcely possible since the output of detection signal does not reflect the correct output to detect the surface condition of the fixing belt 461. Especially there is a problem that the influence of the variation of angles due to the surface waving (called "waving angle" hereinafter) is remarkably large.

For the reflection type optical sensors 200a regarding the fourteenth embodiment, anamorphic lenses that have different optical power ratio for the primary scanning direction and the secondary scanning direction is adopted as shown in FIGS. 23A and 23B. Using anamorphic lenses, it is possible to optimize the curvature radii of the lenses in secondary scanning direction with keeping the spot diameter of optical spot SP (therefore a diameter of the optical beam thereof) in a predetermined condition on the fixing belt 461. Therefore, it is possible to decrease the fluctuation of the output of the light-receiving members when the waving angle due to the surface waving of the fixing belt 461. As the result, it is possible to avoid the degradation of the precision of the detection using the reflection type optical sensors 200a and keep good optical characteristic thereof.

The reflection type output sensors 200a in the fourteenth embodiment have following three differences against the reflection type optical sensors 200' that will be explained later, wherein the second item (2) is the major feature thereof. That is:

(1) no light-blocking surrounding walls are used,
(2) the light-emitting lenses 221a and the light-receiving lenses 222a are placed to have different optical axes, (3) the lens parameters (as curvature radii, lens diameters, lens thicknesses, the center-to-center distance between the light-receiving system and the light-emitting lens and the center-to-center distance between the light-receiver system and the light-receiving lens)) are different.

The light-emitting lenses 221 as mentioned in (1) and the light-receiving lenses 222a are different of 0.25 mm regarding the lens center in the direction of the optical axis, therefore the light-emitting lenses 221a are placed closer to the light emitter systems (the LED 221a) in the optical axis direction.

To concretely explain the lens parameters, the curvature radius of the light-emitting lenses 221a is 4.6 M mm in the primary scanning direction, a conical constant is 0 in the primary scanning direction. The curvature radius and conical constant of the light-emitting lenses 221a is 4.3 mm and −2.0 in the secondary scanning direction, respectively, the diameters of the light-emitting lenses 221a are 2.4 mm and 9.2 mm in the primary and secondary scanning directions, respectively and the thickness of the light-emitting lenses is 6.6 mm.

The curvature radius of the light-receiving lenses 222a is 50 mm in the primary scanning direction, a conical constant is −1.0 in the primary scanning direction. The curvature radius and conical constant of the light-receiving lenses 222a is 4.8 mm and −1.6 in the secondary scanning direction, respectively, in the secondary scanning direction, the diameters of the light-receiving lenses 222a are 17 mm and 0.9 mm in the primary and the secondary scanning directions, respectively and the thickness of the light-emitting lenses is 6.35 mm.

The center-to-center distance of the light-emitting lenses 221a and the light-receiving lenses 222a is 2.53 mm in the secondary scanning direction. The center-to-center distance between the light-emitting systems (the LED 211a) and the light-emitting lenses 221 is 10.37 mm in the optical axes and the center-to-center distance between the light-receiver system (the PD 212a) and the light-receiving lenses 222a is 10.62 mm in the optical axis direction. In such center-to-center distances, as mentioned previously, the light-emitting lenses 221a and the light-receiving lenses 222a are different in the lens center positions as deviated 0.24 mm.

A combination of four LEDs 211a and the light-emitting lens 221a is called a unit hereinafter. Placing the plurality of units in the primary scanning direction, the unit constructs the light-emitting device of the reflection type optical sensors 220a (such as a light-emitting system plus a light-emitting optical system). As shown in 26, the arrangement pitch of the unit in the primary scanning direction is P' and the arrangement of the units is unit 1, unit 2, . . . , unit L from the left of the page of FIG. 26. Though it is possible to place the plurality of units, we confine the quantity of units in seven ones (so that L=7) in the present embodiment, the following embodiments and the examples for comparison.

The light emitted from each of LEDs 211 radiates the surface of the fixing belt 461 to generate optical spot SP through the corresponding the light-emitting lens 221a. Therefore, the plurality of optical spots SP is generated on the surface of the fixing belt 461 with an arrangement of pit P''' in the direction of the primary scanning direction as shown in FIG. 23B.

FIG. 24 is a schematic back view of the PD 212a of the reflection type optical sensors 200a shown in FIG. 23A and the light-receiving lenses 222 in a reflection of the secondary scanning direction (y direction). As shown in FIGS. 24 and 26, a plurality of PDP 212a are arranged in the primary scanning direction opposing to the LED 211a, wherein, the arrangement pitch of the primary scanning direction is Pa'''. The reflection type optical sensors 200a has a pit Pa''' (which is the arrangement pitch of the PD 212a) which is nearly equals to the Pa'' (which is the arrangement pitch of optical spot SP) being further nearly equal to a quarter of the arrangement pitch of the unit.

For the light-receiving lenses 222a, an anamorphic lens that has different optical power ratio for the primary scanning direction and the secondary scanning direction is used. When the optical spots SP is generated on the surface of the fixing belt 461 in the primary scanning direction when the light is emitted from the LED 211a, a reflected light from the surface of the fixing belt 461 is generated. Since the surface of the fixing belt 461 is not mirror surface, the reflected light includes a scattering light component is generated in addition to the nominal reflecting light component. Therefore, the part of the reflected light is guided into the light-receiving lenses 22a and detected by the PD 212a.

FIG. 26 is a schematic plan view of a board 210a that supports an LED 221a and a PD 212a in a view of z direction. The LED 211a is arranged with a pitch Pa in the primary scanning direction in a unit and with a pitch Pa' in the primary scanning direction between the adjacent units. The PD 212a is arranged with a pitch Pa'' in the primary scanning. The pitch between the LED 211a and the PD 212a is Pa''''. Each of the LED 211a is named as LED 211a-1, LED 211a-2, . . . , LED 211a−(N−1), LED 211a-N (since the quantity of units is seven, these names are actually LED 211a-1 to LED 211a-28) from the left-hand side of FIG. 26 toward the positive orientation in x direction and in the similar manner, each of the PD 212a as PD 211a-1, PD 211a-2, . . . , PD 211a−(N'−1), LED 211a-N' (named actually (LED 211a-1 to LED 211a-28).

An Example for Comparison

Structure of the Reflection Type Optical Sensors

Using FIGS. 28A to 31, the reflection type optical sensors 200' as given as an example for comparison is concretely discussed. The structure of the reflection type optical sensors 200' given as an example for comparison has the same structure as the fourteenth embodiment with differences as described below. The same structure is not explained but the differences from the fourteenth embodiment are only discussed in the following.

The differences are;
(1) the reflection type optical sensors 200' have light-blocking members,
(2) the light-emitting lenses 221' and the light-receiving lenses 222' are arranged in the same position in the optical axial direction, and
(3) the lens parameters (curvature radii, lens diameters, lens thicknesses, light emitting systems), the center-to-center distance to the light-emitting lenses and the center-to-center distance between the light receiver system and light-receiving lenses.

Figure 28A:
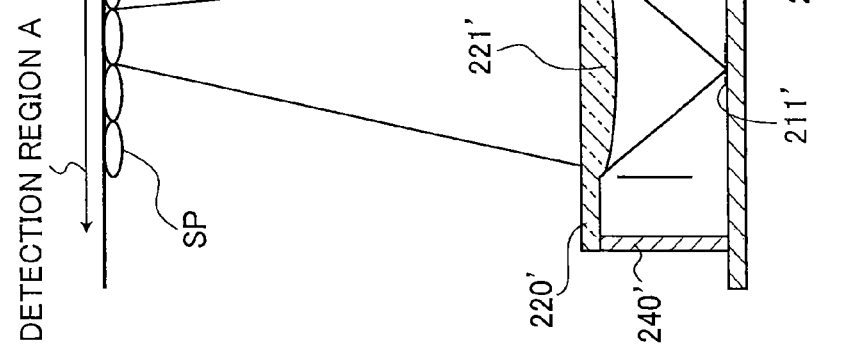
FIG. 28A is a schematic cross-sectional view of the reflection type optical sensor scanned in the primarily scanning direction for the purpose of explaining a structure thereof.
Figure 28B:
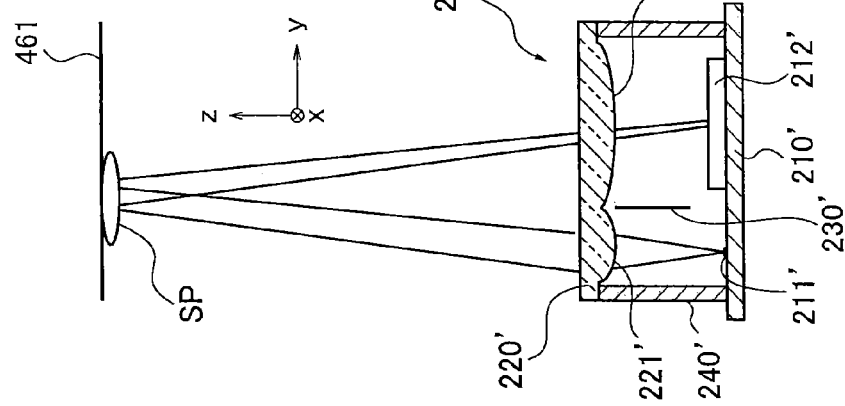
FIG. 28B is a schematic cross-sectional view of the reflection type optical sensor scanned in the secondarily scanning direction for the purpose of explaining a structure thereof.
Figure 29:
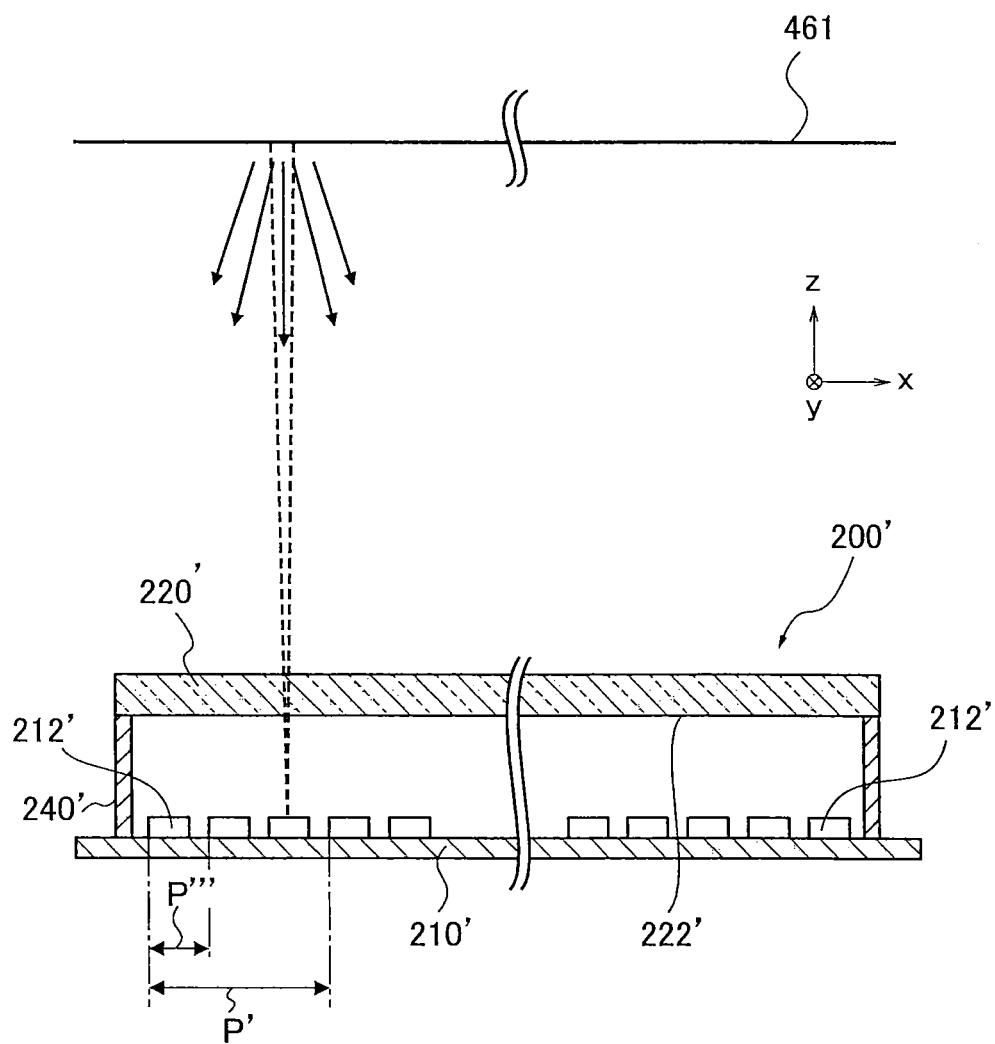
FIG. 29 is a schematic cross-sectional view of a PD and a light-receiving lens included in the reflection type optical sensor given as an example for comparison.
Figure 30:
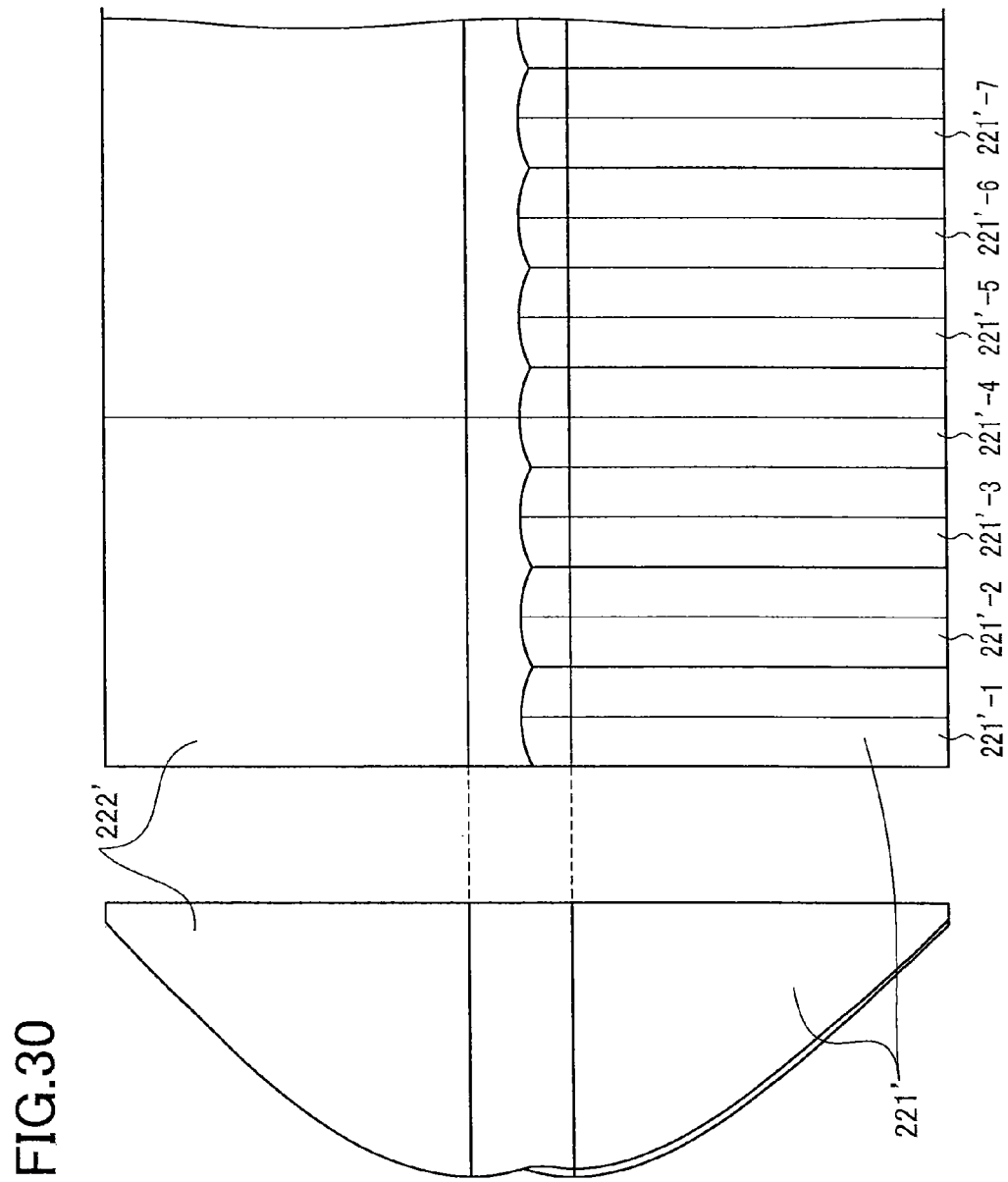
FIG. 30 is a schematic to explain a structure of a lens array included in the reflection type optical sensor given as an example for comparison.
Figure 31:
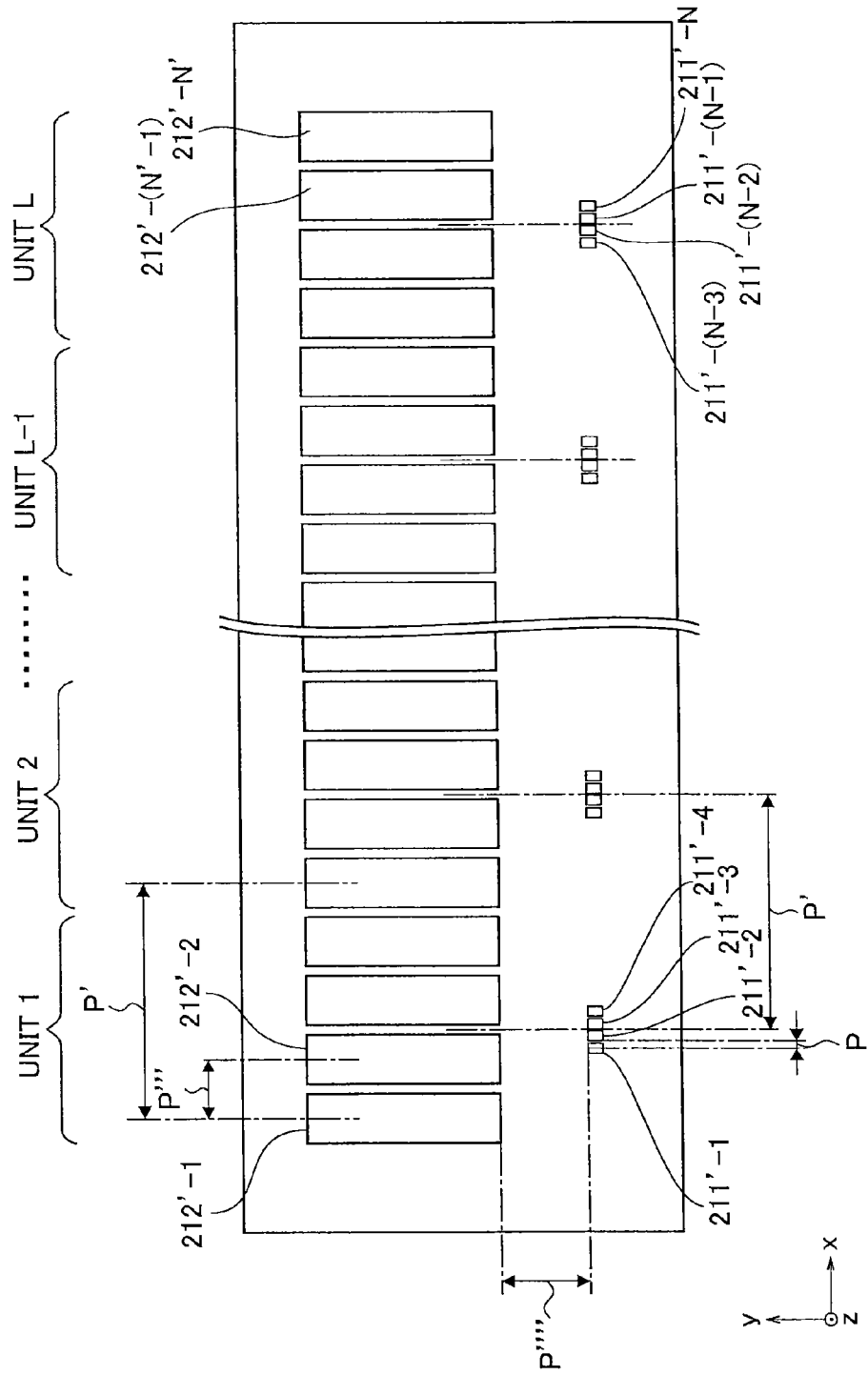
FIG. 31 is a schematic of plan view of a board that supports a light-emitting diode (an LED) and a photo diode (a PD) give as an example for comparison.

FIG. 28A is a schematic of a conceptual cross-sectional view of a reflection type optical sensor 200' scanned in the primarily scanning direction (x direction). FIG. 28B is a schematic of a conceptual cross-sectional view of the reflection type optical sensor 200' scanned in the secondarily scanning direction (y direction). FIG. 29 is a schematic cross-sectional view of a PD 212' and the light-receiving lenses 222' included in the reflection type optical sensor 200' in the secondary scanning direction (y direction). FIG. 30 is a schematic to explain a structure of the lens array 220' included in a reflection type optical sensor 200'. FIG. 31 is a schematic of plan view of the board that supports an LED 211' and a PD 212'.

As shown in FIGS. 28A to 31, the reflection type optical sensors 200' regarding the example for comparison comprises an LED 221' as the light emitter systems, a light-emitting lens 221' arranged to emit the light to generate the optical spots SP on the surface of the fixing belt 462, a photodiode (a PD 212') working as the light receiver system to receive the reflected light being guided by the light-receiving lenses 222, a lens array 220' formed into a single element from the light-emitting lenses 221' and the light-receiving lenses 222', a case to hold the board 210' and the lens array 220' and the light-blocking surrounding wall to prevent the flare.

The light-blocking surrounding walls 230' that prevent to detect the flare is placed between the LED 211' and the light-emitting lens 221' in the primary scanning direction. The light-blocking surrounding wall 230' and the case 240' are formed into a single element.

FIG. 30 is a schematic to show the detail structure of the lens array 220' included in the reflection type optical sensor 200'. The lens parameters of the light-emitting lenses 221' are 4.6 mm curvature radius in the primary scanning direction and 0 conical constant in the primary scanning direction. The curvature radius of the light-emitting lenses 221 in the secondary scanning direction is 4.3 mm and the conical constant in the secondary scanning direction is −2.0. The lens diameter of the light-emitting lenses 221' is 2.4 mm and 10.5 mm in the primary and secondary scanning directions, respectively and the lens thickness is 6.6 mm.

The curvature radius and the conical constant of the light-receiving lens 222' in the primary scanning direction are 50 mm and −1.0, respectively. The curvature radius and the conical constant of the light-receiving lenses 222' in the secondary scanning direction is 4.8 mm and −1.6, respectively. The lens thickness of the light-emitting lens 221' is 6.6 mm and the lens diameters of the light-emitting lens 221' are 2.4 mm and 10.5 mm in primary and secondary scanning directions, respectively.

The center-to-center distance (or the optical axis distance, i.e. the distance between two optical axes) between the light-receiving lenses 221' in the secondary scanning direction and light-receiving lenses 222a is 2.53 mm. The center-to-center distance between the light emitter systems and the light-emitting lens 221' in the optical axis which is equal to the center-to-center distance between the light receiver system and light-receiving lens 222' is 10.4 mm.

(First Example of the Operation of the Reflection Type Optical Sensors Regarding the Fourteenth Embodiment)

Figure 32:
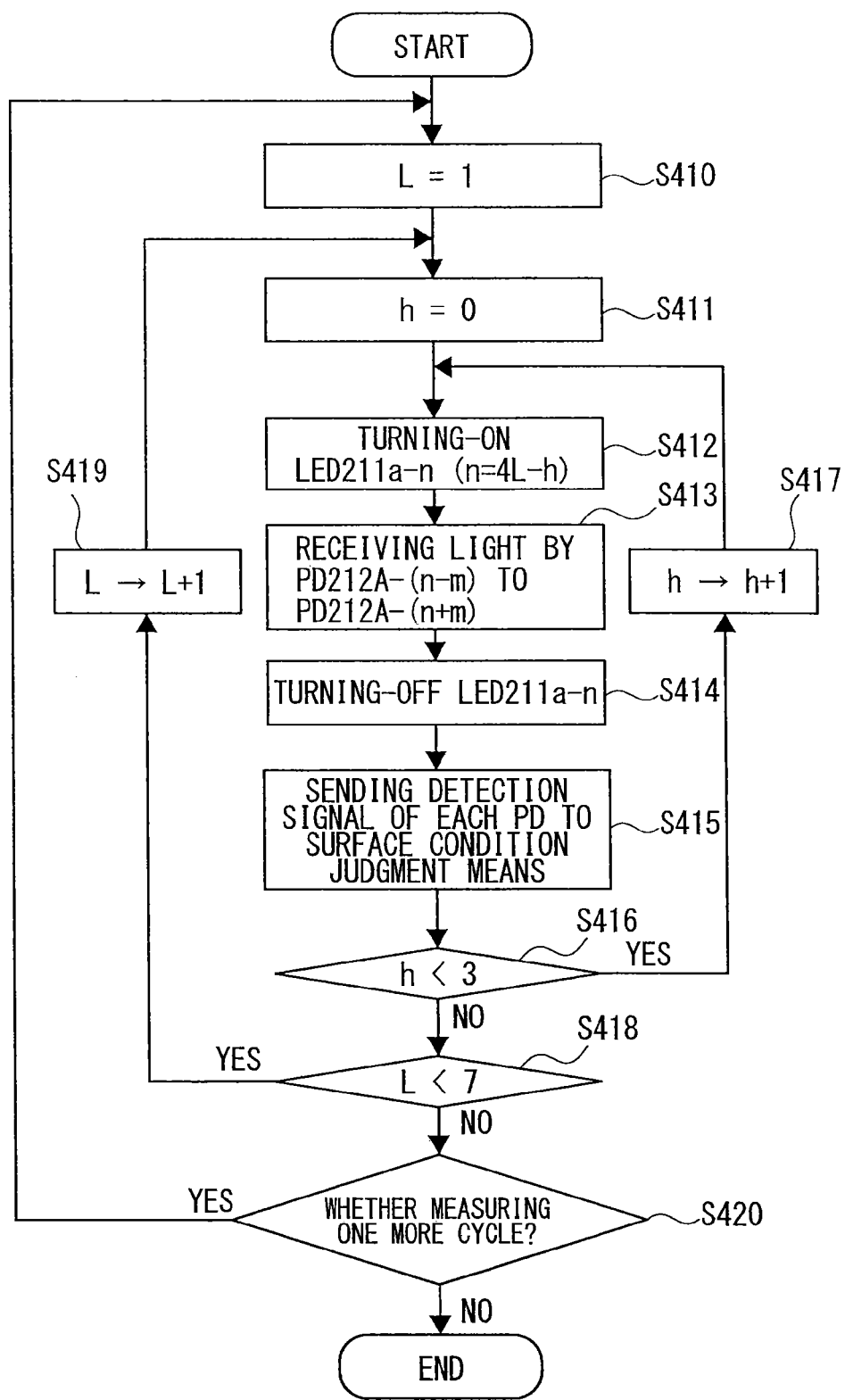
FIG. 32 is a flow chart showing operation of the reflection type optical sensor.

An example of the operation of the reflection type optical sensors is explained specifically using the reflection type optical sensors 200a regarding the fourteenth embodiment. FIG. 32 shows the operation flow, particularly process for each portion that constructs the reflection type optical sensors 200a, for the case that the optical spots SP are scanned in the positive orientation in x direction shown in FIG. 26. The same operation in each portion is sustained for the example for comparison and the following embodiments. In the fourteenth embodiment, sequential turning-on/off of the light such that each LED within unit is sequentially turned-on and turned-off from the right to the left in FIG. 26 with an order of unit 1, 2, . . . , 7, using an LED 211a-1 to an LED 211a-28.

As shown in FIG. 32, the operation starts with setting L=1 (wherein L is in the range of 1<=L<=7) as an initial value for the unit number (step S410). In the next step, a counter that controls the order of the sequential turning-on/off of the light is set as h=0 (wherein h is in the range of 1<=h<=3) (step S411). In the step S412, an LED 211a-n (n is a serial number of an LED 211a and an integer in the range of 1<=n<=28 and has the relation as n=4L−h) is turned on. For example, since in the first process where n=4, the LED 211a-4 in the most right in unit 1 turns on. In the next step, 2m pieces of a PD 212a-(n−m) to a PD 212a-(n+m) receive the reflected light that reflects on the surface of the fixing belt 461 (step S414). The details of receiving the reflected light are explained later. Then an LED 211a-n turns off (step S414) and each photodiode from the PD 212a-(n−m) to the PD 212a-(n+m) sends the detection signal to the surface condition judging device 300 (step S415).

In the step S416, where h<3 is satisfied or not, that is, whether the steps S412 to S415 have proceeded for all of the four pieces of the LED 211a or not is judged. If h<3 is satisfied, counting up of h (that is h=h+1) in step S417, the process comes back to the step S412. Then the processes in the steps s412 to S415 are recursively carried out. On the other hand, if n<N is not satisfied, the process goes to the step S418 since the processes of all LEDs 211a in the unit L have been completed. For example, it is judged that the processes of all of the LED 211a in the unit 1 are completed when the serial processes as turning-on of the light, turning-off of the light and sending the detected signal have been completed.

In the step S418, whether L<7 is satisfied or not, that is, where all processes of steps S411 to S417 have been carried out or not is judged. If L<7 is satisfied, counting up L as h=h+1 (step S419), process goes back to the step S411. If L<7 is not satisfied, the process goes to the step S420 since the processes for all units have been completed. In the present embodiment, when the process of the LED 211a-25 which locates in the left end in the seventh unit 7 is completed, the first scanning (the total processes are called one cycle hereinafter) is ended. At the last stage, whether the serial processes is repeated for another cycle is judged, if the judgment is "YES", the process goes back to the step S410 and repeats the steps from S411 to S419. If the judgment is "NO", whole processes are ended.

The operation of the PD 212a (such as step S413) in the time when the optical spots SP are scanned in the positive orientation in the x direction is explained as follows. Being synchronous to turning-on of the light of the n-th LED 211a-n, the PDs 212a receive the reflected light that reflected on the surface of the fixing belt 461. For the purpose of the simplicity, the plurality of PDs 212a is controlled to receive the reflected light. In other words, 2m pieces of the PDs 212a receive the reflected light.

The selection method of 2m pieces of the PDs 212a is explained. When the n-th LED 211a-n turns on the light, two of the PDs 212a such as one receives the maximum receiving light and the other the next maximum receiving light are extracted. For the arrangement of the PDs 212a regarding the fourteenth embodiment first, these two PDs 212a are adjacent each other. The center of these two PDs 212a in the x direction being X0=0, the PD 212 arrange at x=0+/−1.51×P'''a is extracted for the rest of 2m−2 pieces of PDs 212a. The variable X presents the relative distance from X0 in x direction, 1 an integer among 1, 2, . . . , m−1 and P'''a a pitch of an arrangement (see FIG. 26) in the primary scanning direction regarding the fourteenth embodiment. In a same manner, the distances of the arrangement gaps among a PD 212b, a PD 212c, a PD 212d in the primary scanning direction are set to be P'''b, P'''c and P'''d for the fifteenth to the seventeenth embodiments and P''' for the example for the comparison. The above constant 1.5 is to accept the deviation of the center-to-center distance within the two adjacent PD 212a.

The reflected light that is received by 2m pieces of the PDs 212a is photo-electrically converted into a signal and amplified into a detection signal. The detection signal amplified by each PD 212a is sent to the surface condition judging device 300 for every time when the reflected light is detected. In order to raise the precision of the detection, averaging process of the detection results is taken over a plurality of cycles. All of N pieces (N=28 for FIG. 26) of the LEDs 211a, from the left end to the right end as shown in FIG. 26, that turns on/off the light are not necessary to be used but an arbitral N''' (where 1<=N'''<=N is satisfied) pieces of the LEDs 211a among N pieces can be usable. In the selection of N''' pieces of the LEDs 211a, every adjacent ones or every two or three adjacent ones in accordance with the position, size and the dimension to the primary scanning direction on the fixing belt 461 may be selected. A combination of the LEDs 211a in the region where there is no scratch and a few of the LEDs 211a in the region where the scratches are actually made may be used. A single LED 211a locating in any one of the units is used.

(Operation of the Surface Condition Judging Device)

Figure 33:
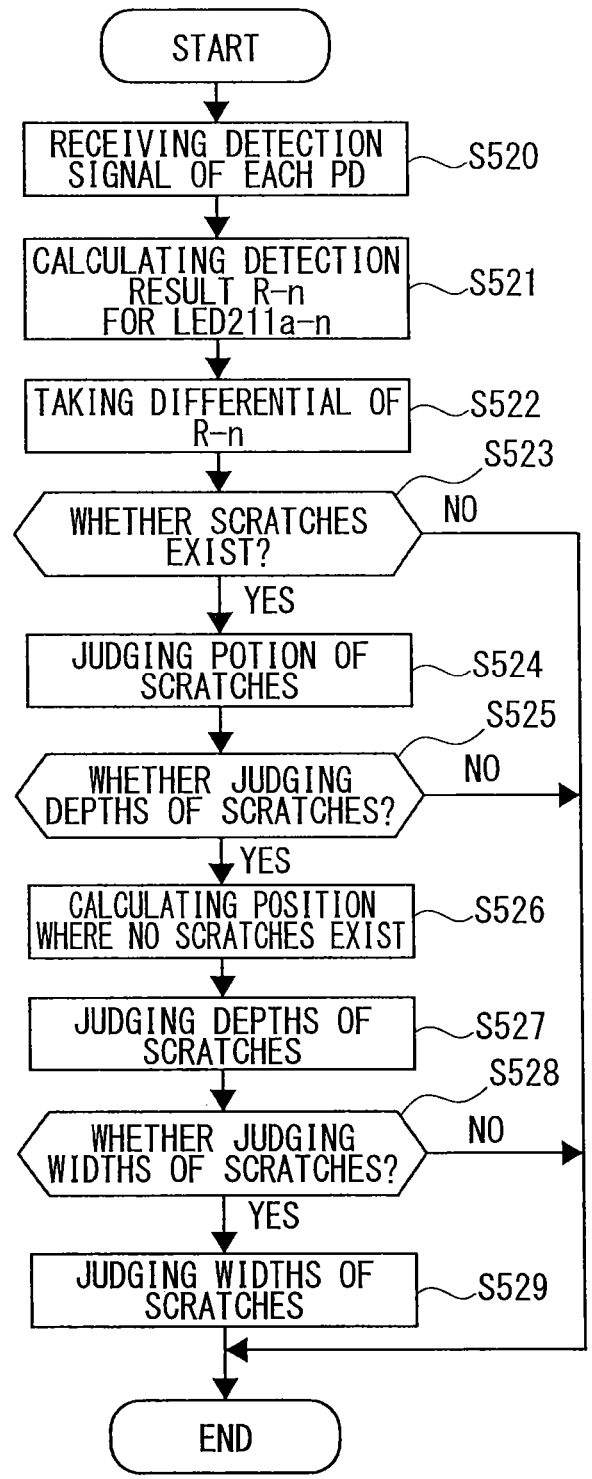
FIG. 33 is a flow chart showing operation of a surface condition judging device.

The operation of the surface condition judging device 300 is explained using the flow chart shown in FIG. 33. In the surface condition judging device 300, 2m+1 pieces of PDs 212a of the reflection type optical sensors 200a receive the light and send the detection signals (step S520). Taking summation of the detection signals, the detection result R−n corresponding to each LED 211a-n is calculated. In other words, each optical spot SP forming in the primary scanning direction, the light intensity of the reflected light can be obtained in correspondence to each position on the fixing belt in the primary scanning direction. (step S521).

The judgment method of the surface condition of the fixing belt 461 is explained. The nominal reflected light component decreases and the scattering light component increases in case that there are scratches on the surface of the fixing belt 461 in comparison to the case that there are no scratches on the surface of the fixing belt 461. In the reflection type optical sensors 200a, as shown in FIGS. 23A and 23B, regarding the fourteenth embodiment and the reflection type optical sensors 200', as shown in FIG. 32, regarding an example for comparison, the received light received by the PD 212a and the PD 212' decreases as much as the decrease of the nominal reflected light component. The received light received by the PD 212a and the PD 212' increases in accordance with the increase of the scattering light component. As the result, the intensity of the received light by the PD 212a and the PD 212' decreases when there are scratches in comparison to when there are no scratches. According to the variation of the received light, the condition of scratches, that is, the level of the scratches and the position of the scratches are calculated.

Figure 34A:
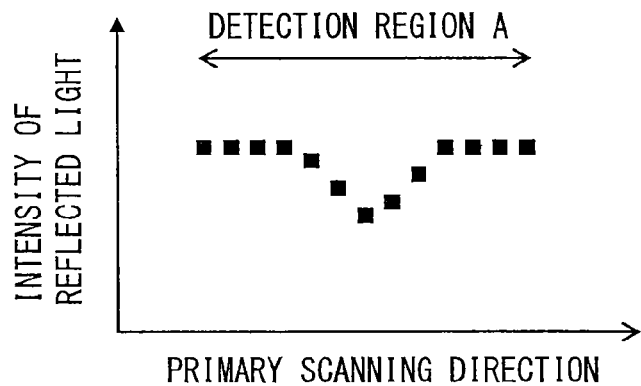
FIG. 34A is a diagram showing intensity of the reflected light detected at the detection region A regarding an example of comparison.
Figure 34B:
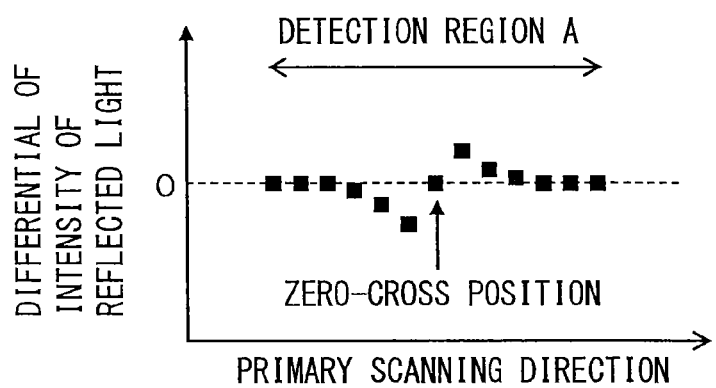
FIG. 34B is a diagram showing differential of intensity of the reflected light detected at the detection region A.

The judgment of the positions of the scratches is explained. Since the intensity of the reflected light is determined in accordance to the position on the surface of the fixing belt 461 in the primary scanning direction, it is possible to understand that there are scratches in the position on the surface where the intensity of the reflected light from the fixing belt 461 decreases in comparing the plurality of detections of the intensity of the reflected light in the primary scanning direction. The perspective of the intensity of the reflected light obtained by the reflection type optical sensors 200' as shown in the example for comparison is depicted in FIG. 34A. Taking the differential of the intensity of the reflected light with regard to the primary scanning direction (step S522), the positions of the scratches is judged by obtaining a zero-cross position of the differential of the intensity of the reflected light with regard to the primary scanning direction (step S523). FIG. 34B shows the perspective of the differential of the intensity of the reflected light and the determination of the zero-cross point. It may be noted that it can be judged that there are no scratches when the absolute values of the differential ones are less than pre-determined value since the intensity of the reflected light is remarkably low against the surface that has no scratches.

Figure 35A:
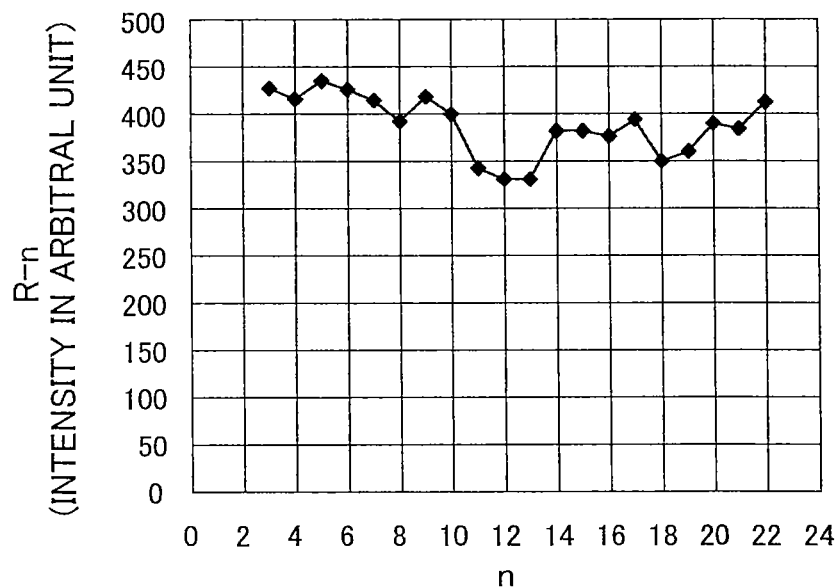
FIG. 35A is a diagram showing an intensity of the reflected light detected at the detection region A given as an example for comparison for the purpose of explaining a process to judge positions of scratches.
Figure 35B:
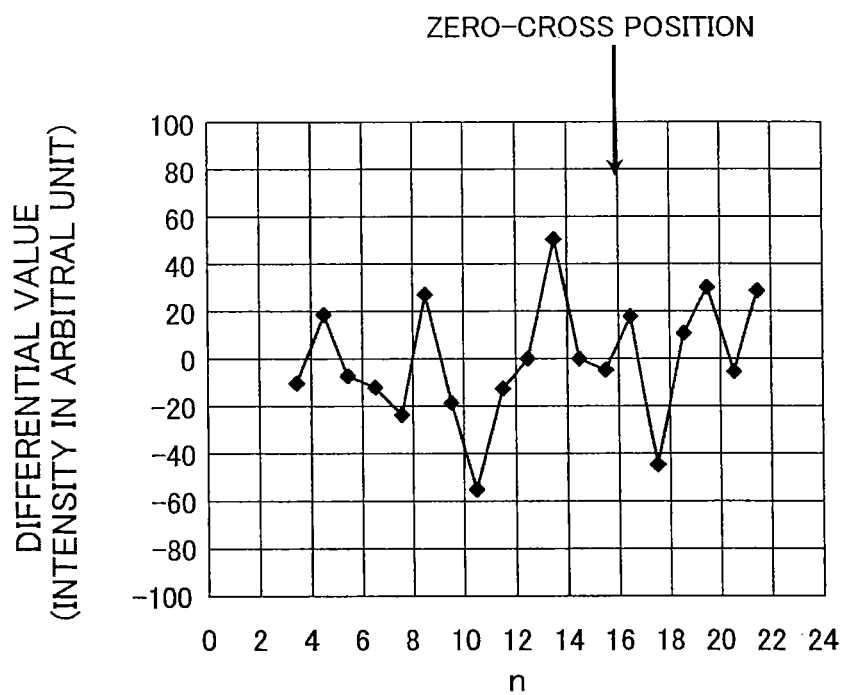
FIG. 35B is a diagram showing differential of an intensity of the reflected light detected at the detection region A given as an example for comparison for the purpose of explaining a process to judge positions of scratches.

In FIG. 35A, an example of the detection result R−n, using the reflection type optical sensor 200', being given as an example for comparison, that is specifically provided with N=24, n=3 to 22, m=2 and an arrangement pitch of LEDs 221' P=1 mm for the fixing belt 461 experienced with 400,000 pieces of recording papers passing, is shown. Since the light emitted to the surface of the fixing belt 461 with the optical spots SP in P'=1 mm pitch for the reflection type optical sensor 200' given as the example for comparison, the abscissa axis of the FIG. 35A corresponds to the light-illuminated positions (mm) of the optical spots. As shown in FIG. 35B, the result of the differential with regard to the primary scanning direction is provided where the gradient of two points R−n and R−(n+1) is taken. For the purpose of smoothening, a moving average is taken over R−(n−1), R−n and R−(n+1).

According to FIG. 35B, determining n=12.5 as the zero-cross position, it is possible that there is a scratch in the middle point of the light-illuminated position, which is 12.5 mm, of the optical spots corresponding to the LED 122'-12 and the LED 211'-13 (these processes are shown in steps S522 to S524).

Figure 34C:
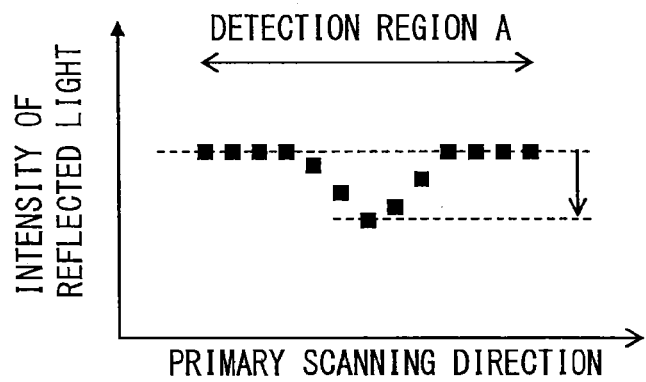
FIG. 34C is a diagram showing an amount of decrease of the intensity of the reflected light detected.

The judgment of the scratch level (the depths of the scratches) is done (the step S25) as shown in FIG. 34C. Since it is expected that the deeper (rougher) the scratches are, the further the intensity of the reflected light decreases, it is possible to detect the depths of the scratches by measuring the decrease of the intensity of the reflected light. FIG. 34C is a schematic that depicts the perspective of such decrease of the intensity of the reflected light. For the case shown in FIG. 34C, the depths of the scratches are simply obtained by measuring the minimum value for the detection result R−n, however it is expected that the light components due to the fixing status of the reflection type optical sensors 200' in the image generation apparatus 1 and tilt of fixing belt 461 etc. is biased to the detection result R−n. Therefore, the decrease of the intensity of the reflected light can be obtained in the following processes.

The position of scratches is judged as n=12.5 in the steps from S522 to S523 and by FIG. 35B. The position where there is no scratches is the position where the change of the detection result R−n is small, that is the position where the differential values are close to zeros. In other words, it is possible to determine the position where there are no scratches by using the results of the differential value with regard to the primary scanning direction. An example to determine decrease of the intensity of the reflected light is shown using the detection result R−n0 at the position n0 where there are scratches and the detection results R−n1 and R−n2 at least two position n1 and n2 where there are no scratches.

Figure 36A:
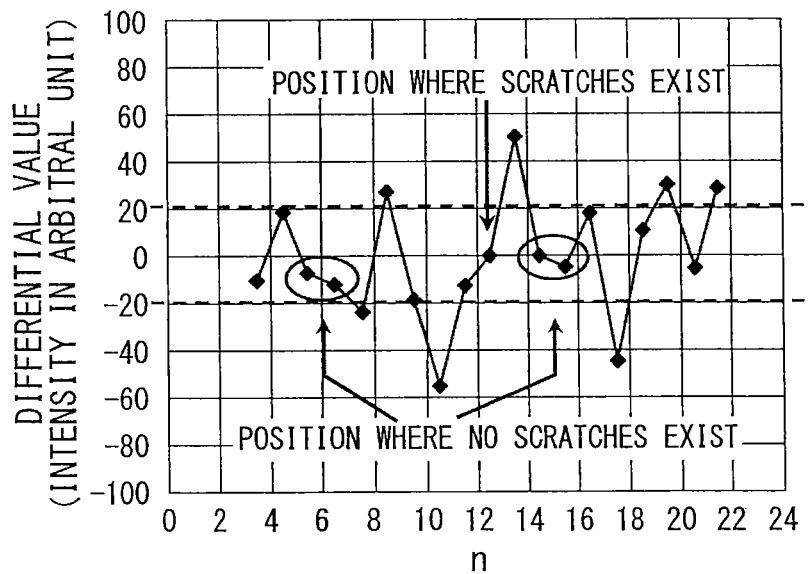
FIG. 36A is a diagram specifying positions where differential values are confined in a small range as +/−20 against locations of scratches as given an example for comparison.

In order to remove such component due to the gradient element superimposed in the detection result R−n, the distance between the detection result at the position where no scratches exist and the intensity of the reflected light at the position on an approximated straight line that goes through a plurality of detection results at the positions where scratches do not exist is used. The determination of the decrease of the intensity of the reflected light is actually explained using the results of FIGS. 35A and 35B. FIG. 36A shows the differential values against the positions of the scratches calculated by the results shown in the FIG. 35B wherein rather small differential values within +/−20 are assembled in a certain of n. It is possible to select the positions n−6 and 15 as those where there are no scratches (the step S526).

Therefore, it is possible to calculate the depth (roughness) of scratch using the each detection result R–n (step S527) after determining n0=12.5 as the position where there are scratches and n1=6 and n2=15 as the positions where there are no scratches. As shown in FIG. 36A, the broken line is a straight line crossing Rn–n1 and Rn–n2 and an arrow sign with a broken line shows the depths of the scratches. For this example, the depth of the scratch is 63.1 mm (it is necessary to confirm this unit). The decreasing rate of the intensity of the reflected light is 0.16 (that is, 16%). It can be seen that the depth of the scratches is superimposed to the gradient component shown in a broken line. The larger the level of the scratches becomes, the further the intensity of the reflected light decreases.

Figure 36B:
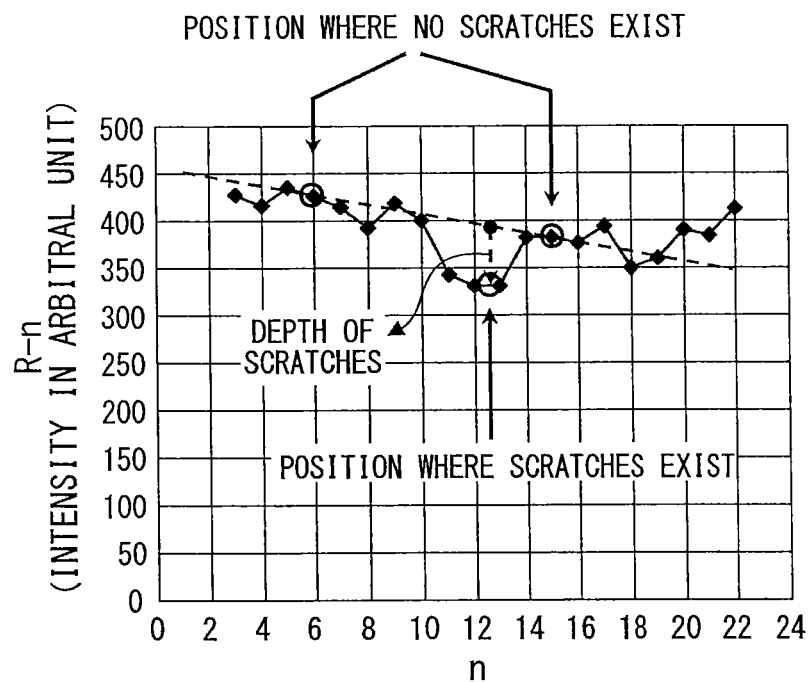
FIG. 36B is a diagram specifying depth of scratches.
Figure 37:
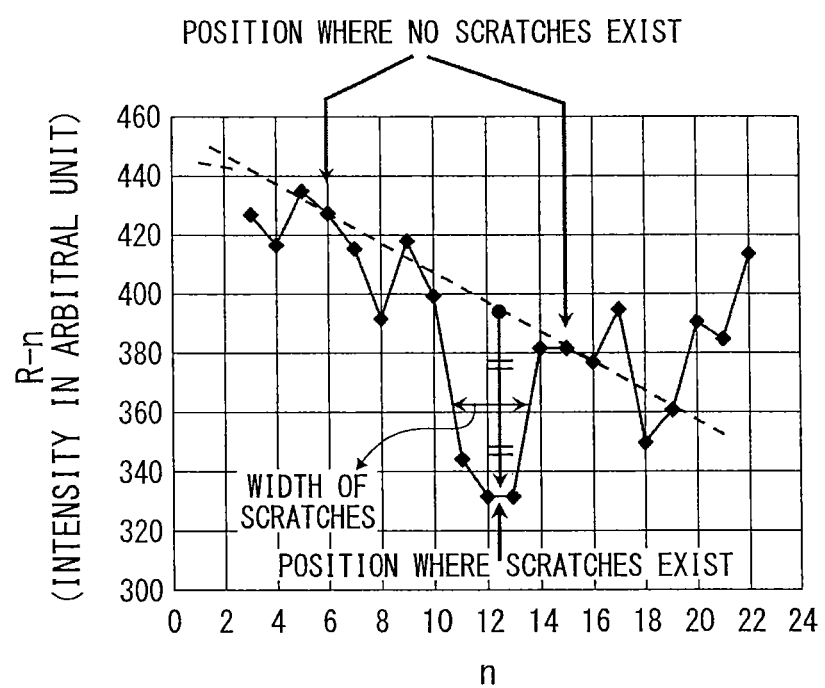
FIG. 37 is a diagram that has an extended ordinate of FIG. 36B.

In order to judge the surface condition of the fixing belt 461, another parameter to judge the width (or the size) of scratches is explained (the step S528). The center position of the scratches is judged in the steps from S522 to S523 and FIG. 35B. The positions at which the intensity of the reflected light that corresponds to the depth (or roughness) decrease to a predetermined intensity, for example, 50% thereof against the detection result R–n where there are scratches from the position thereof is calculate for the determination of the depths of scratches. FIG. 37 has an enlarged the axis of ordinate of FIG. 36B. It is possible to judge the half width of the scratch is 3 mm.

As explained above, all of the parameters such as depths of scratches (in the steps S525 to S527) and widths of scratches (the steps S528 and S529) may be assessed to be judged since it is possible to judge the details of the status of scratches by using all of these parameters. The judgment process can be quickly done by using only parameters that are necessarily required.

(Comparison of the Effects Between the Fourteenth Embodiment and the Example for Comparison)

The results of variation regarding PD output (or output for the light-receiving sensors) obtained in evaluation tests each using the reflection type optical sensors 200 of the fourteenth embodiment as shown in FIGS. 23 to 27 and the reflection type optical sensors 200' are presented in the diagrams shown in FIG. 38. Each diagram shows the result of the PD output variation for each case of detecting such output using two, four, six, eight and ten pieces of the PD 212a and the PD 212' with +/−50 micron meter deviation of lens array 220a and 220' in secondary scanning direction (Y named to be the deviation). Each diagram shows the results of PD output variation for several deviation of elevation angle A which is applied to the fixing belt 461 as well. The PD output is, as explained, the summation of the detection values of the plurality of PD 212a and the PD 212' are normalized as unity to the PD output wherein no deviation of the lens arrays 220a and 220' in the secondary scanning direction and no deviation of the elevation angle A (that is, Y=0 and A=0). The normalized values are named as medians hereinafter. For the PD output, the flare being removed light, there is scarcely the difference of light intensity between the reflection type optical sensors 200' regarding the example for comparison and the reflection type optical sensors 200a regarding the fourteenth embodiment.

As clearly understood by FIG. 38, the reflection type optical sensors 200a regarding the fourteenth embodiment has less fluctuation of the PD output caused by the deviation of the elevation angle A in comparison to the reflection type optical sensor 200' regarding the example of comparison. The PD output deviates with +/−10% against the median if the elevation angle A is within +/−1.5 degrees even when the deviation in the secondary scanning direction is +/−50 micron meter for the lens array 220a set to the light-receiving/emitting device.

Figure 27:
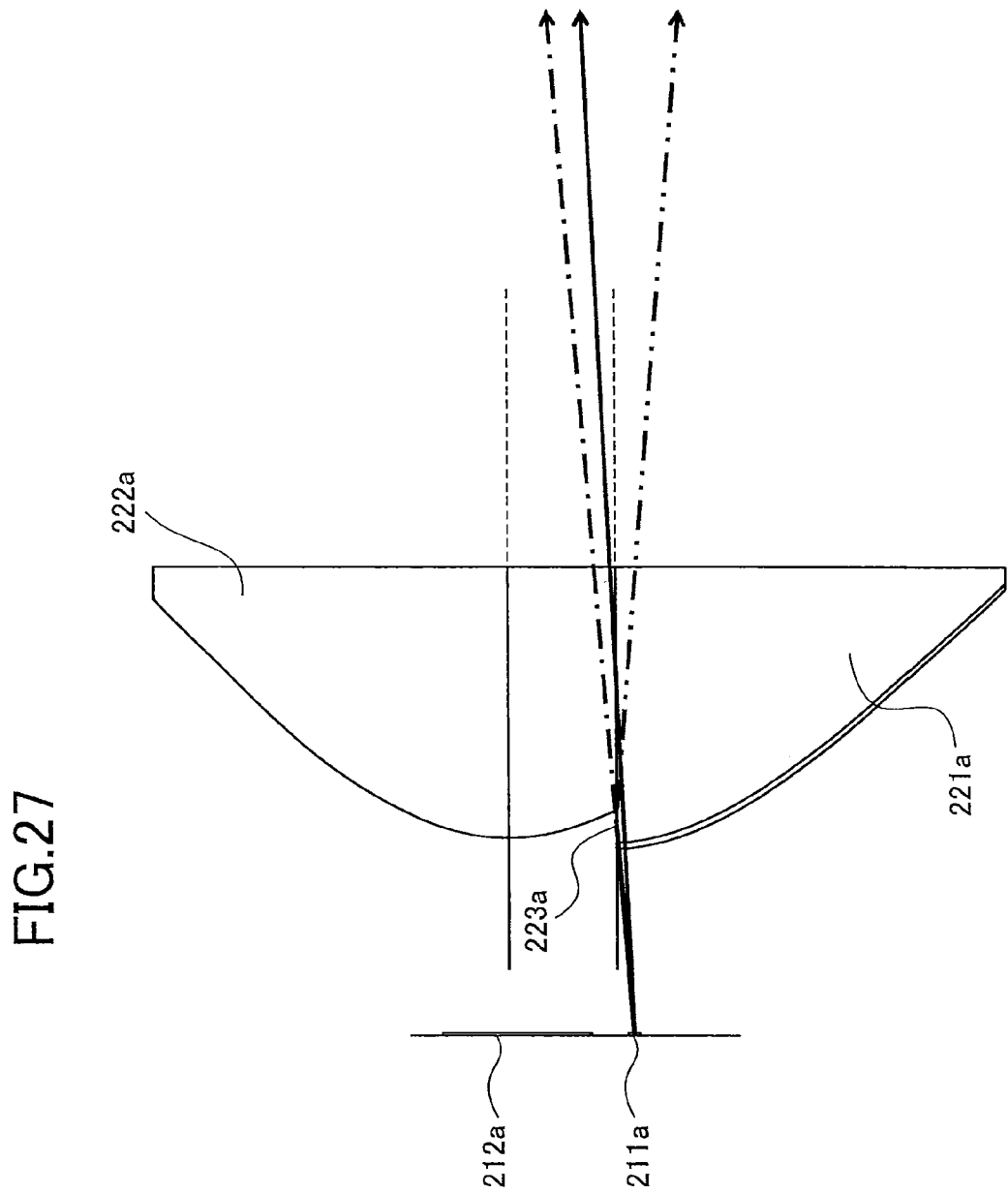
FIG. 27 is a schematic to explain a light reflection at the planner portion.

As shown in FIG. 27, the light is reflected on the planner portion 223a (as shown by an arrow with a two-dot chain line) which is set in the fourteenth embodiment. It is possible to reduce the light other than that necessary to detect the fixing belt 461 and suppress the degradation of the detection precision of the reflection type optical sensors 200a.

As explained above, the reflection type optical sensors 200a regarding the fourteenth embodiment has good optical properties. The printer 100 that uses the reflection type optical sensors 200a precisely detects the surface conditions of the fixing belt 461 since the surface condition judging device 300 receive the detection signal from the reflection type optical sensors 200a. The printer 100 can control to convey the blanks not to be placed on the region which has large scratches on the fixing belt 461 or control to heavily put toner on the portion which has scratches on the fix belt 461 so that the scratches are inconspicuous on the recording paper. Therefore the printer 100 can effectively prevent the degradation of the image quality. By alarming of buzzers or displaying warnings, users can get to know the time to exchange the fixing belt 461. Therefore, it is possible to effectively use the fixing belt 461 without exchanging the fixing belt 461 which still works well and does not damages to the image quality.

The Fifteenth Embodiment

Figure 40:
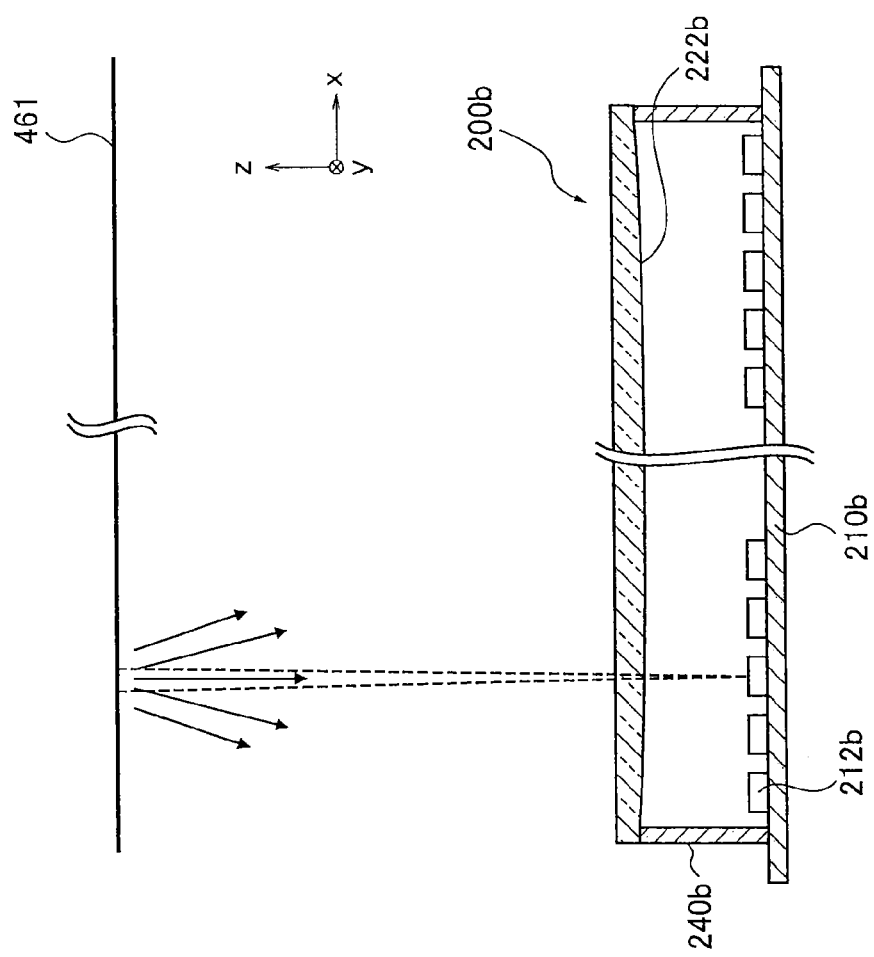
FIG. 40 is a schematic cross-sectional view of a PD and a light-receiving lens included in a reflection type optical sensor regarding fifteenth embodiment scanned in the direction of the secondary direction.
Figure 41:
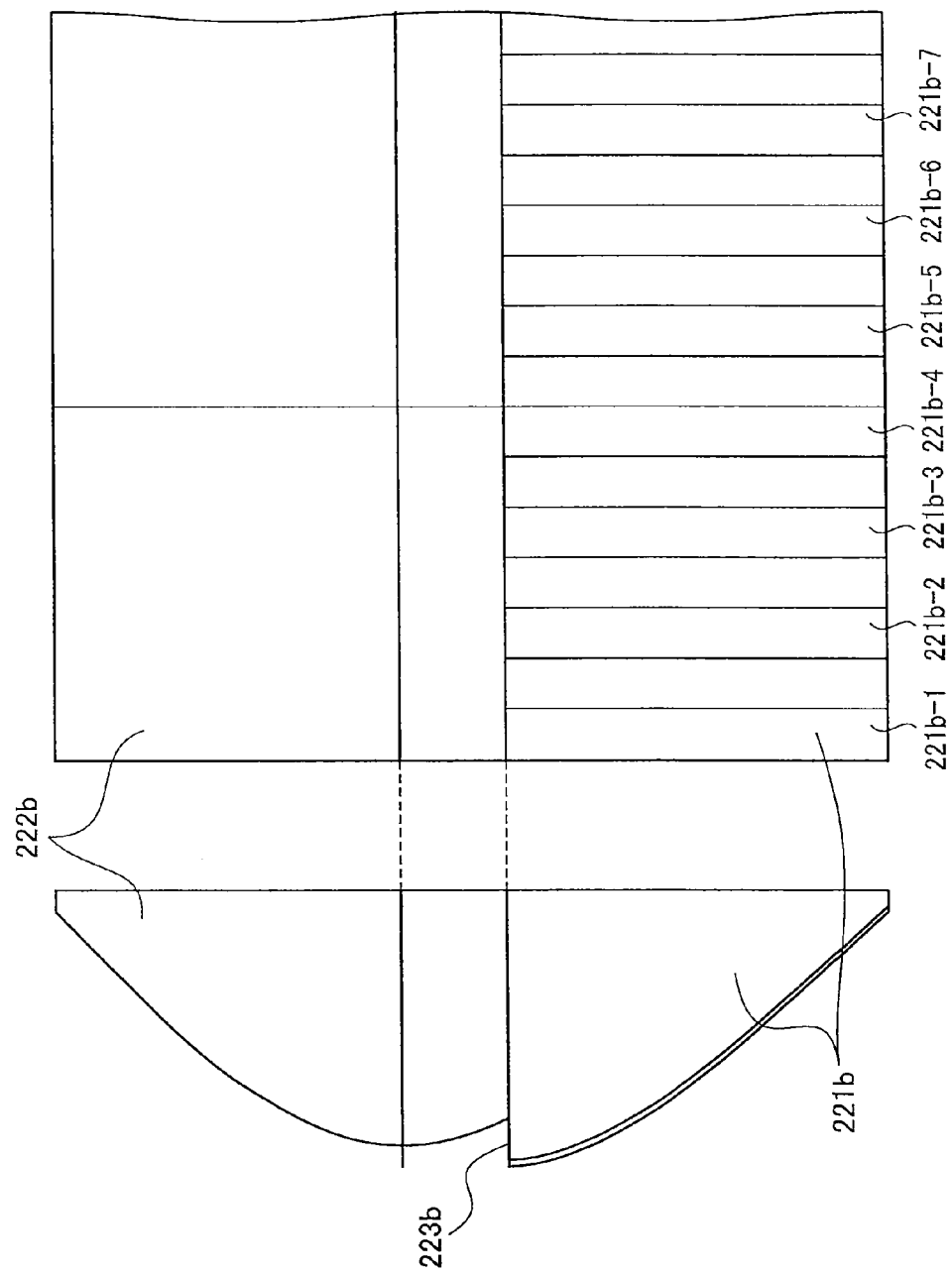
FIG. 41 is a schematic to explain details of a structure view of a lens array included in a reflection type optical sensor regarding the fifteenth embodiment.
Figure 42:
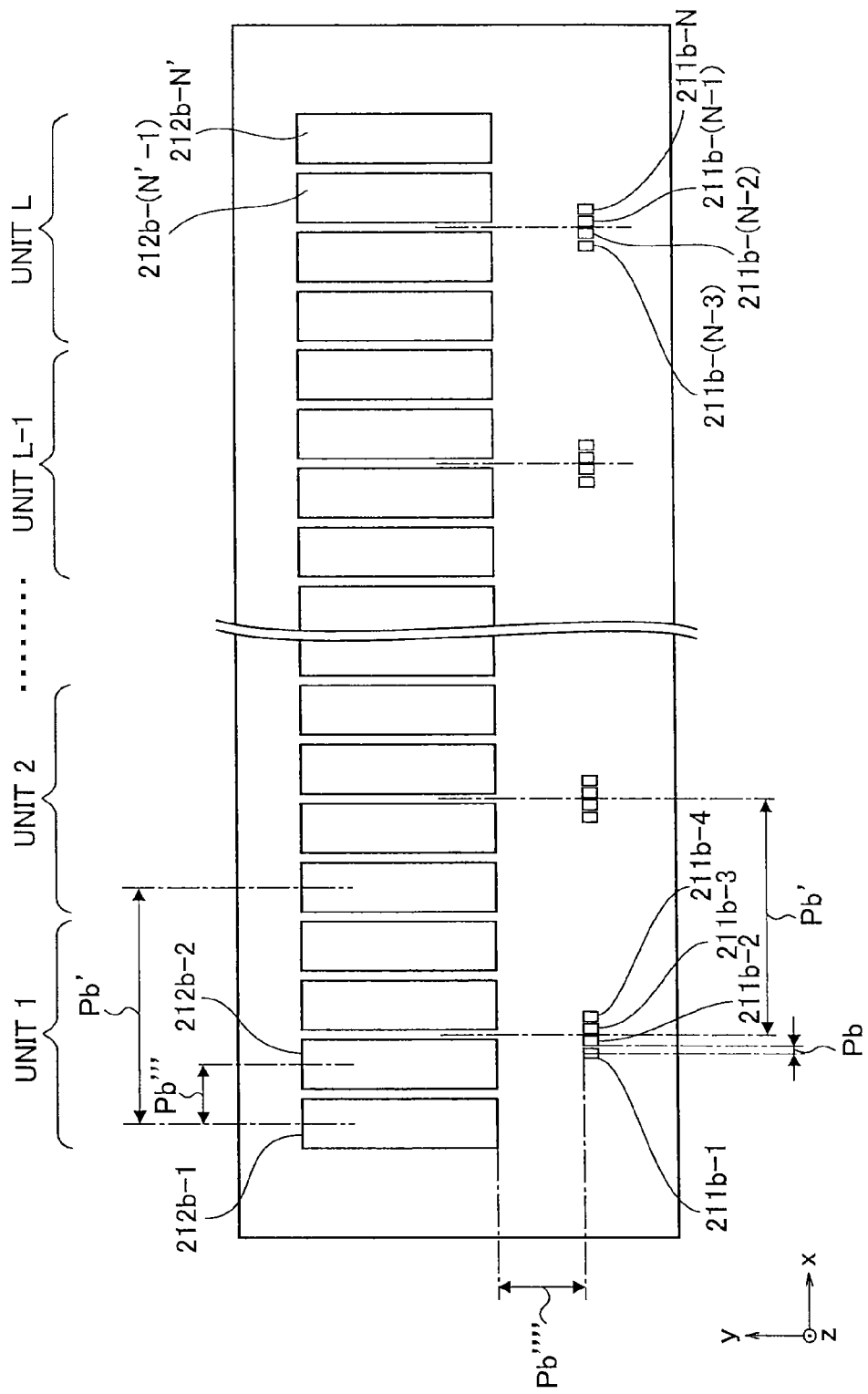
FIG. 42 is a schematic plan view of the board that supports an LED and a PD used in the fifteenth embodiment.

The structure of the reflection type optical sensors 200b regarding the fifteenth embodiment is explained using FIGS. 39A to 42. FIG. 39A is a schematic to explain a structure of the reflection type optical sensor 200b regarding the fifteenth embodiment, specifically a schematic cross-sectional view thereof along the direction of the primarily scanning direction (x direction). FIG. 39B is a schematic to explain a structure of the reflection type optical sensor 200b regarding the fifteenth embodiment, specifically a schematic cross-sectional view thereof along the direction of the secondarily scanning direction (y direction). FIG. 40 is a schematic cross-sectional view of the PD 212b and the light-receiving lens 222b included in the reflection type optical sensor 200b scanned along the direction of the secondary scanning direction (y direction). FIG. 41 is a schematic to explain details of a light-emitting lens 221b and a light-receiving lens 222b included in a reflection type optical sensor. FIG. 42 is a schematic plan view of a board that supports the LED 221b and the PD 212b in z direction.

As shown in FIGS. 39A to 42, the reflection type optical sensors 200b regarding the fifteenth embodiment comprises a light-emitting optical system including a light-emitting diode (LED) 211b working as a light-emitting member (that is a light emitter system) and light-emitting lenses 221b arranged to emit the light to generate the optical spots SP on the fixing belt 461, a light-receiving optical system including light-receiving lenses 222b arranged to guide the reflected light reflected at the fixing belt 461, a photo diode (PD) 212b working as a light-receiving member that receives the reflected light guided by the light-receiving lenses 222b, a board that supports an LED 211b and the PD 212b and a case 240b that holds a board 210b and a lens array 220b. The reflection type optical sensors 200b have a planner portion (or a step) 223b at the border between the light-emitting lens 221b and the light-receiving lens 222b.

The structure of the reflection type optical sensors 220b regarding the fifteenth embodiment is same as that of the reflection type optical sensors 220s regarding the fourteenth embodiment besides the light-receiving lenses 222b are arranged in the position that is farther from the light receiver system than the arrangement adopted in the fourteenth embodiment. The structure of the printer regarding the fifteenth embodiment is same as that of the printer 100 regarding the fourteenth embodiment besides the reflection type optical sensors 200b are used instead of reflection type optical sensors 200a. Therefore, detailed explanation will be omitted for the structure that is same as that of the fourteenth embodiment and be provided for the structure that is different from that of the fourteenth embodiment. The reflection type optical sensors 200b are different from the reflection type optical sensors 200a in the following due to being placed at the position such that the light-receiving lenses 222b are placed farther from the PD 212b than the structure adopted in the fourteenth embodiment.

The lens parameters (as curvature radius, lens diameter, lens thickness, center-to-center distance between the light emitter system and the light-receiving lens and the center-to-center distance between the light receiver system and the light-receiving lens) are different from those of the fourteenth embodiment.

The light-emitting lens 221b and the light-receiving lens 222b have a gap of 0.5 mm between their centers of the lens which is larger than the lenses regarding the fourteenth embodiment. The light-emitting lens 221b is placed closer to the light emitter system (or the LED 211b) than the light-receiving lens 222b is placed. As for the quantitative characteristics of the lens, in other words, the lens parameter is that the curvature radius and the conical constant of the light-emitting lens 221b in the primary scanning direction are 4.6 mm and 0, respectively and the curvature radius and the conical constant of the light-emitting lens 221b in the secondary scanning direction are 4.3 mm and −2.0, respectively. The lens diameters of the light-emitting lens 221b are 2.4 mm and 9.2 mm, respectively. The lens thickness of the light-emitting lens 221b is 6.6 mm.

The curvature radius and the conical constant of the light-receiving lens 222b in the primary scanning direction are 50 mm and −1.0, respectively. The curvature radius and the conical constant of the light-receiving lens 222b in the secondary scanning direction are 4.8 mm and −1.6, respectively. The lens thicknesses of the light-receiving lens 222b in the primary and secondary scanning directions are 17 mm and 5.6 mm, respectively.

The center-to-center distance between the light-emitting lens 221b and light-receiving lens 222b (distance between two optical axes) is 2.53 mm and the center-to-center distance between the light emitter system (or the LED 211b) in the optical axis direction and the light-emitting lens 221b is 10.37 mm and the center-to-center distance between the light receiver system (or the PD 212b) in the optical axis direction and light-receiving lens 222b is 11.37 mm.

FIG. 43 shows a diagram of PD output using the reflection type optical sensor 200a regarding the fourteenth embodiment and the reflection type optical sensor 200b regarding the fifteenth embodiment. Each diagram shows the result of the PD output variation for each case of detecting such output using two, four, six, eight and ten pieces of PDs 212a and PDs 212b with +/−50 micron meter deviation of lens array 220a and 220b in secondary scanning direction (that is, Y=+/−50 micron meters). Each diagram shows the results of the PD output variation for several deviation of elevation angle A which is applied to the fixing belt 461 as well. For the PD output, the flare being removed and there is scarcely the difference of light intensity in between the reflection type optical sensor 200a regarding the fourteenth embodiment and the reflection type optical sensor 200b regarding the fifteenth embodiment.

As clearly understood by FIG. 43, the reflection type optical sensors 200b regarding the fifteenth embodiment has less fluctuation of the PD output caused by the deviation of the elevation angle A in comparison to the reflection type optical sensor 200a regarding the fourteenth embodiment. The PD output deviates with +/−10% against the median if the elevation angle A is within +/−1.5 degrees even when the deviation in the secondary scanning direction is +/−50 micron meter for the lens array 220b set to the light-receiving/emitting device.

As explained, it is possible to reduce the PD output variation caused the deviation of elevation angle of the fixing belt 461 since the light-receiving lens 222b is placed farther from the PD 212b in comparison to the fourteenth embodiment.

The Sixteenth Embodiment

Figure 45:
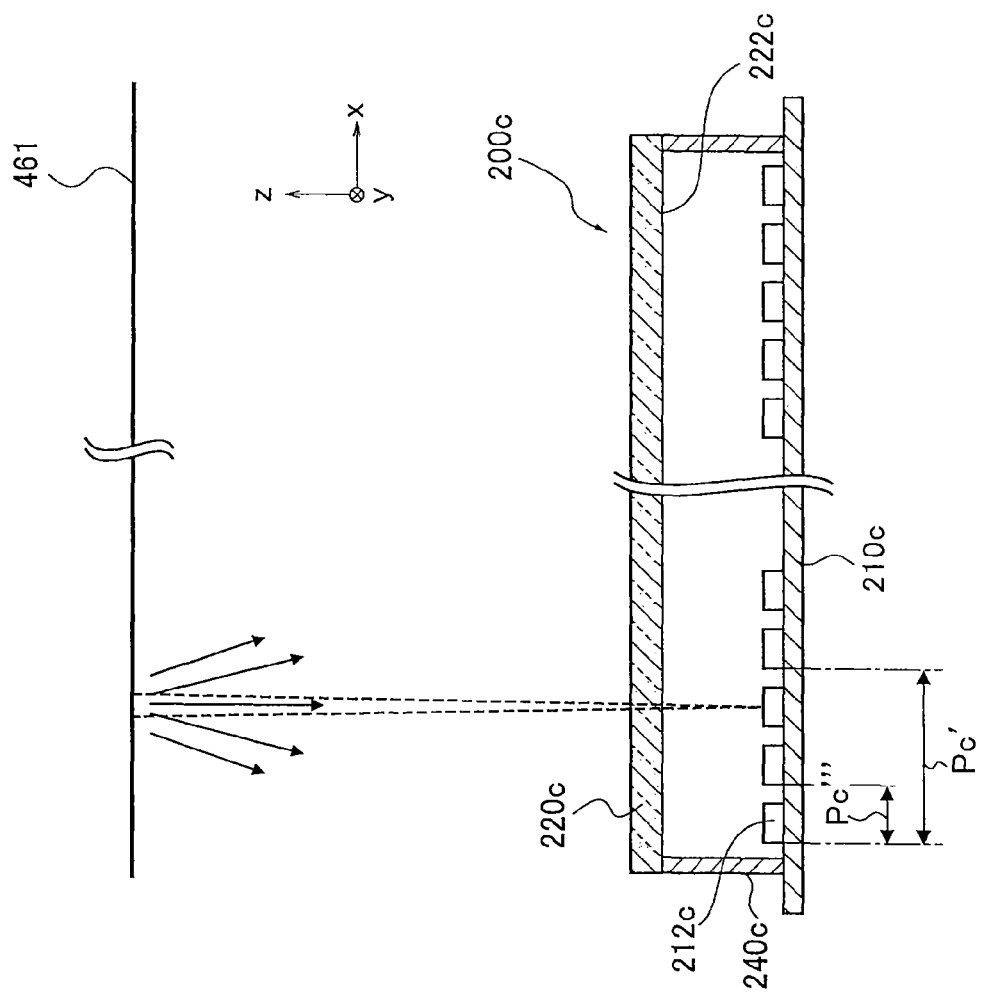
FIG. 45 is a schematic cross-sectional view of a PD and a light-receiving lens included in a reflection type optical sensor regarding the sixteenth embodiment.
Figure 46:
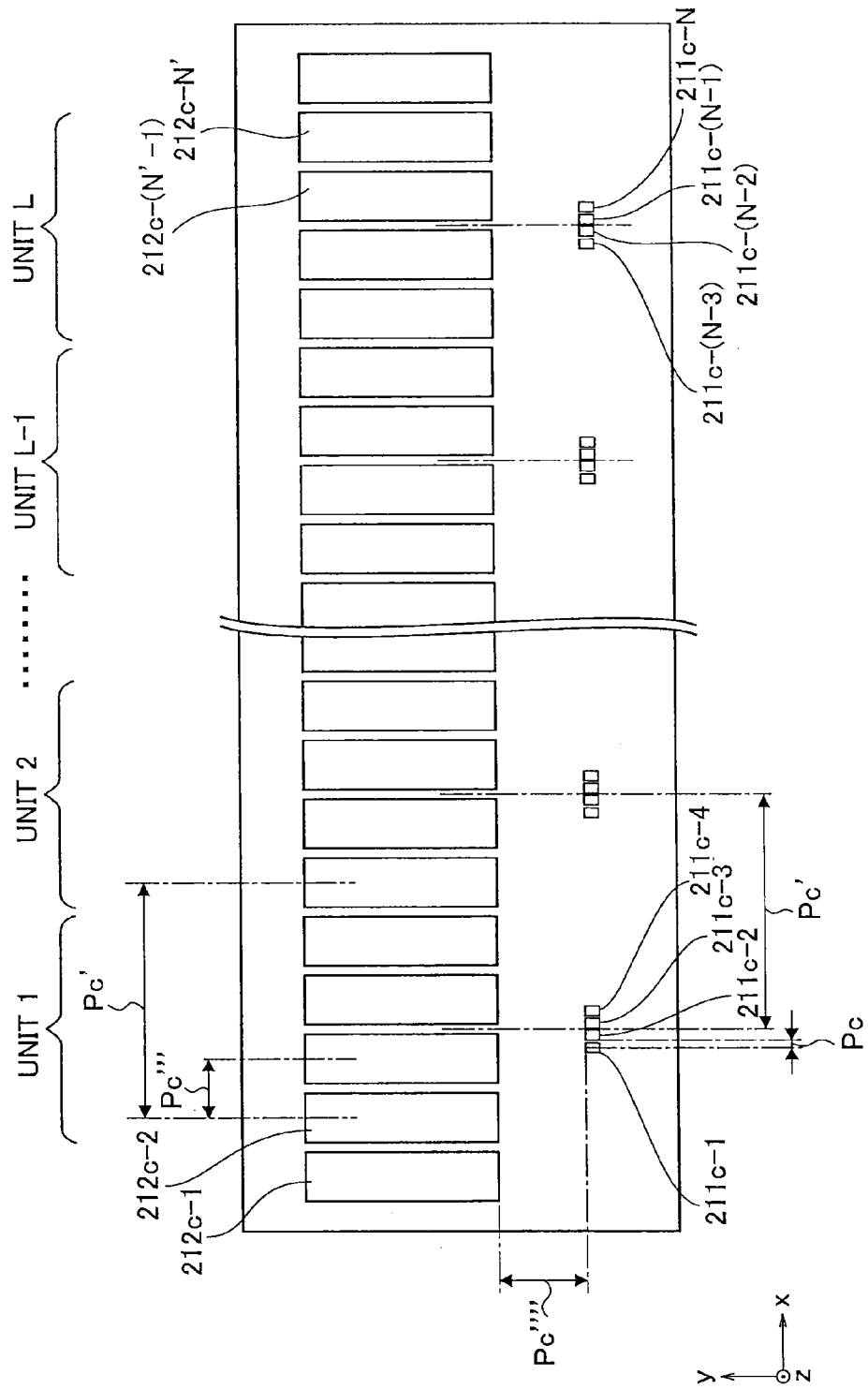
FIG. 46 is a schematic plan view of the board that supports an LED and a PD regarding the sixteenth embodiment.

The structure of the reflection type optical sensors 200c regarding the sixteenth embodiment is explained using FIGS. 44A to 46. FIG. 44A is a schematic to explain the structure of the reflection type optical sensor 200c regarding the sixteenth embodiment, specifically a schematic cross-sectional view thereof along the direction of the primary scanning direction (x direction). FIG. 44B is a schematic to explain a structure of the reflection type optical sensor 200c regarding the sixteenth embodiment, specifically a schematic cross-sectional view thereof along the direction of the secondarily scanning direction (y direction). FIG. 45 is a schematic cross-sectional view of a PD 212c and the light-receiving lens 222c included in the reflection type optical sensor 200c scanned along the direction of the secondary scanning direction (y direction). FIG. 42 is a schematic plan view of a board that supports an LED 221c and the PD 212c in z direction.

As shown in FIGS. 44A to 46, the reflection type optical sensors 200c regarding the sixteenth embodiment comprises a light-emitting optical system including a light-emitting diode (or LED) 211c working as a light-emitting member (that is a light emitter system) and light-emitting lenses 221c arranged to emit the light to generate the optical spots SP on the fixing belt 461, a light-receiving optical system including light-receiving lenses 222c arranged to guide the reflected light reflected at the fixing belt 461, a photo diode (or PD) 212c working as a light-receiving member that receives the reflected light guided by a light-receiving lenses 222c, a board 210c that supports the LED 211c and the PD 212c and a case 240c that holds a board 210c and a lens array 220c. The reflection type optical sensors 200c have a planner portion (or a step) 223c at the border between the light-emitting lens 221b and the light-receiving lens 222b.

The structure of the reflection type optical sensor 200c regarding the sixteenth embodiment is same as that of the reflection type optical sensor 200a regarding the fourteenth embodiment other than that the former sensor has a light-receiving lens 222c instead of an anamorphic lens used in the latter sensor. The printer regarding the sixteenth embodiment has the same structure as the printer 100 regarding the fourteenth embodiment besides that the former printer uses the reflection type optical sensor 200c. Therefore, detail explanation for the structures which are same structures as the fourteenth embodiment is omitted in the following discussion.

The lens parameters regarding sixteenth embodiment are concretely explained. As for the light-emitting lenses 221c, similar lenses to those regarding the fourteenth and the fifteenth embodiments are used and the lens parameters thereof are same. On the other hand, since the light-receiving lens 222c regarding the sixteenth is a cylindrical lens that converts the light into a line, the curvature radius and the conical constant both in the primary scanning direction are only different from those regarding the fourteenth and the fifteen embodiments so that the curvature radius and the conical constant of the light-receiving lens 222c are infinity and zero both in the primary scanning direction.

As shown in FIGS. 24 and 30, the reflection type optical sensors 200a and 200c regarding fourteenth and sixteenth embodiments are constructed such that the PD 212a and the PD 212c are arranged in the primary scanning direction, respectively. Therefore, it is necessary that the light incidental to a PD has to be converted in the secondary scanning direction considering the position and size of the PD in relation to the secondary scanning direction, however not in the primary scanning direction by effecting of the light-receiving lenses therein.

Therefore, as explained above, cylindrical lens that has no optical power against the primary scanning direction is adopted to the light-receiving lens 222c regarding sixteenth embodiment. For such structure, it is possible to suppress the variation of the intensity distribution of the receiving light by the PD against the difference of the LED 211c that turns on the light, therefore to precisely detect the surface condition of the fixing belt 461.

The seventeenth embodiment

Figure 47A:
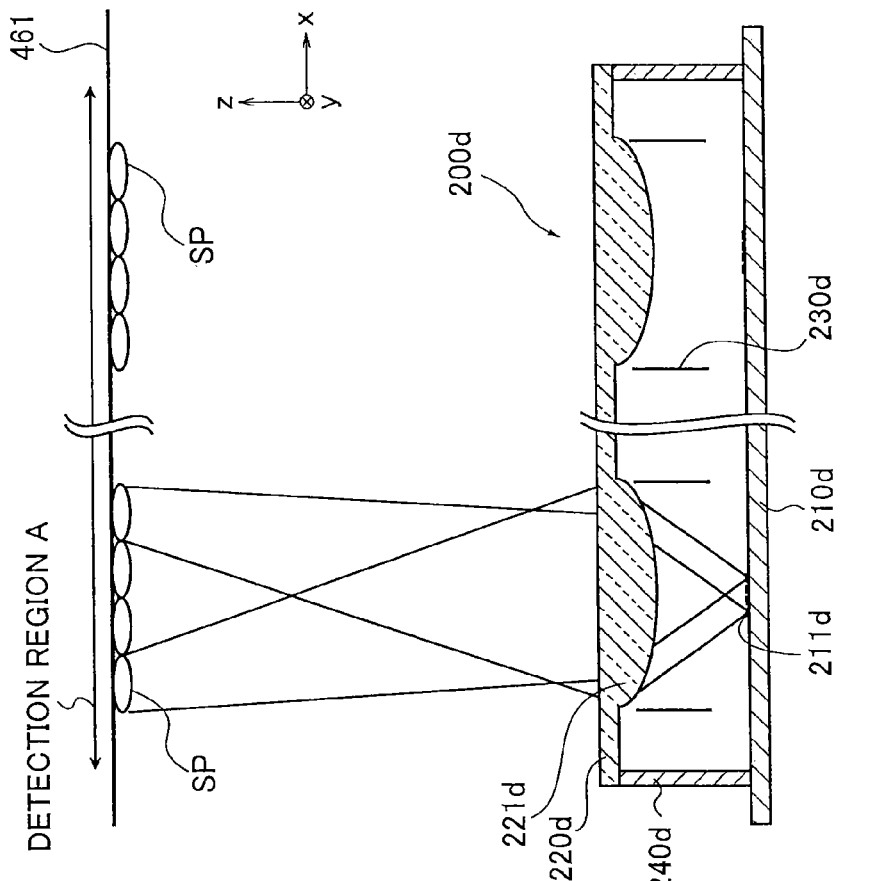
FIG. 47A is a schematic to explain a structure of the reflection type optical sensor regarding the seventeenth embodiment, specifically a schematic of the cross-sectional view of the reflection type optical sensor in the primarily scanning direction.
Figure 47B:
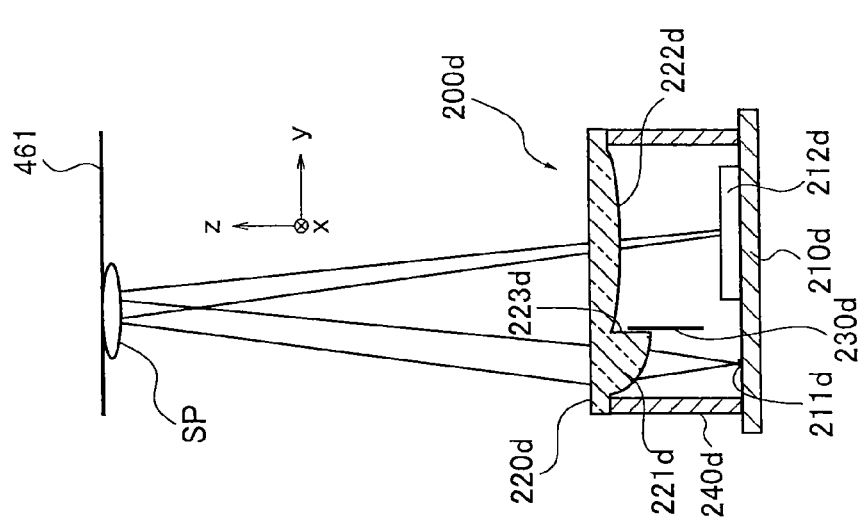
FIG. 47B is a schematic to explain a structure of the reflection type optical sensor regarding the seventeenth embodiment, specifically a schematic of the cross-sectional view of the reflection type optical sensor in the secondarily scanning direction.
Figure 48:
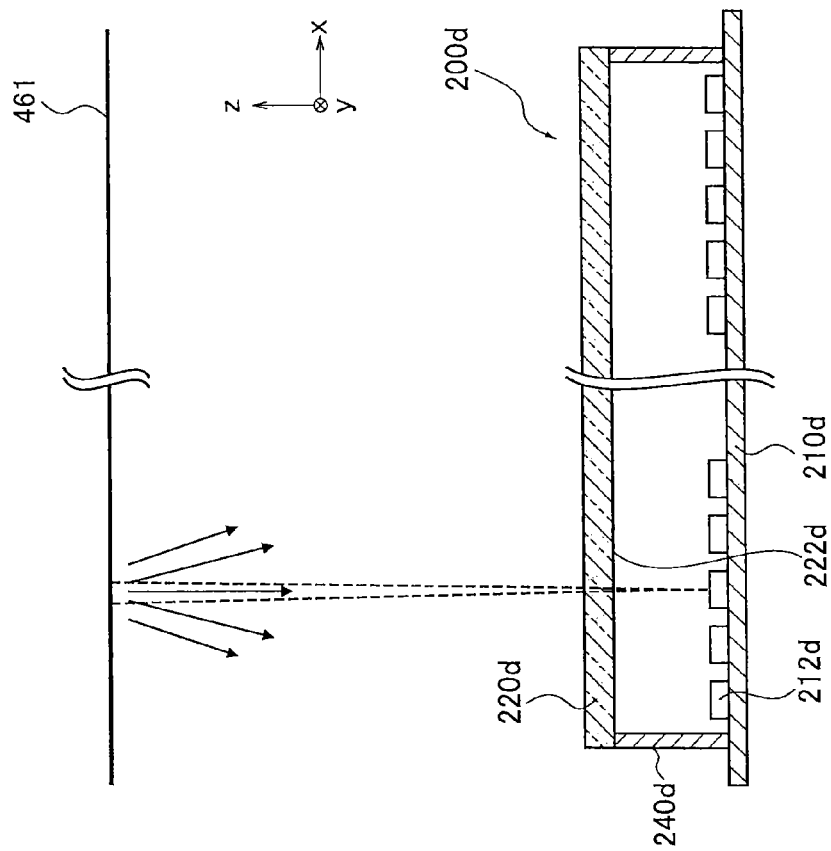
FIG. 48 is a schematic to explain a structure view of a lens array included in a reflection type optical sensor regarding the seventeenth embodiment.
Figure 49:
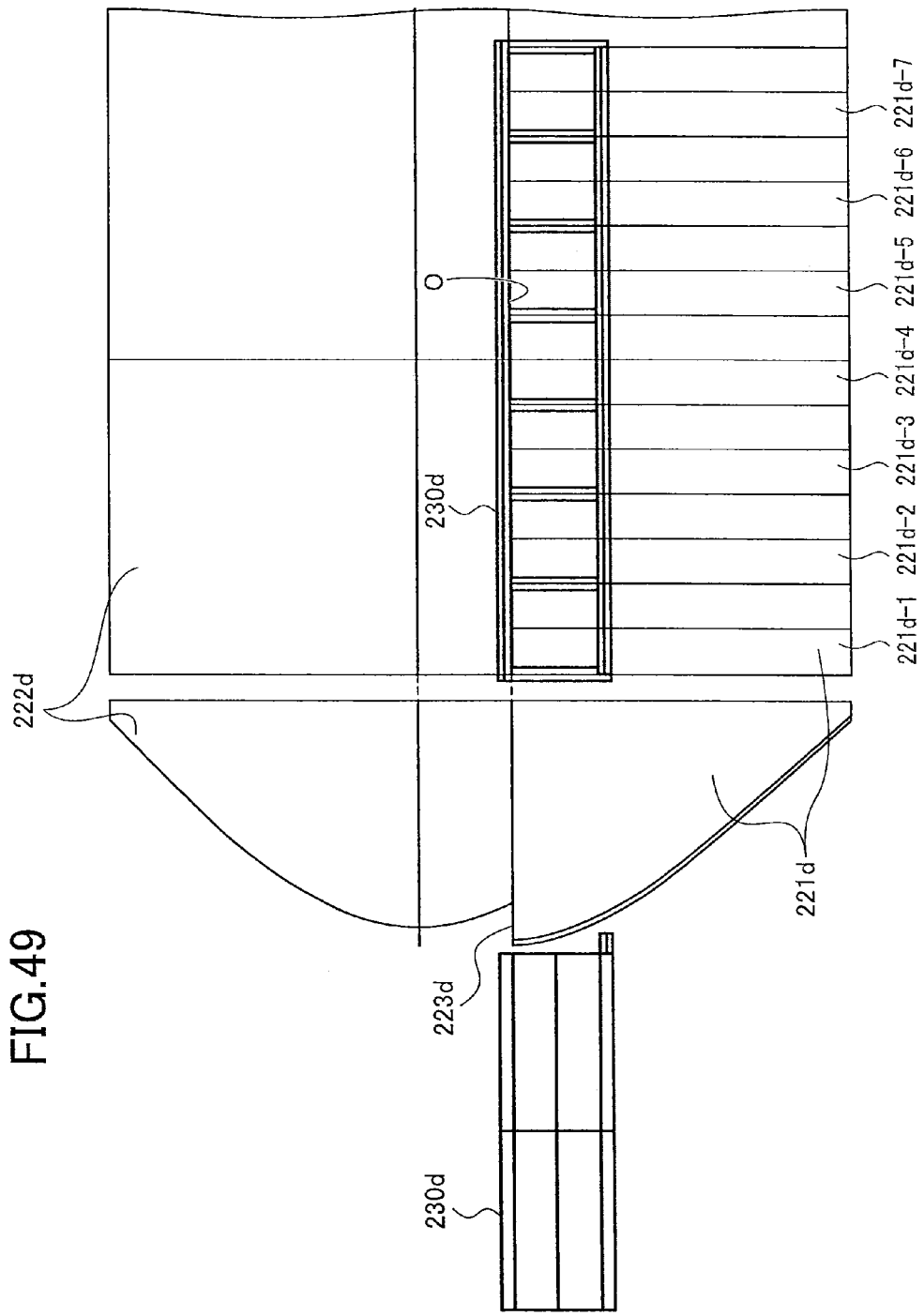
FIG. 49 is a schematic to explain details of a structure view of a lens array included in a reflection type optical sensor regarding the seventeenth embodiment.
Figure 50:
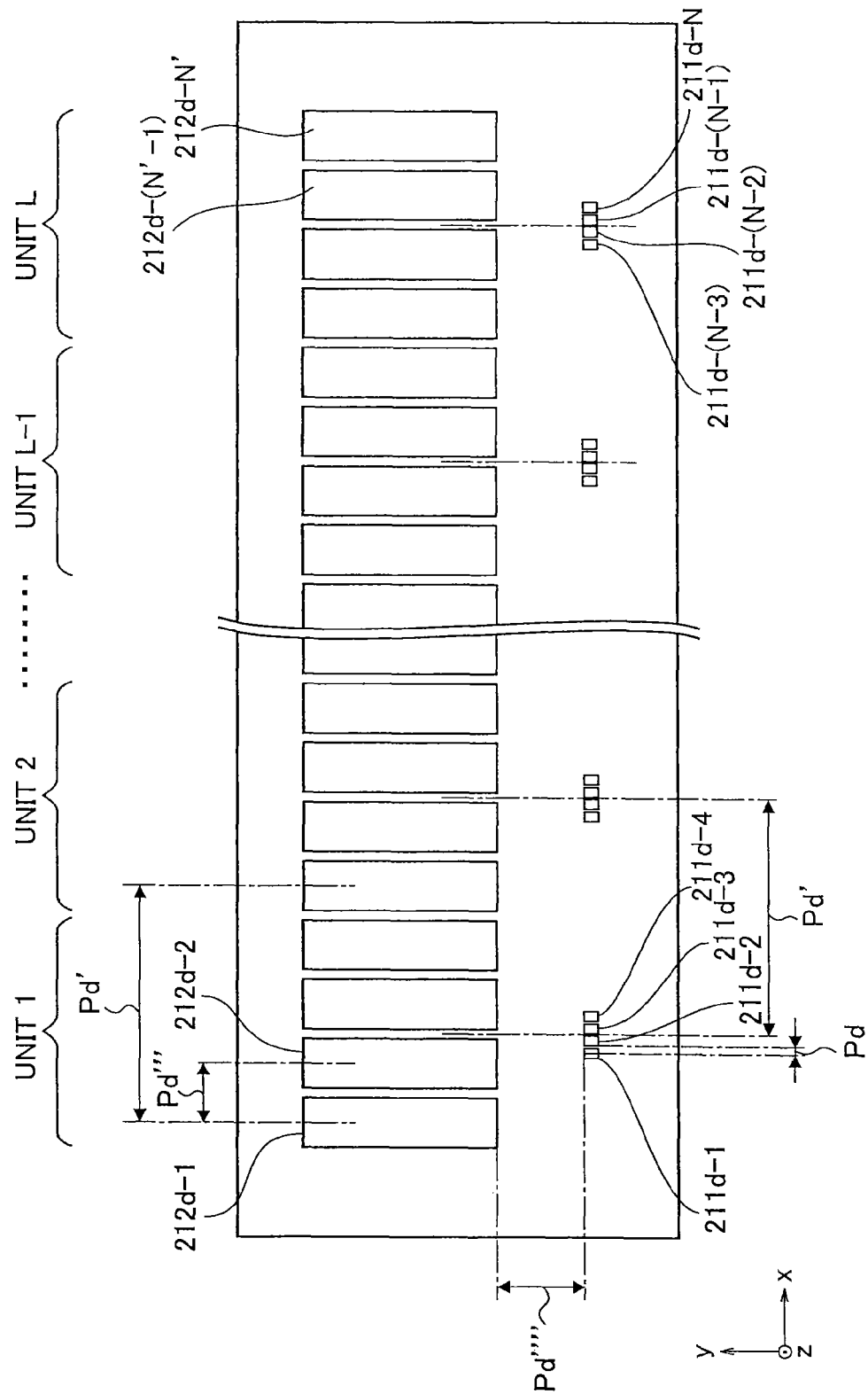
FIG. 50 is a schematic plan view of the board that supports an LED and a PD regarding the seventeenth embodiment.

The structure of a reflection type optical sensors 200d regarding the seventeenth embodiment is explained using FIGS. 47A to 50. FIG. 47A is a schematic to explain a structure of the reflection type optical sensor 200d regarding the seventeenth embodiment, specifically a schematic cross-sectional view thereof along the direction of the primary scanning direction (x direction). FIG. 47B is a schematic to explain a structure of the reflection type optical sensor 200d regarding the sixteenth embodiment, specifically a schematic cross-sectional view thereof along the direction of the secondarily scanning direction (y direction). FIG. 48 is a schematic cross-sectional view of a PD 212d and a light-receiving lens 222d included in the reflection type optical sensor 200d scanned along the direction of the secondary scanning direction (y direction). FIG. 49 is a schematic to show the details of a light-emitting lens 221d and a light-receiving lens 222d regarding the reflection type optical sensor 200d. FIG. 50 is a schematic plan view of a board that supports the LED 221c and the PD 212c in z direction.

As shown in FIGS. 47A to 50, the reflection type optical sensors 200d regarding the seventeenth embodiment comprises light-emitting diodes (LEDs) 211d working as a light-emitting member (that is a light emitter system), light-emitting lenses 221d arranged to emit the light to generate the optical spots SP on the fixing belt 461, light-receiving lenses 222d arranged to guide the reflected light reflected at the fixing belt 461, photo diodes (PDs) 212d working as a light-receiving member that receives the reflected light guided by the light-receiving lenses 222d, a board 210d that supports the LED 211b and the PD 212b, a lens array 220d formed into a single element that includes the light-emitting lens 221d and the light-receiving lens 222d, a case 240d that holds the board 210d and the lens array 220d, a light-blocking surrounding wall 230d, functioning to limit the incident light flux of the flare, that has an opening O therein. The reflection type optical sensors 200d have a planner portion (or a step) 223d at the border between the light-emitting lens 221d and the light-receiving lens 222d.

The structure of the reflection type optical sensor 200d regarding the seventeenth embodiment is same as that of the reflection type optical sensor 200c regarding the sixteenth embodiment other than that the light-blocking surrounding wall 230d functioning to limit the incident light flux of the flare wherein an opening O is formed. The printer regarding the seventeenth embodiment has the same structure as the printer 100 regarding the fourteenth embodiment besides that the former printer uses the reflection type optical sensor 200d. Therefore, detail explanation for the structures which are same structures as the fourteenth embodiment is omitted in the following discussion.

Due to the light-blocking surrounding wall 230d which surrounds the light-emitting lens 221d included in the reflection type optical sensor 200d regarding the seventeenth embodiment, it is possible to cut the flux of the light that passes the light-emitting lenses 221d other than the light-emitting lens 221d corresponding to an arbitral LED 211d that turns on the light or that of the flare that is the reflected light directly reflected on the surface of the light-emitting lenses 221d other than the light-emitting lens 221d corresponding to the arbitral LED 211d that turns on the light and the light-emitting lenses 221d other than the light-emitting lens 221d corresponding to the arbitral LED 211d that turns on the light so that such flux of the light does not directly enter into the PD 222d. As the results, it is possible to precisely detect the surface condition of the fixing belt 461.

The case 240d and the light-blocking surrounding wall 230d including the opening O can be formed into a single element by plastic molding.

For forming the opening O which is the opening end of the light-blocking surrounding wall 230d, a planner portion (or a step) 223d is used as the reference surface. Using such reference, it is possible that the positioning of the opening O as well as the light-blocking surrounding wall 230d can be precisely done and the degradation of the performance of the reflective sensor 200d is suppressed. Forming the opening O close to the planner portion (or a step) 223d, it is possible to remove the incidental light to the fixing belt 461 after passing through the light-receiving lens 222d and guide the incidental light that is guided onto the fixing belt 461 after passing the light-emitting lens 221d and the light-receiving lens 222d to be reflected at the planner portion (or a step) 223d to the position which is apart, in the secondary scanning direction, from the nominal position that the light reflected on the fixing belt 461 arrives at after passing through the light-receiving lens 222d. Therefore, the reflection type optical sensor 200d can maintain extremely precise detection.

By using the reflection type optical sensors 200b, 200c, 200d regarding the fifteenth to seventeenth embodiment, it is possible to sequentially turn-on/off the light. The functions of the reflection type optical sensors are not limited to theses ones explained above. The second example of different operation is explained using the fourteen to the seventeenth embodiment.

(The second example of the reflection type optical sensor)

The second examples of the reflection type optical sensors 200 (2001, 200b, 200c, 200d) regarding the fourteenth to the seventeenth embodiment are explained in the following paragraphs. It is possible to shorten the line cycle of optical scanning in the primary scanning direction. FIGS. 51A and 51B show the result of the PD output obtained in the second example.

For example, letting the quantity of the unit comprising four piece of LEDs and one light-emitting lens be nine and unit 1, unit 2, . . . , unit 9 are placed in x direction which is from the left to the right on FIG. 50. At the left end of unit 1 and the right end of unit 9, three pieces of PDs are additionally placed. Using such reflection type sensor 200, a plurality of LEDs included in unit 2 to unit 8 is turning-on at the time to detect the surface condition of the fixing belt 461. Four pieces of LEDs are placed in the positive direction of x direction. These pieces of LEDs as named LED1, LED2, LED3 and LED4 are arranged in this order. Therefore, LED3 in unit 2 is called LED2-3. As for PDs, those installed in nine units and additional 6 pieces that is 42 pieces in total are arranged in the order of PD_1, PD_2, ..., PD_42.

FIG. 51A shows the distribution of the PD output when LED2-3 turns on the light. The maximum intensity of the PD output is normalized as unity and the PD outputs are zeros for PD_1 to PD_4 and PD_15 to PD_18. Therefore, ten pieces of PDs (as PD_5 to PD_14) are used when LED2-3 (LED2-2) is turned on the light.

Two pieces, for example, of LEDs turn on the light, it is necessary that, one an arbitral LED turns on the light, ten pieces of PDs that are used for the sensor detection do not receive the reflected light generated by rest of one LED turning-on the light. Therefore, when a plurality of LEDs simultaneously turns on the light, those separately arranged in the primary scanning direction put may be used.

Figure 52A:
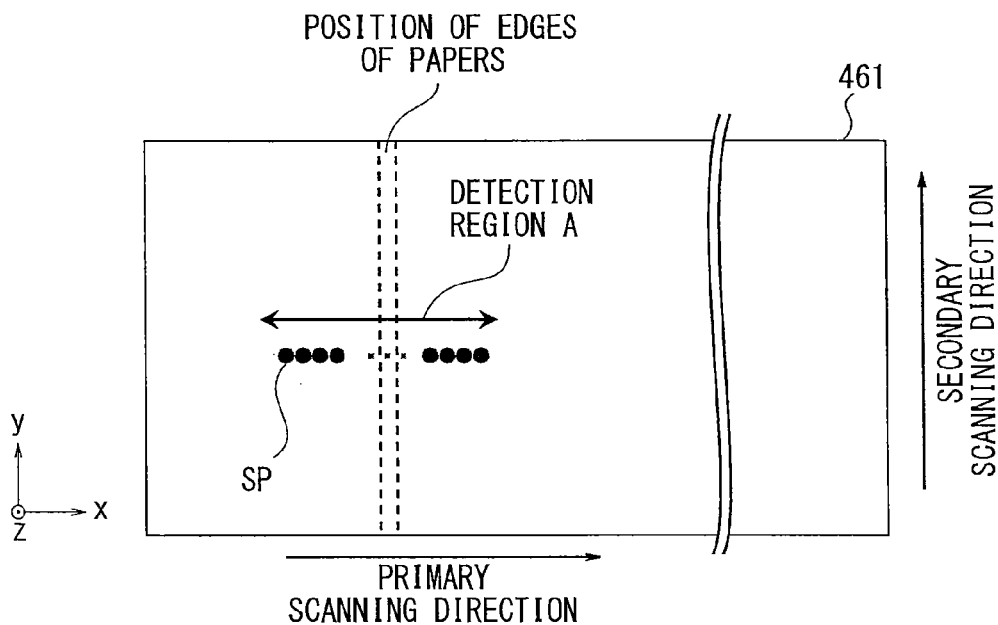
FIG. 52A is a schematic to explain a light-illuminated position of an optical spot when a reflection type optical sensor is aligned in parallel to the primary scanning direction.
Figure 52B:
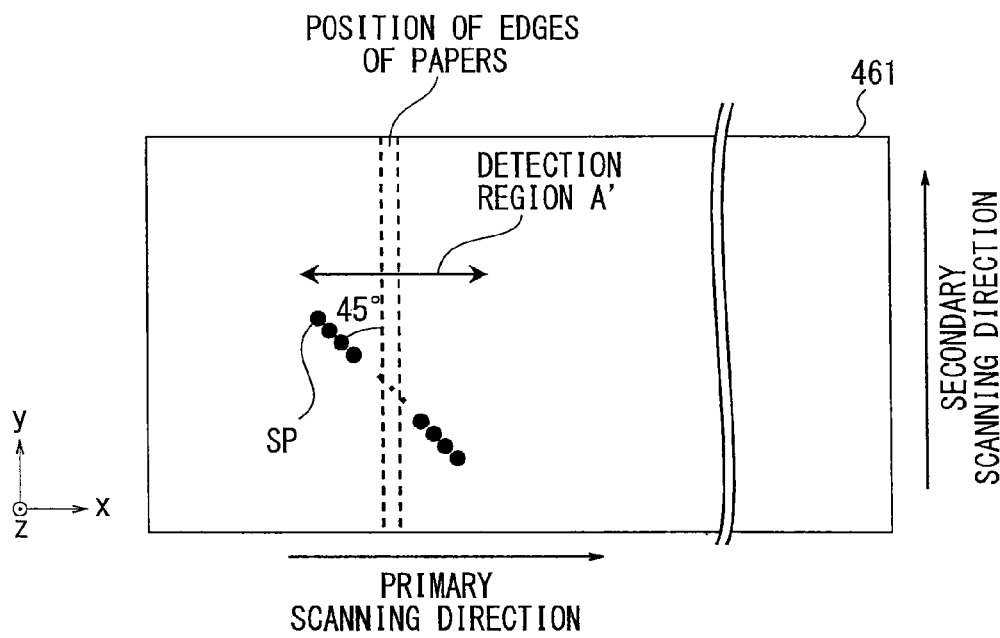
FIG. 52B is a schematic to explain a light-illuminated position of an optical spot when a reflection type optical sensor is aligned in 45 deg. angle against the primary scanning direction.

FIG. 52B shows the distribution of the PD output regarding a plurality of PDs when light-emitting member LED2-3, LED5-3 and LED8-3 (the third LED in unit 2, unit 5 and unit 8). Even when these three pieces of LEDs turn on the light, the output of an arbitral PD that receive the light thereof is equal to the output of an arbitral PD among a plurality of PDs that receive the reflected light caused by a single LED turns on the light.

For the example shown in FIG. 51B, it is possible to turn on the light regarding LED1 included in unit 2, unit 5 and unit 8, LED2 included in unit 2, unit 5 and unit 8, LED4 included in unit 2, unit 5 and unit 8 simultaneously turn on the light for each of unit 2, unit 5 or unit 8. It is also possible to turn on the light regarding LED1 included in unit 3 and unit 6, LED2 included in unit 3 and unit 6, LED4 included in unit 3 and unit 6 simultaneously turn on the light for each of unit 3 or unit 6 and LED1 included in unit 4 and unit 7, LED2 included in unit 4 and unit 7, LED3 included in unit 4 and unit 7 simultaneously turn on the light for each of unit 4 or unit 7.

Simultaneously turning on the light of a plurality of LEDs, it is possible to shorten the line cycle of the optical scanning in primary scanning direction. It is possible to improve the convey speed of the fixing belt 461 so that the time necessary for image generation can be shortened as well.

(Arrangement angle of the reflection type optical sensor)

The reflection type optical sensors 200 (as 200a, 200b, 200c and 200d) regarding to the fourteenth to seventeenth embodiments, are arranged in parallel to the primary scanning direction of the fixing belt 461. The present invention is not limited to such structure but can be provided in such arrangement that these reflection type optical sensors 200 are arranged in the direction different to the primary scanning direction. It is possible to make the pitch of the optical spot SP in the primary scanning direction small. FIG. 52A shows the light-illuminated positions of the optical spots SP for the case when the reflection type optical sensors are arranged in the primary scanning direction.

FIG. 52B shows the reflection type optical sensor is placed in such that the longitudinal axis thereof has 45 degrees angle against the primary scanning direction. In such arrangement, the detection region A' of the primary scanning direction and the pitch of the optical spot SP reduces by 1/square root of 2. Therefore, it is possible to improve the positional resolution of the detection results using the reflection type optical sensor by detecting narrow detection region A' with the same quantity of the optical spots SP, in comparison to the arrangement shown in FIG. 52A. The angle is not limited within 45 degrees, it may be appropriately selected in accordance with the widths etc. of the scratches. In the present embodiment, the reflection type optical sensor 200 is arranged with a declined angle to the primary scanning direction, but the arrangement is not limited with such declined angle. FIG. 52B shows another arrangement of the reflection type optical sensor regarding the present embodiment as the reflection type optical sensor 200 may be arranged in parallel to the primary scanning direction and the optical spots generated by the emitting light from the LED 211 has a row declined to the primary scanning direction. For such arrangement, the same effect such as improving the positional resolution.

As explained above, the inventions regarding the fourteenth to seventeenth embodiments that has the reflection type optical sensors 200a, 200b, 200c and 200d in the image generation apparatus (that is the printer 100) enables to detect the scratches in a real-time fashion and also detect the positions and widths of the scratches on the fixing belt, which has not been possible. Modifying the light-receiving sensors 200a, 200b, 200c and 200d and the optical system for the light-emitting member and sensors light-emitting member, it is possible to increase the intensity of the reflected light from the fixing belt 461 and improve the precision of detecting the scratches on the surface of the fixing belt 461.

Figure 53A:
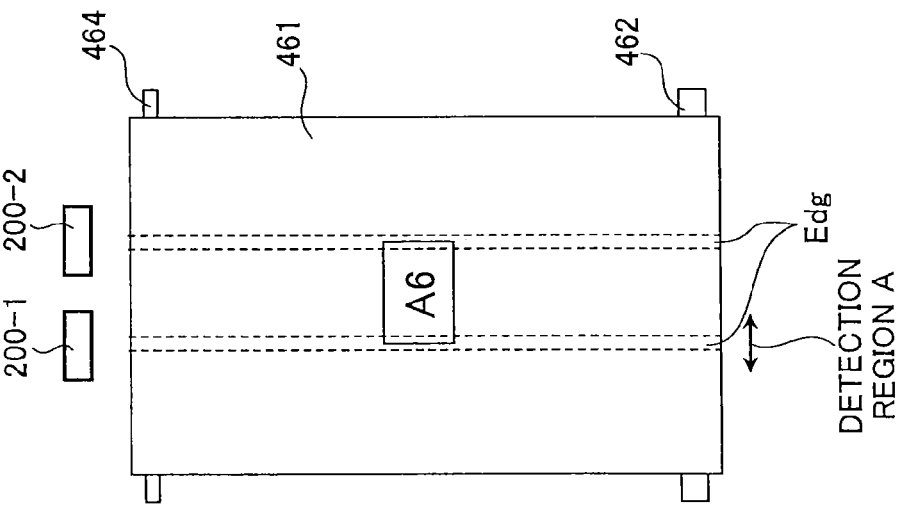
FIG. 53A is a schematic to show a layout plan of the reflection type optical sensor which is placed near the edge (or periphery) of small size paper, especially for use of A4 size paper.
Figure 53B:
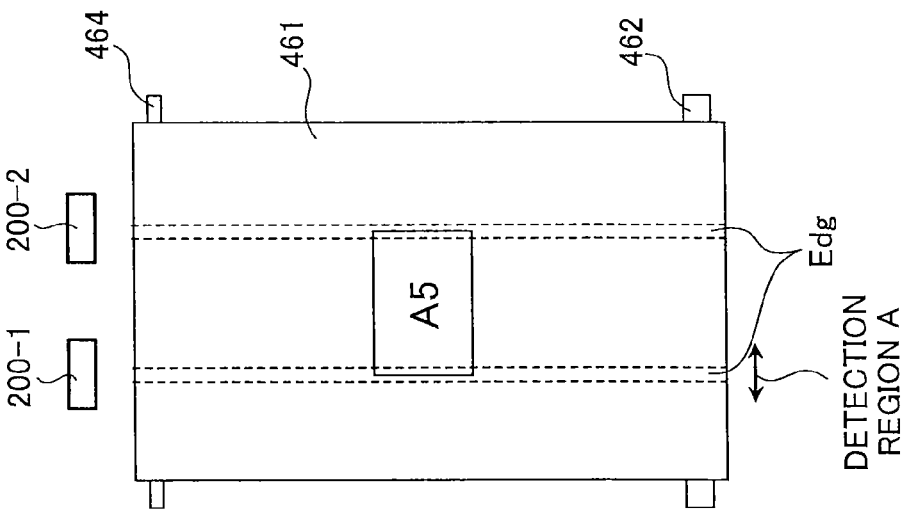
FIG. 53B is a schematic to show a layout plan of the reflection type optical sensor which is placed near the edge of small size paper, especially for use of A5 size paper.
Figure 53C:
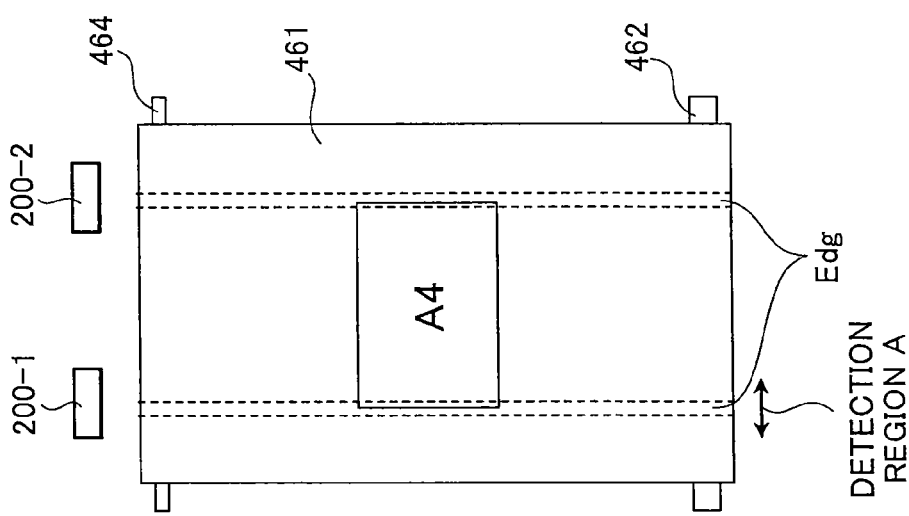
FIG. 53C is a schematic to show a layout plan of the reflection type optical sensor which is placed near the edge of small size paper, especially for use of A6 size paper.

For the reflection type optical sensors 200a, 200b, 200c and 200d regarding the fourteenth and the seventeenth embodiment, the preferable arrangement of the fixing belt 461 is explained. These reflection type optical sensors 200a, 200b, 200c and 200d are, as shown in FIGS. 53A to 53C, preferably placed near the passing region Edg through which the periphery portion in the width direction of the small size blanks passes. As shown in FIG. 53A, a passing region Edg that the periphery edge of width direction of the blanks passes through is included in the detection region A even when the width in the primary scanning in the detection region A is narrowed. Since the detection region A can be shortened, these embodiments imply the merit that the reflection type optical sensors 200 can be specifically shortened in the primary scanning direction. The widths of scratches are several hundred micron meters to several millimeters and positions of the scratches deviate within several millimeters at the center position. Therefore the detection region A is preferable set in 5 mm to 15 mm in the primary scanning direction.

For the image generation apparatus of the present invention, a plurality of various sizes of blanks such as A3, A4 and A5 sizes can be used. For many kinds of the image generation apparatus, the maximum size of the blanks is A3 in the longitudinal-laid direction. Therefore, the small size blanks imply the blanks excluding the A3 size one. If the image generation apparatus can print the A2 size blanks in longitudinal-laid direction, then the small size blanks implies those excluding A2 size.

There are two passing regions Edg where the periphery edge of small size blanks in the width direction pass through on the fixing belt 461, however as shown in FIGS. 53A, 53B and 53C, the reflection type optical sensors 200-1 and those 200-2 may be placed each at the both periphery ends of the blanks, so that two in total, in the primary scanning direction. By using such setting of the reflection type optical sensors, it is possible to surely detect the scratches. However, the present invention is not limited to such setting, it may be acceptable to set each of the reflection type optical sensors in only one side either of both sides of the blanks since the longitudinal streak scratches caused by the end surfaces of the blanks are generated on both periphery sides of the blanks and there are no remarkable differences between those scratches one in the one side and the others in the other side thereof. The use of a single reflection type optical sensor can reduce the facility cost.

Figure 54:
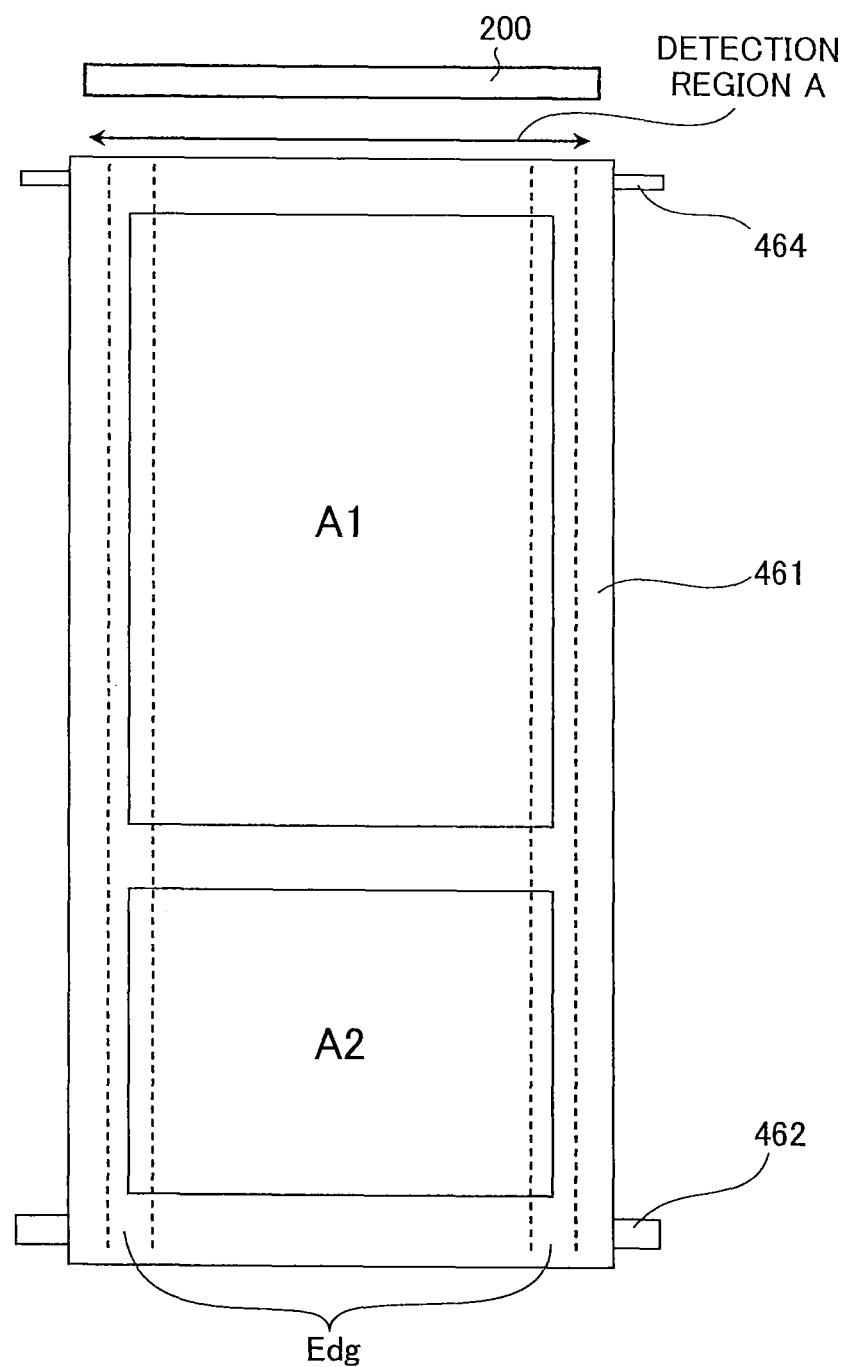
FIG. 54 is a schematic to show a view of an arrangement of the reflection type optical sensor, formed largely in the primary scanning direction, placed on the fixing belt.

The reflection type optical sensors 200 (including 200a, 200b, 200c, 200d) regarding each of the embodiments may be formed large in the primary scanning direction as shown in FIG. 54 so that the sizes thereof in such direction are substantively same as the width of the fixing belt 461 and the image generation apparatus or the present invention resultantly supports the printing various size of blanks. For example, the image generation apparatus of the present invention adopts the reflection type optical sensors 200 that is formed largely in the primary scanning direction in order to the passing region Edg of the periphery edges of blanks in the width direction can be emitted by the reflection type optical sensor 200 then the image generation apparatus of the present invention can detect the surface condition of the fixing belt 461 as well as support the printing of the various size of the blanks. In the operation of the reflection type optical sensor 200, all LEDs can be turned on or part thereof can be turned on in response to the sizes of the blanks. In order to allow the change of the sizes of the blanks, for example, the LEDs that are near to the region through which the edges of the blanks pass are only used based on the information detected by the printer body regarding the blanks that are conveyed on the fixing belt. For this design of the printer body, it is possible to save energy by confining the necessary LEDs to turn on the light so that it is possible to precisely the surface condition of the fixing belt such as the scratches on the fixing belt as well as energy efficiency can be improved.

In the selection of the fixing members (moving bodies), any of the technologies or materials in the public domain may be adopted however the fixing belts which have no peripheries are preferable to be used. The surface of the fixing belt is easily scratched since the surface is coated with a material such as PFA etc. Inner stress, seam, or inhomogeneity of the surface condition in the secondary scanning direction of the fixing belt causes the difference of the reflection angle against the flat surface of the fixing belt at the different place thereof to detect. However, the image generation apparatus having the reflection type optical sensors regarding the present invention can precisely detect the surface condition even if the image generation apparatus uses such fixing belt that the detection characteristics of surface condition in the secondary direction vary on the position of the fixing belt.

The image generation apparatus having the reflection type optical sensors regarding fourteenth to seventeenth embodiments have been explained however these are the parts of the embodiments that implement the present invention. The present invention is not limited in these embodiments. The reflection type optical sensors that can emit the light to form the plurality of optical spots in the primary scanning direction on the surface of the fixing belt can solve the problems that have been unsolved before the present invention is made.

The reflection type optical sensors regarding each embodiment include a plurality of LEDs and PDs of which each LED and each PD are set opposing in a fashion of one-to-one correspondence. A single LED of which emitted light is deflected and form the optical spots on the fixing belt wherein the reflected light from such the optical spots are detected by a single or a plurality of PDs can be preferably used for the present invention. The structure that the reflection type optical sensors having an LED and a PD is driven by a drive device in the primary scanning direction of the fixing belt. Further preferably used for the present invention.

According to the above discussion, the present invention has the following effects.

It is possible to precisely detect the surface condition at each position in the with direction of the moving body by comparing the received light received by at least row light-receiving members, wherein the received light is reflected on the surface of the moving body each emitted from at least two light-emitting members. For example, it is possible to detect existence of actual scratches on the moving body and the precise status of the scratches such as the positions, depths and widths of the scratches.

According to the present invention, it is possible to provide the reflection type optical sensors having such good optical characteristics to robustly detect the surface condition of moving bodies such as fixing belts without the influences of ghost light generated in the light emission to and/or the light reception from the moving bodies. By using the reflection type optical sensors regarding the present invention, it is possible to so precisely detect the variation of the surface condition of the moving bodies that the image generation apparatus having such reflection type optical sensors enables to realize and keep high quality of the images and further to cut the cost for maintenance etc. of the image generation apparatus by reducing the frequency of exchanging fixing members that are consumables of such image generation apparatus.

As some preferred embodiments in the present invention have been disclosed and explained their details in the above discussion. However, the present invention is not limited to these embodiments. One skilled in the art should understand that various modifications and changes can be made in these embodiments.

Since many embodiments of the invention can be made without departing from the spirit and scope of the invention, the invention also resides in the claims hereinafter appended.

What is claimed is:

1. A reflection type optical sensor that detects a surface condition of a moving body, comprising:
    a plurality of light emitter systems including a plurality of light-emitting members;
    a light-emitting optical system having a plurality of light-emitting lenses corresponding to the plurality of light emitter systems and guiding light emitted from the light emitter systems to the moving body;
    a light receiver system including a plurality of light-receiving members;
    a light-receiving optical system having light-receiving lenses corresponding to the plurality of light-receiving members and guiding light reflected on the moving body to the light receiver system; and
    a planar portion provided at a border between the light-emitting lenses and the light-receiving lenses,
    wherein the light-emitting lenses and the light-receiving lenses are arranged such that optical axes of the light-emitting lenses and the light-receiving lenses are parallel with each other, and the planar portion is parallel to the optical axes, and
    wherein adjacent first and second light emitter systems of the plurality of light emitter systems are arranged such that an interval between a light-emitting member positioned closest to the second light emitter system side of the light-emitting members included in the first light emitter system and a light-emitting member positioned closest to the first light emitter system side of the light-emitting members included in the second light emitter system is larger than an arranged interval of the plurality of light-emitting members included in the first light emitter system.

2. The reflection type optical sensor according to claim 1, wherein the light-emitting members of the light emitter systems have even numbers, and the light-emitting lenses are arranged such that each optical axis position of the plurality of light-emitting lenses is between arbitrary two light-receiving members of the plurality of light-receiving members.

3. The reflection type optical sensor according to claim 1, wherein at least two light-emitting members of a light emitter system are arranged to have surface symmetry to a surface which includes an optical axis of a light-emitting lens corresponding thereto.

4. The reflection type optical sensor according to claim 1, wherein a light-receiving member is placed at a position in an optical axis of the light-receiving lens farther than a position of a light-emitting lens from a light-emitting member in an optical axis of the light emitter system.

5. The reflection type optical sensor according to claim 1, wherein an open-end space is formed between the light-emitting optical system and the light-receiving optical system.

6. The reflection type optical sensor according to claim 1, wherein a light-receiving lens is a cylindrical lens which converts an incidental light only into a direction of an arrangement of the at least two light-receiving members.

7. The reflection type optical sensor according to claim 1, wherein a light-emitting lens of the light-emitting optical system and a light-receiving lens of the light-receiving optical system are formed into a single element.

8. The reflection type optical sensor according to claim 1, wherein a light-blocking member is disposed between a light emitter system and the light-emitting optical system.

9. The reflection type optical sensor according to claim 3, wherein the at least two light-emitting members are configured to generate optical spots on the moving body which sequentially turn on/off by turning-on/off light emitted from at least two light-emitting members.

10. The reflection type optical sensor according to claim 3, wherein the at least two light-emitting members are configured to simultaneously generate optical spots.

11. The reflection type optical sensor according to claim 1, wherein a line formed by optical spots has an arbitrary declination angle to a direction of an arrangement of the plurality of light emitter systems.

12. An image generation apparatus which forms images on a recording media comprising: the image generation apparatus according to claim 1, wherein the reflection type optical sensor is configured to detect a surface condition of the moving body which is configured to fix images on the recording media.

13. An image generation apparatus, comprising:
a fixing device; and
the reflection type optical sensor of claim 1,
the fixing device including:
   a rotating fixing member;
   a pressing member that abuts with an outer circumferential surface of the fixing member and is configured to form a nipping part that fixes unfixed toner on a recording media passing, on the recording media; and
   a heating member that heats the fixing member,
wherein the reflection type optical sensor is configured to detect a surface condition of the fixing member and is disposed to form a plurality of optical spots in a direction intersecting to a rotation direction of the fixing member.

14. The image generation apparatus according to claim 13, wherein the fixing member is a fixing belt.

15. A reflection type optical sensor that detects a surface condition of a moving body, comprising:
a plurality of light emitter systems including a plurality of light-emitting members;
a light-emitting optical system having a plurality of light-emitting lenses corresponding to the plurality of light emitter systems and guiding light emitted from the light emitter systems to the moving body;
a light receiver system including a plurality of light-receiving members; and
a light-receiving optical system having light-receiving lenses corresponding to the plurality of light-receiving members and guiding light reflected on the moving body to the light receiver system,
wherein adjacent first and second light emitter systems of the plurality of light emitter systems are arranged such that an interval between a light-emitting member positioned closest to the second light emitter system side of the light-emitting members included in the first light emitter system and a light-emitting member positioned closest to the first light emitter system side of the light-emitting members included in the second light emitter system is larger than an arranged interval of the plurality of light-emitting members included in the first light emitter system.

16. The reflection type optical sensor according to claim 15, wherein the light-emitting members of the light emitter systems have even numbers, and the light-emitting lenses are arranged such that each optical axis position of the plurality of light-emitting lenses is between arbitrary two light-receiving members of the plurality of light-receiving members.

17. The reflection type optical sensor according to claim 15, wherein a line formed by optical spots has an arbitrary declination angle to a direction of an arrangement of the plurality of light emitter systems.

18. An image generation apparatus, comprising:
a fixing device; and
the reflection type optical sensor of claim 15,
the fixing device including:
   a rotating fixing member;
   a pressing member that abuts with an outer circumferential surface of the fixing member and is configured to form a nipping part that fixes unfixed toner on a recording media passing, on the recording media; and
   a heating member that heats the fixing member,
wherein the reflection type optical sensor is configured to detect a surface condition of the fixing member and is disposed to form a plurality of optical spots in a direction intersecting to a rotation direction of the fixing member.

19. The image generation apparatus according to claim 18, wherein the fixing member is a fixing belt.

* * * * *